United States Patent [19]
Whitlow et al.

[11] Patent Number: 6,121,424
[45] Date of Patent: Sep. 19, 2000

[54] MULTIVALENT ANTIGEN-BINDING PROTEINS

[75] Inventors: Marc D. Whitlow, Gaithersburg; James F. Wood, Germantown, both of Md.; Karl D. Hardman, Wynnewood, Pa.; Robert E. Bird, Rockville, Md.; David Filpula, Gaithersburg, Md.; Michele Rollence, Damascus, Md.

[73] Assignee: Enzon, Inc., Piscataway, N.J.

[21] Appl. No.: 09/166,094

[22] Filed: Oct. 5, 1998

Related U.S. Application Data

[62] Division of application No. 08/392,338, Feb. 22, 1995, Pat. No. 5,869,620, which is a division of application No. 07/989,846, Nov. 20, 1992, abandoned, which is a continuation-in-part of application No. 07/796,936, Nov. 25, 1991, abandoned.

[51] Int. Cl.⁷ .................. A61K 39/395; C07K 16/00; C07K 16/44; C07K 16/46
[52] U.S. Cl. .................. 530/387.3; 424/133.1; 424/134.1; 424/135.1; 424/136.1
[58] Field of Search .................. 424/133.1, 134.1, 424/135.1, 136.1; 435/70.21, 451, 453, 455, 328, 252.3, 252.33, 320.1; 530/387.3; 536/23.4, 23.53

[56] References Cited

U.S. PATENT DOCUMENTS

| | | | |
|---|---|---|---|
| 4,085,443 | 4/1978 | Dubois et al. | 364/900 |
| 4,266,253 | 5/1981 | Matherat | 358/903 |
| 4,355,023 | 10/1982 | Ehrlich et al. | 424/85 |
| 4,414,629 | 11/1983 | Waite | 364/300 |
| 4,434,156 | 2/1984 | Trowbridge | 424/85 |
| 4,444,878 | 4/1984 | Paulus | 435/7 |
| 4,470,925 | 9/1984 | Auditore-Hargreaves | 260/112 B |
| 4,479,895 | 10/1984 | Auditore-Hargreaves | 260/112 B |
| 4,642,334 | 2/1987 | Moore et al. | 530/388 |
| 4,704,692 | 11/1987 | Ladner | 364/496 |
| 4,816,397 | 3/1989 | Boss et al. | 435/68 |
| 4,816,567 | 3/1989 | Cabilly et al. | 530/387 |
| 4,853,871 | 8/1989 | Pantoliano et al. | 364/496 |
| 4,861,581 | 8/1989 | Epstein et al. | 424/1.1 |
| 4,881,175 | 11/1989 | Ladner et al. | 364/496 |
| 4,908,773 | 3/1990 | Pantoliano et al. | 364/496 |
| 4,939,666 | 7/1990 | Hardman | 364/496 |
| 4,946,778 | 8/1990 | Ladner et al. | 435/69.6 |
| 5,019,368 | 5/1991 | Epstein et al. | 424/1.1 |
| 5,091,513 | 2/1992 | Huston et al. | 530/387.3 |
| 5,132,405 | 7/1992 | Huston et al. | 530/387.3 |
| 5,160,723 | 11/1992 | Welt et al. | 424/1.1 |
| 5,258,498 | 11/1993 | Huston et al. | 530/350 |
| 5,260,203 | 11/1993 | Ladner et al. | 435/172.3 |
| 5,476,786 | 12/1995 | Huston | 435/252.33 |
| 5,534,254 | 7/1996 | Huston et al. | 424/135.1 |
| 5,591,828 | 1/1997 | Bosslet et al. | 530/387.3 |
| 5,763,733 | 6/1998 | Whitlow et al. | 530/387.3 |
| 5,767,260 | 6/1998 | Whitlow et al. | 536/23.4 |
| 5,844,094 | 12/1998 | Hudson et al. | 530/387.3 |

FOREIGN PATENT DOCUMENTS

| | | |
|---|---|---|
| 0 088 994 | 9/1983 | European Pat. Off. . |
| 0 120 694 | 10/1984 | European Pat. Off. . |
| 0 125 023 | 11/1984 | European Pat. Off. . |
| 0 294 703 | 12/1988 | European Pat. Off. . |
| 0 365 997 | 5/1990 | European Pat. Off. . |
| 0 506 124 | 9/1992 | European Pat. Off. . |
| WO 86/01533 | 3/1986 | WIPO . |
| WO 88/01649 | 3/1988 | WIPO . |
| WO 88/07085 | 9/1988 | WIPO . |
| WO 88/07086 | 9/1988 | WIPO . |
| WO 88/09344 | 12/1988 | WIPO . |
| WO 90/06133 | 6/1990 | WIPO . |
| WO 91/19739 | 12/1991 | WIPO . |
| WO 92/15682 | 9/1992 | WIPO . |
| WO 93/15210 | 8/1993 | WIPO . |
| WO 93/16185 | 8/1993 | WIPO . |
| WO 94/04691 | 3/1994 | WIPO . |
| WO 94/09817 | 5/1994 | WIPO . |
| WO 94/13804 | 6/1994 | WIPO . |

OTHER PUBLICATIONS

LeBerthon, B. et al., "Enhanced Tumor Uptake of Macromolecules Induced by a Novel Vasoactive Interleukin 2 Immunoconjugate," *Cancer Research* 51(10):2694–2698 (May 15, 1991).

Gillies, S.D. et al., "Antibody–targeted interleukin 2 stimulates T–cell killing of autologous tumor cells," *Proc. Natl. Acad. Sci. USA* 69(4):1428–1432 (Feb. 1992).

Batra, J.K., et al., "Anti–Tac(Fv)–PE40, a Single Chain Antibody Pseudomonas Fusion Protein Directed at Interleukin 2 Receptor Bearing Cells," *J. Biol. Chem.* 265:15198–15202 (Sep. 1990).

Breitling, F., et al., "A surface expression vector for antibody screening," *Gene* 104:147–153 (Aug. 1991).

Chaudhary, V.J., et al., "A recombinant immunotoxin consisting of two antibody variable domains fused to Pseudomonas exotoxin," *Nature* 339:394–397 (Jun. 1989).

Clements, J.D., "Construction of a Nontoxic Fusion Peptide for Immunization against *Escherichia coli* Strains That Produce Heat–Labile and Heat–Stable Enterotoxins," *Infect. Immun.* 58:1159–1166 (May 1990).

(List continued on next page.)

*Primary Examiner*—Robert D. Budens
*Attorney, Agent, or Firm*—Sterne, Kessler, Goldstein & Fox P.L.L.C.

[57] ABSTRACT

Compositions of, genetic constructions coding for, and methods for producing multivalent antigen-binding proteins are described and claimed. The methods include purification of compositions containing both monomeric and multivalent forms of single polypeptide chain molecules, and production of multivalent proteins from purified monomers. Production of multivalent proteins may occur by a concentration-dependent association of monomeric proteins, or by rearrangement of regions involving dissociation followed by reassociation of different regions. Bivalent proteins, including homobivalent and heterobivalent proteins, are made in the present invention. Genetic sequences coding for bivalent single-chain antigen-binding proteins are disclosed. Uses include all those appropriate for monoclonal and polyclonal antibodies and fragments thereof, including use as a bispecific antigen-binding molecule.

28 Claims, 39 Drawing Sheets

OTHER PUBLICATIONS

Condra, J.H., et al., "Bacterial Expression of Antibody Fragments That Block Human Rhinovirus Infection of Cultured Cells," *J. Biol. Chem.* 265:2292–2295 (Feb. 1990).

Essig, N.Z., et al., "Crystallization of Single–Chain Fv Proteins," *J. Mol. Biol.* 234:897–901 (Dec. 1993).

Fuchs, P., et al., "Targeting Recombinant Antibodies To The Surface of *Escherichia coli*: Fusion To A Peptidoglycan Associated Lipoprotein," *Bio/Technol.* 9:1369–1372 (Dec. 1991).

Harris, W.J., and Emery, S., "Therapeutic antibodies—the coming of age," *TiBTech* 11:42–44 (Feb. 1993).

Hird, V., and Epenetos, A.A., "Immunotherapy with Monoclonal Antibodies" in : *Genes and Cancer,* Carney, D., and Sikora, K., eds., John Wiley & Sons Ltd., pp. 183–189 (1990).

Holvoet, P., et al., "Characterization of a Chimeric Plasminogen Activator Consisting of a Single–Chain Fv Fragment Derived from a Fibrin Fragment D–Dimer–specific Antibody and a Truncated Single–chain Urokinase," *J. Biol. Chem.* 266:19717–19724 (Oct. 1991).

Huston, J.S., et al., "Medical Applications of Single–Chain Antibodies," *Int. Rev. Immunol* 10:195–217 (1993).

Kim, S.–H., et al., "Redesigning a sweet protein: increased stability and renaturability," *Protein Eng.* 2:571–575 (Aug. 1989).

Laroche, Y., et al., "Characterization of a Recombinant Single–chain Molecule Comprising the Variable Domains of a Monoclonal Antibody Specific for Human Fibrin Fragment D–dimer," *J. Biol. Chem.* 266:16343–16349 (Sep. 1991).

Lehninger, A.L., in: *Principles of Biochemistry,* Worth Publishers, Inc., New York, pp. 150–155 (1982).

Milenic, D.E., et al., "Construction, Binding Properties, Metabolism, and Tumor Targeting of a Single–Chain Fv Derived from the Pancarcinoma Monoclonal Antibody CC49," *Cancer Res.* 51:6363–6371 (Dec. 1991).

Mottez, E., et al., "A single–chain murine class I major transplantation antigen," *Eur. J. Immunol.* 21:467–471 (Feb. 1991).

Novotny, J., et al., "A soluble, single–chain T–cell receptor fragment endowed with antigen–combining properties," *Proc. Natl. Acad. Sci. USA* 88:8646–8650 (Oct. 1991).

Schlom, J., "Monoclonal Antibodies: They're More and Less Than You Think" in: *Molecular Foundations of Oncology,* Broder, S., ed., Williams & Wilkins, Baltimore, MD, pp.95–134 (1991).

Seehaus, T., et al., "A vector for the removal of deletion mutants from antibody libraries," *Gene* 114:235–237 (May 1992).

Soo Hoo, W.F., et al., "Characterization of a single–chain T–cell receptor expressed in *Escherichia coli,*" *Proc. Natl. Acad. Sci. USA* 89:4759–4763 (May 1992).

Takkinen, K., et al., "An active single–chain antibody containing a cellulase linker domain is secreted by *Escherichia coli,*" *Protein Eng.* 4:837–841 (Oct. 1991).

Welt, S., et al., "Quantitative Analysis of Antibody Localization in Human Metastatic Colon Cancer: A Phase I Study of Monoclonal Antibody A33," *J. Clin. Oncol.* 8:1894–1906 (Nov. 1990).

Whitlow, M., et al., "An improved linker for single–chain Fv with reduced aggregation and enhanced proteolytic stability," *Protein Eng.* 6:989–995 (Nov. 1993).

Whitlow, M., and Filpula, D., "Single Chain Fvs," in: *Tumor Immunology: A Practical Approach,* Oxford University Press, pp. 279–291 (1993).

Wootton, J.C., and Drummond, M.H., "The Q–linker: a class of interdomain sequences found in bacterial multidomain regulatory proteins," *Protein Eng.* 2:535–543 (May 1989).

Yokota, T., et al., "Rapid Tumor Penetration of a Single–Chain Fv and Comparison with Other Immunoglobulin Forms," *Cancer Res.* 52:3402–3408 (Jun. 1992).

"Nothing to lose but their chains," *The Economist* (Feb. 27, 1988).

Ahlem, et al., "Regiospecific Coupling of FAB' Fragments for the Production of Synthetic Bifunctional Antibodies," *Targeted Cellular Cytotoxicity and Bispecific Antibodies,* Annapolis, MD, Poster No. 18 (Oct. 22–25, 1989).

Aldred, et al., "Synthesis of rat transferrin in *Escherichia coli* containing a recombinant bacteriophage," *Chem. Abstracts* 101:189 Abstract No. 185187m (1984).

Andrew, et al., "Production of a Single Chain Bispecific Antibody by Recombinant DNA Technology," *Second Intl. Conf. on Bispecific Antibodies and Targeted Cellular Cytotox.,* Seillac, France, Poster No. 21 (Oct. 9–13, 1990).

Aussage, et al., "Bispecific Heteroconjugate of Anti–HB's and Anti–Fc γ RI Prepared by SPDP Method: Production and Bispecificity Analysis," *Second Intl. Conf. on Bispecific Antibodies and Targeted Cellular Cytotox.,* Seillac, France, Poster No. 41 (Oct. 9–13, 1990).

Bedzyk, et al., "Immunological and Structural Characterization of a High Affinity Anti–fluorescein Single–chain Antibody," *J. Biol. Chem.* 265(30):18615–18620 (Oct. 1990).

Bird, et al., "Single–Chain Antigen–Binding Proteins," *Science* 242:423–426 (Oct. 1988).

Bishop, J.E., "Proteins Made by Genex Could Compete With Far Larger Monoclonal Antibodies," *The Wall Street Journal* (Oct. 21, 1988).

Boss, et al., "Assembly of functional antibodies from immunoglobulin in heavy and light chains synthesised in *E. coli,*" *Nucleic Acids Res.* 12(9):3791–3806 (1985).

Boulianne, et al., "Production of functional chimaeric mouse/human antibody," *Nature* 312:643–646 (1984).

Brennan, et al., "Preparation of Bispecific Antibodies by Chemical Recombination of Monoclonal Immunoglobulin $G_1$ Fragments," *Science* 229:81–83 (Jul. 1985).

Brewin–Wilson, D., "Cross–Linked Antibodies Turn Cytotoxic Cells against Cancer," *Oncol. Biototech. News* 3(6):7 (Jun. 1989).

Colcher, et al., "In Vivo Tumor Targeting of a Recombinant Single–Chain Antigen–Binding Protein," *J. Natl. Cancer Inst.* 82(14):1191–1197 (Jul. 1990).

Corvalan, J.R.F. and Smith, W., "Construction and characterisation of a hybrid–hybrid monoclonal antibody recognising both carcinoembryonic antigen (CEA) and vinca alkaloids," *Cancer Immunol. Immunother.* 24:127–132 (1987).

Corvalan, et al., "Tumour Therapy with Vinca Alkaloids Targeted by a Hybrid–Hybrid Monoclonal Antibody Recognising both CEA and Vinca Alkaloids," *Intl. J. Cancer Supp.* 2:22–25 (1988).

Cumber, et al., "Comparative Stabilities in Vitro and in Vivo of a Recombinant Mouse Antibody FvCys Fragment and A bisFvCys Conjugate," *J. Immunol.* 149(1):120–126 (1992).

Davies, D.R. and Metzger, H., "Structural Basis of Antibody Function," *Ann. Rev. Immunol.* 1:87–177 (1983).

Field, et al., "Miniantibodies produced in *E. coli*—Fusion protein expression using dual origin vector," *Dialog File 357: Biotechnology Abstracts,* Accession No. 89–05519 (1987).

Field, et al., "Miniantibodies produced in *E. coli*—Hen egg lysozyme variable region monoclonal antibody gene cloning in *E. coli*," *Dialog File 357: Biotechnology Abstracts,* Accession No. 87–12016 (1987).

Foglesong, et al., "Preparation and analysis of bifunctional immunoconjugates containing monoclonal antibodies OKT3 and BABR1," *Cancer Immunol. Immunother.* 30:177–184 (Oct. 1989).

Foglesong, et al., "Preparation and Characterization of Bifunctional Heteroconjugates Containing OKT3 and Anti–tumor Antibodies," *Third Intl. Conf. on Monoclonal Antibody Immunoconjugates for Cancer,* San Diego, CA, Abstract No. 65 (Feb. 4–6, 1988).

George, et al., "Production of a Bispecific Antibody by Linkage of Two Recombinant Single Chain Fv Molecules," *J. Cell. Biochem. Supp. 15E*:127 Abstract No. N206 (Mar. 1991).

Ghetie, V. and Moraru, I., "Preparation and Applications of Multivalent Antibodies with Dual Specificity," *Meth. Enzymol.* 92:523–543 (1983).

Gilliland, et al., "Bispecific Monoclonal Antibodies and Antibody Heteroconjugates for Enhancement of T Cell Activation and for Targeting Effector Activity Against HIV–Infected Cells," *Targeted Cellular Cytotoxicity and Bispecific Antibodies,* Annapolis, MD, Conf. Abstract (Oct. 22–25, 1989).

Glennie, et al., "Bispecific and Trispecific Antibody Derivatives for the Retargeting of Cytotoxic T Cells," *Targeted Cellular Cytotoxicity and Bispecific Antibodies,* Annapolis, MD, Conf. Abstract (Oct. 22–25, 1989).

Glennie, et al., "Preparation and Performance of Bispecific F(ab'γ)$_2$ Antibody Containing Thioether–Linked Fab'γ Fragments," *J. Immunol.* 139(7):2367–2375 (Oct. 1987).

Goldenberg, et al., "Cancer Diagnosis and Therapy with Radiolabeled Antibodies," in: Immunoconjugates, Antibody Conjugates in Radioimaging and Therapy of Cancer, C.–W. Vogel, ed., Oxford University Press, NY, pp. 259–280 (1987).

Görög, et al., "Use of bispecific hybrid antibodies for the development of a homogeneous enzyme immunoassay," *J. Immunol. Meth.* 123:131–140 (Sep. 1989).

Griffiths, et al., "Human anti–self antibodies with high specificity from phage display libraries," *EMBO J.* 12(2):725–734 (Feb. 1993).

Herron, J.N., "Equilibrium and Kinetic Methodology for the Measurement of Binding Properties in Monoclonal and Polyclonal Populations of Antifluorescyl–IgG Antibodies," in: Fluorescein Hapten: An Immunological Probe, E.W. Voss, ed., CRC Press, Boca Raton, FL, pp. 49–76 (1984).

Honda, et al., "A human hybrid hybridoma producing a bispecific monoclonal antibody that can target tumor cells for attack by *Pseudomonas aeruginosa* exotoxin A," *Cytotechnology* 4:59–68 (Jul. 1990).

Huber, R. "Structural Basis for Antigen–Antibody Recognition," *Science* 253:702–703 (Aug. 1986).

Hudson, et al., "Immunoglobulin Chain Recombination Among Antidigoxin Antibodies by Hybridoma–Hybridoma Fusion," *J. Immunol.* 139(8):2715–2723 (Oct. 1987).

Huston, et al., "Engineering of Antibody Binding Sites to Tumor Antigens," *SBIR Grant Title Page/Abstract,* Phase I Grant, Creative BioMolecules, Inc. (1985).

Huston, et al., "Engineering of Antibody Binding Sites to Tumor Antigens," *SBIR Grant Title Page/Abstract,* Phase II Grant, Creative BioMolecules, Inc. (1986).

Huston, et al., "Protein Engineering of Antibody Binding Sites: Recovery of Specific Activity in an Anti–digoxin Single–chain Fv Analogue Produced in *Escherichia coli*," *PNAS USA* 85:5879–5883 (Aug. 1988).

Jung, G., "Target Cell Induced T Cell Activation with Antibody Heteroconjugates," *Targeted Cellular Cytotoxicity and Bispecific Antibodies,* Annapolis, MD, Conf. Abstract (Oct. 22–25, 1989).

Karawajew, et al., "Bispecific antibody–producing hybrid hybridomas selected by a fluorescence activated cell sorter," *J. Immunol. Meth.* 96:265–270 (Feb. 1987).

Klausner, A., "Single–Chain Antibodies Become a Reality," *Bio/Technology* 4:1041,1043 (Dec. 1986).

Kühn, et al., "Gene Transfer, Expression, and Molecular Cloning of the Human Transferrin Receptor Gene," *Cell* 37:95–103 (1984).

Kurokawa, et al., "Enhanced Fibrinolysis by a Bispecific Monoclonal Antibody Reactive to Fibrin and Tissue Plasminogen Activator," *Bio/Technology* 7:1163–1167 (Nov. 1989).

Lanzavecchia, A. and Scheidegger, D., "The use of hybrid hybridomas to target human cytotoxic T lymphocytes," *Eur. J. Immunol.* 17:105–111 (Jan. 1987).

Levinson, et al., "Biosynthetic antibody sites: Studies of an anti–digoxin Fv region—recombinant monoclonal antibody preparation," *Dialog File 357: Biotechnology Abstracts,* Accession No. 87–11664 (1987).

Maddon, et al., "The Isolation and Nucleotide Sequence of a cDNA Encoding the T Cell Surface Protein T4: A New Member of the Immunoglobulin Gene Family," *Cell* 42:93–104 (Aug. 1985).

Mandache, et al., "Simultaneous detection of two different cell surface antigens by electron microscopy by means of multivalent hybrid antibody with double specificity," *J. Immunol. Meth.* 42:355–365 (1981).

McGregor, et al., "Spontaneous Assembly of Bivalent Single Chain Antibody Fragments in *Escherichia coli*," *Molec. Immunol* 31(3):219–226 (1994).

Mézes, et al., "Molecular Design of Anti–Tumor Single Chain Fv Species," *Third Annual IBC Intl. Conf. on Antibody Engineering,* San Diego, CA, Conf. Abstract (Dec. 14–16, 1992).

Mezzanzanica, et al., "Human Ovarian Carcinoma Lysis by Cytotoxic T Cells Targeted by Bispecific Monoclonal Antibodies: Analysis of the Antibody Components," *Intl. J. Cancer* 41:609–615 (Apr. 1988).

Mezzanzanica, et al., "Human T Cells are Targeted Against Human Ovarian Carcinoma Cells by Bifunctional F(ab')$_2$ Antibodies Stably Joined by Thioether Linkages," *Targeted Cellular Cytotoxicity and Bispecific Antibodies,* Annapolis, MD, Poster No. 15 (Oct. 22–25, 1989).

Milstein, C. and Cuello, A.C., "Hybrid hybridomas and their use in immunohistochemistry," *Nature* 305:537–540 (1983).

Morrison, S.L., "Transfectomas Provide Novel Chimeric Antibodies," *Science* 229:1202–1207 (Sep. 1985).

Morrison, et al., "Chimeric human antibody molecules: Mouse antigen–binding domains with human constant region domains," *PNAS USA* 81:6851–6855 (1984).

Mota, et al., "Preparation and Some Properties of Dimeric Rabbit IgG Antibody," *Molec. Immunol.* 21(7):641–645 (1984).

Munro, A., "Uses of Chimeric Antibodies," *Nature* 312:597–598 (1984).

Muraro, et al., "Generation and Characterization of B72.3 Second Generation Monoclonal Antibodies Reactive with the Tumor–associated Glycoprotein 72 Antigen," *Cancer Res.* 48:4588–4596 (Aug. 1988).

Neuberger, et al., "Recombinant antibodies possessing novel effector functions," *Nature* 312:604–608 (1984).

Nisonoff, A. and Rivers, M.M., "Recombination of a Mixture of Univalent Antibody Fragments of Different Specificity," *Arch. Biochem. Biophys.* 93:460–462 (1961).

Oi, V.T., "Chimeric Antibodies," *BioTechniques* 4(3):214–221 (1986).

Pantoliano, et al., "Conformational Stability, Folding, and Ligand–Binding Affinity of Single–Chain Fv Immunoglobulin Fragments Expressed in *Escherichia coli*," *Biochemistry* 30(42):10117–10125 (Oct. 1991).

Partis, et al., "Cross–Linking of Protein by ω–Maleimido Alkanoyl N–Hydroxysuccinimido Esters," *J. Protein Chem.* 2(3):263–277 (1983).

Pastan, et al., "Immunotoxins," *Cells* 47:641–648 (Dec. 1986).

Pimm, et al., "A bispecific monoclonal antibody against methotrexate and a human tumour associated antigen augments cytotoxicity of methotrexate–carrier conjugate," *Br. J. Cancer* 61:508–513 (Apr. 1990).

Raso, V. and Griffin, T., "Hybrid Antibodies with Dual Specificity for the Delivery of Ricin to Immunoglobulin–bearing Target Cells," *Cancer Res.* 41:2073–2078 (1981).

Roitt, I.M., in: Essential Immunology, 6th Ed., Blackwell Scientific Publications, Boston, MA, p. 38 (1988).

Runge, et al., "Antibody Enhanced Thrombolysis: (1) Capture of Endogenous Tissue Plasminogen Activator (tPA) by a Heteroantibody Duplex and (2) Direct Targeting by an Antifibrin–tPA Conjugate In Vivo," *Clin. Res.* 35(3):643A (1987).

Scott, et al., "Requirements for the Construction of Antibody Heterodimers for the Direction of Lysis of Tumors by Human T Cells," *J. Clin. Invest.* 81:1427–1433 (May 1988).

Segal, et al., "Targeting of Cytotoxic Cells against Tumors with Heterocrosslinked, Bispecific Antibodies," in: Immune System and Cancer, Hamaoka et al., eds., Japan Sci. Soc. Press, Tokyo, Japan, pp. 323–331 (1989).

Segal, et al., "Targeting of Cytotoxic Cells with Heterocrosslinked Antibodies," *Cancer Invest.* 6(1):83–92 (1988).

Snider, D.P. and Segal, D.M., "Targeted Antigen Presentation Using Crosslinked Antibody Heteroaggregates," *J. Immunol.* 139(5):1609–1616 (Sep. 1987).

Songsivilai, S. and Lachmann, P.J., "Bispecific antibody: a tool for diagnosis and treatment of disease," *Clin. Exp. Immunol.* 79:315–321 (Mar. 1990).

Staerz, et al., "Hybrid antibodies can target sites for attack by T cells," *Nature* 314:628–631 (Apr. 1985).

Sukhatme, et al., "The T Cell Differentiation Antigen Leu–2/T8 Is Homologous to Immunoglobulin and T Cell Receptor Variable Regions," *Cell* 40:591–597 (Mar. 1985).

Titus, et al., "Human T Cells Targeted with Anti–T3 Cross–linked to Antitumor Antibody Prevent Tumor Growth in Nude Mice," *J. Immunol.* 138(11):4018–4022 (Jun. 1987).

Traunecker, et al., "Bispecific single chain molecules (Janusins) target cytotoxic lymphocytes on HIV infected cells," *EMBO J.* 10(12):3655–3659 (Dec. 1991).

Urnovitz, et al., "IgA:IgM and IgA:IgA Hybrid Hybridomas Secrete Heteropolymeric Immunoglobulins that are Polyvalent and Bispecific," *J. Immunol.* 140(2):558–563 (Jan. 1988).

Van Brunt, J., "Protein Architecture: Designing from the Ground Up," *Bio/Technology* 4(4):277–283 (Apr. 1986).

Vitetta, et al., "Immunotoxins: A New Approach to Cancer Therapy," *Science* 219:644–650 (1983).

Waldmann, T.A., "Monoclonal Antibodies in Diagnosis and Therapy," *Science* 252:1657–1662 (Jun. 1991).

Weidner, et al., "Molecular Stabilization Effects of Interactions between Anti–metatype Antibodies and Liganded Antibody," *J. Biol. Chem.* 267(15):10281–10288 (May 1992).

Whitlow, et al., "Multivalent Fvs: characterization of single–chain Fv oligomers and preparation of a bispecific Fv," *Protein Eng.* 7(8):1017–1026 (Aug. 1994).

Whitlow, et al., "Single–Chain Fv Proteins and Their Fusion Proteins," *Methods* 2(3):1–9 (Apr. 1991).

Wood, et al., "The synthesis and in vivo assembly of functional antibodies in yeast," *Nature* 314:446–449 (Apr. 1985).

Holliger, P., et al., "'Diabodies': Small bivalent and bispecific antibody fragments," *Proc. Natl. Acad. Sci. USA* 90:6444–6448 (Jul. 1993).

Huston, et al., "Protein Engineering of Single–Chain Fv Analogs and Fusion Proteins," in *Methods in Enzymology Molecular Design and Modeling: Concepts and Applications*, vol. 203, Langone, J.J., ed., Academic Press, Inc., pp. 46–88 (1991).

McGuinness, B.T., et al., "Phage diabody repertoires for selection of large numbers of bispecific antibody fragments," *Nature Biotechnol.* 14:1149–1154 (Sep. 1996).

Nisonoff, et al., "Quantitative estimation of the hybridization of rabbit antibodies," *Nature* 194:355–359 (1962).

McNeil, D., and Freiberger, P., "Fuzzy Delphi," in: *Fuzzy Logic*, Simon & Schuster, New York, pp. 209–227 (1993).

Whitlow, M., and Filpula, D., "Single–Chain Fv Proteins and Their Fusion Proteins," *Methods: A Companion to Methods in Enzymology* 2(2):97–105 (Apr. 1991).

Zhu, Z., et al., "High Level Secretion of a Humanized Bispecific Diabody from *Escherichia coli*," *Bio/Technol.* 14:192–196 (Feb. 1996).

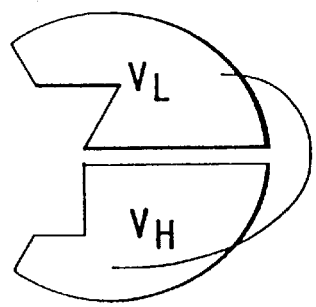 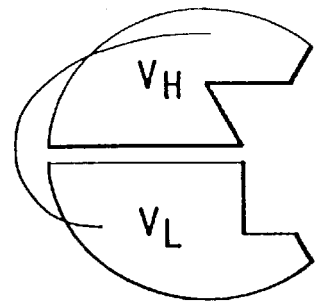
ANTI-B VL – ANTI-A VH        ANTI-A VL – ANTI-B VH
FIG.5A
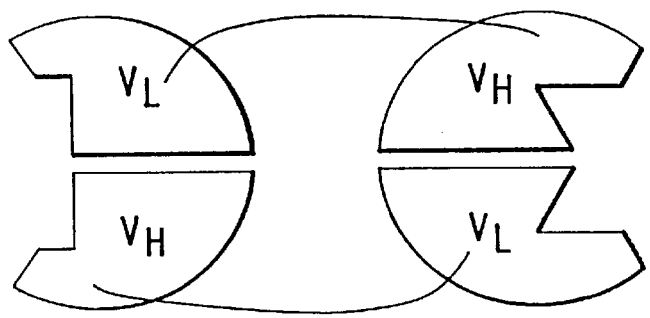
FIG.5B
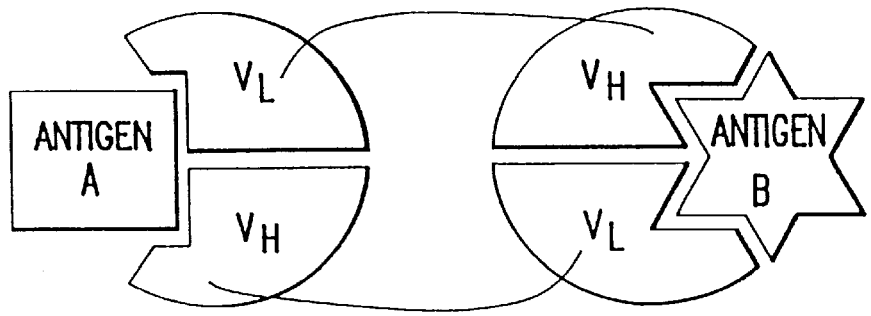
FIG.5C 4-4-20 V$_L$/212/CC49 V$_H$ gene

```
4-4-20 V_L                                              10                                                    2
Asp Val Val Met Thr Gln Thr Pro Leu Ser Leu Pro Val Ser Leu Gly Asp Gln Ala Ser
GAC GTC GTT ATG ACT CAG ACA CCA CTA TCA CTT CCT GTT AGT CTA GGT GAT CAA GCC TCC
Aat II
                                                        30                                                   40
Ile Ser Cys Arg Ser Ser Gln Ser Leu Val His Ser Asn Gly Asn Thr Tyr Leu Arg Trp
ATC TCT TGC AGA TCT AGT CAG AGC CTT GTA CAC AGT AAT GGA AAC ACC TAT TTA CGT TGG 50                                                   60
Tyr Leu Gln Lys Pro Gly Gln Ser Pro Lys Val Leu Ile Tyr Lys Val Ser Asn Arg Phe
TAC CTG CAG AAG CCA GGC CAG TCT CCA AAG GTC CTG ATC TAC AAA GTT TCC AAC CGA TTT 70                                                   80
Ser Gly Val Pro Asp Arg Phe Ser Gly Ser Gly Ser Gly Thr Asp Phe Thr Leu Lys Ile
TCT GGG GTC CCA GAC AGG TTC AGT GGC AGT GGA TCA GGG ACA GAT TTC ACA CTC AAG ATC 90                                                  100
Ser Arg Val Glu Ala Glu Asp Leu Gly Val Tyr Phe Cys Ser Gln Ser Thr His Val Pro
AGC AGA GTG GAG GCT GAG GAT CTG GGA GTT TAT TTC TGC TCT CAA AGT ACA CAT GTT CCG 110        212 Linker                                            120
Trp Thr Phe Gly Gly Gly Thr Lys Leu Glu Ile Lys Gly Ser Thr Ser Gly Ser Gly Lys
TGG ACG TTC GGT GGA GGC ACC AAG CTT GAA ATC AAA GGT TCT ACC TCT GGT TCT GGT AAA
                                           Hind III
                      CC49 V_H           130                                                                140
Ser Ser Glu Gly Lys Gly Gln Val Gln Leu Gln Gln Ser Asp Ala Glu Leu Val Lys Pro
TCC TCT GAA GGC AAA GGT CAG GTT CAG CTG CAG CAG TCT GAC GCT GAG TTG GTG AAA CCT
                                              PvuII PstI
                                                       150                                                  160
Gly Ala Ser Val Lys Ile Ser Cys Lys Ala Ser Gly Tyr Thr Phe Thr Asp His Ala Ile
GGG GCT TCA GTG AAG ATT TCC TGC AAG GCT TCT GGC TAC ACC TTC ACT GAC CAT GCA ATT 170                                                  180
His Trp Val Lys Gln Asn Pro Glu Gln Gly Leu Glu Trp Ile Gly Tyr Phe Ser Pro Gly
CAC TGG GTG AAA CAG AAC CCT GAA CAG GGC CTG GAA TGG ATT GGA TAT TTT TCT CCC GGA
```

FIG.10A 4-4-20 V$_L$/212/CC49 V$_H$ gene

```
                                190                                            200
Asn Asp Asp Phe Lys Tyr Asn Glu Arg Phe Lys Gly Lys Ala Thr Leu Thr Ala Asp Lys
AAT GAT GAT TTT AAA TAC AAT GAG AGG TTC AAG GGC AAG GCC ACA CTG ACT GCA GAC AAA 210                                            220
Ser Ser Ser Thr Ala Tyr Val Gln Leu Asn Ser Leu Thr Ser Glu Asp Ser Ala Val Tyr
TCC TCC AGC ACT GCC TAC GTG CAG CTC AAC AGC CTG ACA TCT GAG GAT TCT GCA GTG TAT 230                                            240
Phe Cys Thr Arg Ser Leu Asn Met Ala Tyr Trp Gly Gln Gly Thr Ser Val Thr Val Ser
TTC TGT ACA AGA TCC CTG AAT ATG GCC TAC TGG GGT CAA GGA ACC TCA GTC ACC GTC TCC xxx xxx Asp
TAA TAG GAT CC
      ‾‾‾‾‾‾
      Bam H1
```

FIG.10A-1

CC49 V$_L$/212/4-4-20 V$_H$ gene

CC49 V$_L$

```
                                  10                                    20
Asp Val Val Met Ser Gln Ser Pro Ser Ser Leu Pro Val Ser Val Gly Glu Lys Val Thr
GAC GTC GTG ATG TCA CAG TCT CCA TCC TCC CTA CCT GTG TCA GTT GGC GAG AAG GTT ACT
Aat II
                                  30                                    40
Leu Ser Cys Lys Ser Ser Gln Ser Leu Leu Tyr Ser Gly Asn Gln Lys Asn Tyr Leu Ala
TTG AGC TGC AAG TCC AGT CAG AGC CTT TTA TAT AGT GGT AAT CAA AAG AAC TAC TTG GCC 50                                    60
Trp Tyr Gln Gln Lys Pro Gly Gln Ser Pro Lys Leu Leu Ile Tyr Trp Ala Ser Ala Arg
TGG TAC CAG CAG AAA CCA GGG CAG TCT CCT AAA CTG CTG ATT TAC TGG GCA TCC GCT AGG 70                                    80
Glu Ser Gly Val Pro Asp Arg Phe Thr Gly Ser Gly Ser Gly Thr Asp Phe Thr Leu Ser
GAA TCT GGG GTC CCT GAT CGC TTC ACA GGC AGT GGA TCT GGG ACA GAT TTC ACT CTC TCC 90                                   100
Ile Ser Ser Val Lys Thr Glu Asp Leu Ala Val Tyr Tyr Cys Gln Gln Tyr Tyr Ser Tyr
ATC AGC AGT GTG AAG ACT GAA GAC CTG GCA GTT TAT TAC TGT CAG CAG TAT TAT AGC TAT 110           212 Linker             120
Pro Leu Thr Phe Gly Ala Gly Thr Lys Leu Val Leu Lys Gly Ser Thr Ser Gly Ser Gly
CCC CTC ACG TTC GGT GCT GGG ACC AAG CTT GTG CTG AAA GGC TCT ACT TCC GGT AGC GGC
                                         Hind III
        4-4-20 V$_H$                                                  140
Lys Ser Ser Glu Gly Lys Gly Glu Val Lys Leu Asp Glu Thr Gly Gly Gly Leu Val Gln
AAA TCT TCT GAA GGT AAA GGT GAA GTT AAA CTG GAT GAG ACT GGA GGA GGC TTG GTG CAA 150                                   160
Pro Gly Arg Pro Met Lys Leu Ser Cys Val Ala Ser Gly Phe Thr Phe Ser Asp Tyr Trp
CCT GGG AGG CCC ATG AAA CTC TCC TGT GTT GCC TCT GGA TTC ACT TTT AGT GAC TAC TGG 170                                   180
Met Asn Trp Val Arg Gln Ser Pro Glu Lys Gly Leu Glu Trp Val Ala Gln Ile Arg Asn
ATG AAC TGG GTC CGC CAG TCT CCA GAG AAA GGA CTG GAG TGG GTA GCA CAA ATT AGA AAC
```

FIG. 10B

CC49 V_L/212/4-4-20 V_H gene

```
                                190                                              200
Lys Pro Tyr Asn Tyr Glu Thr Tyr Tyr Ser Asp Ser Val Lys Gly Arg Phe Thr Ile Ser
AAA CCT TAT AAT TAT GAA ACA TAT TAT TCA GAT TCT GTG AAA GGC AGA TTC ACC ATC TCA 210                                              220
Arg Asp Asp Ser Lys Ser Ser Val Tyr Leu Gln Met Asn Asn Leu Arg Val Glu Asp Met
AGA GAT GAT TCC AAA AGT AGT GTC TAC CTG CAA ATG AAC AAC TTA AGA GTT GAA GAC ATG 230                                              240
Gly Ile Tyr Tyr Cys Thr Gly Ser Tyr Tyr Gly Met Asp Tyr Trp Gly Gln Gly Thr Ser
GGT ATC TAT TAC TGT ACG GGT TCT TAC TAT GGT ATG GAC TAC TGG GGT CAA GGA ACC TCA

Val Thr Val Ser  *   *  Gly Ser
GTC ACC GTC TCC TAA TAA GGA TCC
                             Bam H1
```

FIG.10B-1

4-4-20/212     protein with single cysteine hinge 4-4-20 V_L                          10                                              20
Asp Val Val Met Thr Gln Thr Pro Leu Ser Leu Pro Val Ser Leu Gly Asp Gln Ala Ser
GAC GTC GTT ATG ACT CAG ACA CCA CTA TCA CTT CCT GTT AGT CTA GGT GAT CAA GCC TCC
Aat II
                                    30                                              40
Ile Ser Cys Arg Ser Ser Gln Ser Leu Val His Ser Asn Gly Asn Thr Tyr Leu Arg Trp
ATC TCT TGC AGA TCT AGT CAG AGC CTT GTA CAC AGT AAT GGA AAC ACC TAT TTA CGT TGG 50                                              60
Tyr Leu Gln Lys Pro Gly Gln Ser Pro Lys Val Leu Ile Tyr Lys Val Ser Asn Arg Phe
TAC CTG CAG AAG CCA GGC CAG TCT CCA AAG GTC CTG ATC TAC AAA GTT TCC AAC CGA TTT 70                                              80
Ser Gly Val Pro Asp Arg Phe Ser Gly Ser Gly Ser Gly Thr Asp Phe Thr Leu Lys Ile
TCT GGG GTC CCA GAC AGG TTC AGT GGC AGT GGA TCA GGG ACA GAT TTC ACA CTC AAG ATC 90                                             100
Ser Arg Val Glu Ala Glu Asp Leu Gly Val Tyr Phe Cys Ser Gln Ser Thr His Val Pro
AGC AGA GTG GAG GCT GAG GAT CTG GGA GTT TAT TTC TGC TCT CAA AGT ACA CAT GTT CCG 110          212 Linker                         120
Trp Thr Phe Gly Gly Gly Thr Lys Leu Glu Ile Lys Gly Ser Thr Ser Gly Ser Gly Lys
TGG ACG TTC GGT GGA GGC ACC AAG CTT GAA ATC AAA GGT TCT ACC TCT GGT TCT GGT AAA
                                         Hind III
           4-4-20 V_H                                                              140
Ser Ser Glu Gly Lys Gly Glu Val Lys Leu Asp Glu Thr Gly Gly Gly Leu Val Gln Pro
TCT TCT GAA GGT AAA GGT GAA GTT AAA CTG GAT GAG ACT GGA GGA GGC TTG GTG CAA CCT 150                                             160
Gly Arg Pro Met Lys Leu Ser Cys Val Ala Ser Gly Phe Thr Phe Ser Asp Tyr Trp Met
GGG AGG CCC ATG AAA CTC TCC TGT GTT GCC TCT GGA TTC ACT TTT AGT GAC TAC TGG ATG 170                                             180
Asn Trp Val Arg Gln Ser Pro Glu Lys Gly Leu Glu Trp Val Ala Gln Ile Arg Asn Lys
AAC TGG GTC CGC CAG TCT CCA GAG AAA GGA CTG GAG TGG GTA GCA CAA ATT AGA AAC AAA

FIG.15A 4-4-20/212  protein with single cysteine hinge

```
                                         190                                         200
Pro Tyr Asn Tyr Glu Thr Tyr Tyr Ser Asp Ser Val Lys Gly Arg Phe Thr Ile Ser Arg
CCT TAT AAT TAT GAA ACA TAT TAT TCA GAT TCT GTG AAA GGC AGA TTC ACC ATC TCA AGA 210                                         220
Asp Asp Ser Lys Ser Ser Val Tyr Leu Gln Met Asn Asn Leu Arg Val Glu Asp Met Gly
GAT GAT TCC AAA AGT AGT GTC TAC CTG CAA ATG AAC AAC TTA AGA GTT GAA GAC ATG GGT 230                                         240
Ile Tyr Tyr Cys Thr Gly Ser Tyr Tyr Gly Met Asp Tyr Trp Gly Gln Gly Thr Ser Val
ATC TAT TAC TGT ACG GGT TCT TAC TAT GGT ATG GAC TAC TGG GGT CAA GGA ACC TCG GTC
                                                                         Bst EII

Hinge            250
Thr Val Ser Ser Asp Lys Thr His Thr Cys *** ***
ACC GTC TCC AGT GAT AAG ACC CAT ACA TGC TAA TAG GAT CC
                                                Bam H1
pGx 5532, Gx 8932
```

FIG.15A-1

4-4-20/212 protein with two cysteine hinge 4-4-20 V_L

```
                                  10                                    20
Asp Val Val Met Thr Gln Thr Pro Leu Ser Leu Pro Val Ser Leu Gly Asp Gln Ala Ser
GAC GTC GTT ATG ACT CAG ACA CCA CTA TCA CTT CCT GTT AGT CTA GGT GAT CAA GCC TCC
‾‾‾‾‾‾‾
Aat II
                                  30                                    40
Ile Ser Cys Arg Ser Ser Gln Ser Leu Val His Ser Asn Gly Asn Thr Tyr Leu Arg Trp
ATC TCT TGC AGA TCT AGT CAG AGC CTT GTA CAC AGT AAT GGA AAC ACC TAT TTA CGT TGG 50                                    60
Tyr Leu Gln Lys Pro Gly Gln Ser Pro Lys Val Leu Ile Tyr Lys Val Ser Asn Arg Phe
TAC CTG CAG AAG CCA GGC CAG TCT CCA AAG GTC CTG ATC TAC AAA GTT TCC AAC CGA TTT 70                                    80
Ser Gly Val Pro Asp Arg Phe Ser Gly Ser Gly Ser Gly Thr Asp Phe Thr Leu Lys Ile
TCT GGG GTC CCA GAC AGG TTC AGT GGC AGT GGA TCA GGG ACA GAT TTC ACA CTC AAG ATC 90                                   100
Ser Arg Val Glu Ala Glu Asp Leu Gly Val Tyr Phe Cys Ser Gln Ser Thr His Val Pro
AGC AGA GTG GAG GCT GAG GAT CTG GGA GTT TAT TTC TGC TCT CAA AGT ACA CAT GTT CCG 110           212 Linker               120
Trp Thr Phe Gly Gly Gly Thr Lys Leu Glu Ile Lys Gly Ser Thr Ser Gly Ser Gly Lys
TGG ACG TTC GGT GGA GGC ACC AAG CTT GAA ATC AAA GGT TCT ACC TCT GGT TCT GGT AAA
                                     ‾‾‾‾‾‾‾   ‾‾‾‾‾‾‾‾‾‾‾‾‾‾‾‾‾‾‾‾‾‾‾‾‾‾‾‾‾‾‾‾‾
                                     Hind III
               4-4-20 V_H        130                                   140
Ser Ser Glu Gly Lys Gly Glu Val Lys Leu Asp Glu Thr Gly Gly Gly Leu Val Gln Pro
TCT TCT GAA GGT AAA GGT GAA GTT AAA CTG GAT GAG ACT GGA GGA GGC TTG GTG CAA CCT
‾‾‾‾‾‾‾‾‾‾‾‾‾‾‾‾‾‾‾‾‾‾‾‾‾

150                                   160
Gly Arg Pro Met Lys Leu Ser Cys Val Ala Ser Gly Phe Thr Phe Ser Asp Tyr Trp Met
GGG AGG CCC ATG AAA CTC TCC TGT GTT GCC TCT GGA TTC ACT TTT AGT GAC TAC TGG ATG 170                                   180
Asn Trp Val Arg Gln Ser Pro Glu Lys Gly Leu Glu Trp Val Ala Gln Ile Arg Asn Lys
AAC TGG GTC CGC CAG TCT CCA GAG AAA GGA CTG GAG TGG GTA GCA CAA ATT AGA AAC AAA
```

FIG.15B 4-4-20/212 protein with two cysteine hinge

```
                                190                                        200
Pro Tyr Asn Tyr Glu Thr Tyr Tyr Ser Asp Ser Val Lys Gly Arg Phe Thr Ile Ser Arg
CCT TAT AAT TAT GAA ACA TAT TAT TCA GAT TCT GTG AAA GGC AGA TTC ACC ATC TCA AGA 210                                        220
Asp Asp Ser Lys Ser Ser Val Tyr Leu Gln Met Asn Asn Leu Arg Val Glu Asp Met Gly
GAT GAT TCC AAA AGT AGT GTC TAC CTG CAA ATG AAC AAC TTA AGA GTT GAA GAC ATG GGT 230                                        240
Ile Tyr Tyr Cys Thr Gly Ser Tyr Tyr Gly Met Asp Tyr Trp Gly Gln Gly Thr Ser Val
ATC TAT TAC TGT ACG GGT TCT TAC TAT GGT ATG GAC TAC TGG GGT CAA GGA ACC TCG GTC
                                                                         Bst EII
         Hinge                  250
Thr Val Ser Ser Asp Lys Thr His Thr Cys Pro Pro Cys *** ***
ACC GTC TCC AGT GAT AAG ACC CAT ACA TGC CCT CCA TGC TAA TAG GAT CC
                                                            Bam H1
pGx 5533, Gx 8933
```

FIG.15B-1

CC49/212 SCA™ protein genetic dimer

CC49 V<sub>L</sub>

```
                                           10                               20
Asp Val Val Met Ser Gln Ser Pro Ser Ser Leu Pro Val Ser Val Gly Glu Lys Val Thr
GAC GTC GTG ATG TCA CAG TCT CCA TCC TCC CTA CCT GTG TCA GTT GGC GAG AAG GTT ACT
Aat II
                                           30                               40
Leu Ser Cys Lys Ser Ser Gln Ser Leu Leu Tyr Ser Gly Asn Gln Lys Asn Tyr Leu Ala
TTG AGC TGC AAG TCC AGT CAG AGC CTT TTA TAT AGT GGT AAT CAA AAG AAC TAC TTG GCC 50                               60
Trp Tyr Gln Gln Lys Pro Gly Gln Ser Pro Lys Leu Leu Ile Tyr Trp Ala Ser Ala Arg
TGG TAC CAG CAG AAA CCA GGG CAG TCT CCT AAA CTG CTG ATT TAC TGG GCA TCC GCT AGG 70                               80
Glu Ser Gly Val Pro Asp Arg Phe Thr Gly Ser Gly Ser Gly Thr Asp Phe Thr Leu Ser
GAA TCT GGG GTC CCT GAT CGC TTC ACA GGC AGT GGA TCT GGG ACA GAT TTC ACT CTC TCC 90                              100
Ile Ser Ser Val Lys Thr Glu Asp Leu Ala Val Tyr Tyr Cys Gln Gln Tyr Tyr Ser Tyr
ATC AGC AGT GTG AAG ACT GAA GAC CTG GCA GTT TAT TAC TGT CAG CAG TAT TAT AGC TAT 110       212 Linker               120
Pro Leu Thr Phe Gly Ala Gly Thr Lys Leu Val Leu Lys Gly Ser Thr Ser Gly Ser Gly
CCC CTC ACG TTC GGT GCT GGG ACC AAG CTT GTG CTG AAA GGC TCT ACT TCC GGT AGC GGC
                                          Hind III
                                                   CC49 V<sub>H</sub>          140
Lys Ser Ser Glu Gly Lys Gly Gln Val Gln Leu Gln Gln Ser Asp Ala Glu Leu Val Lys
AAA TCC TCT GAA GGC AAA GGT CAG GTT CAG CTG CAG CAG TCT GAC GCT GAG TTG GTG AAA
                                              PvuII PstI
                                          150                              160
Pro Gly Ala Ser Val Lys Ile Ser Cys Lys Ala Ser Gly Tyr Thr Phe Thr Asp His Ala
CCT GGG GCT TCA GTG AAG ATT TCC TGC AAG GCT TCT GGC TAC ACC TTC ACT GAC CAT GCA 170                              180
Ile His Trp Val Lys Gln Asn Pro Glu Gln Gly Leu Glu Trp Ile Gly Tyr Phe Ser Pro
ATT CAC TGG GTG AAA CAG AAC CCT GAA CAG GGC CTG GAA TGG ATT GGA TAT TTT TCT CCC
```

FIG.16A

CC49/212 SCA™ protein genetic dimer

```
                                      190                                          200
      Gly Asn Asp Asp Phe Lys Tyr Asn Glu Arg Phe Lys Gly Lys Ala Thr Leu Thr Ala Asp
      GGA AAT GAT GAT TTT AAA TAC AAT GAG AGG TTC AAG GGC AAG GCC ACA CTG ACT GCA GAC 210                                          220
      Lys Ser Ser Ser Thr Ala Tyr Val Gln Leu Asn Ser Leu Thr Ser Glu Asp Ser Ala Val
      AAA TCC TCC AGC ACT GCC TAC GTG CAG CTC AAC AGC CTG ACA TCT GAG GAT TCT GCA GTG 230                                          240
      Tyr Phe Cys Thr Arg Ser Leu Asn Met Ala Tyr Trp Gly Gln Gly Thr Ser Val Thr Val
      TAT TTC TGT ACA AGA TCC CTG AAT ATG GCC TAC TGG GGT CAA GGA ACC TCA GTC ACC GTC

CC49 V_L                  250                                          260
      Ser Ser Asp Val Val Met Ser Gln Ser Pro Ser Ser Leu Pro Val Ser Val Gly Glu Lys
      TCC TCA GAC GTC GTG ATG TCA CAG TCT CCA TCC TCC CTA CCT GTG TCA GTT GGC GAG AAG
              Aat II 270                                          280
      Val Thr Leu Ser Cys Lys Ser Ser Gln Ser Leu Leu Tyr Ser Gly Asn Gln Lys Asn Tyr
      GTT ACT TTG AGC TGC AAG TCC AGT CAG AGC CTT TTA TAT AGT GGT AAT CAA AAG AAC TAC 290                                          300
      Leu Ala Trp Tyr Gln Gln Lys Pro Gly Gln Ser Pro Lys Leu Leu Ile Tyr Trp Ala Ser
      TTG GCC TGG TAC CAG CAG AAA CCA GGG CAG TCT CCT AAA CTG CTG ATT TAC TGG GCA TCC 310                                          320
      Ala Arg Glu Ser Gly Val Pro Asp Arg Phe Thr Gly Ser Gly Ser Gly Thr Asp Phe Thr
      GCT AGG GAA TCT GGG GTC CCT GAT CGC TTC ACA GGC AGT GGA TCT GGG ACA GAT TTC ACT 330                                          340
      Leu Ser Ile Ser Ser Val Lys Thr Glu Asp Leu Ala Val Tyr Tyr Cys Gln Gln Tyr Tyr
      CTC TCC ATC AGC AGT GTG AAG ACT GAA GAC CTG GCA GTT TAT TAC TGT CAG CAG TAT TAT 350                    212 Linker             360
      Ser Tyr Pro Leu Thr Phe Gly Ala Gly Thr Lys Leu Val Leu Lys Gly Ser Thr Ser Gly
      AGC TAT CCC CTC ACG TTC GGT GCT GGG ACC AAG CTT GTG CTG AAA GGC TCT ACT TCC GGT
                                              Hind III
                     CC49 V_H                                                       380
      Ser Gly Lys Ser Ser Glu Gly Lys Gly Gln Val Gln Leu Gln Gln Ser Asp Ala Glu Leu
      AGC GGC AAA TCC TCT GAA GGC AAA GGT CAG GTT CAG CTG CAG CAG TCT GAC GCT GAG TTG
                                                   PvuII PstI
```

FIG.16B

CC49/212 SCA™ protein genetic dimer

```
                                390                                                  400
Val Lys Pro Gly Ala Ser Val Lys Ile Ser Cys Lys Ala Ser Gly Tyr Thr Phe Thr Asp
GTG AAA CCT GGG GCT TCA GTG AAG ATT TCC TGC AAG GCT TCT GGC TAC ACC TTC ACT GAC 410                                                  420
His Ala Ile His Trp Val Lys Gln Asn Pro Glu Gln Gly Leu Glu Trp Ile Gly Tyr Phe
CAT GCA ATT CAC TGG GTG AAA CAG AAC CCT GAA CAG GGC CTG GAA TGG ATT GGA TAT TTT 430                                                  440
Ser Pro Gly Asn Asp Asp Phe Lys Tyr Asn Glu Arg Phe Lys Gly Lys Ala Thr Leu Thr
TCT CCC GGA AAT GAT GAT TTT AAA TAC AAT GAG AGG TTC AAG GGC AAG GCC ACA CTG ACT 450                                                  460
Ala Asp Lys Ser Ser Ser Thr Ala Tyr Val Gln Leu Asn Ser Leu Thr Ser Glu Asp Ser
GCA GAC AAA TCC TCC AGC ACT GCC TAC GTG CAG CTC AAC AGC CTG ACA TCT GAG GAT TCT 470                                                  480
Ala Val Tyr Phe Cys Thr Arg Ser Leu Asn Met Ala Tyr Trp Gly Gln Gly Thr Ser Val
GCA GTG TAT TTC TGT ACA AGA TCC CTG AAT ATG GCC TAC TGG GGT CAA GGA ACC TCA GTC

Thr Val Ser *** *** Asp
ACC GTC TCC TAA TAG GAT CC
                     Bam H1
```

FIG.16C 4-4-20 V$_L$/217/CC49 V$_H$ gene 4-4-20 V$_L$

```
                                        10                                       20
Asp Val Val Met Thr Gln Thr Pro Leu Ser Leu Pro Val Ser Leu Gly Asp Gln Ala Ser
GAC GTC GTT ATG ACT CAG ACA CCA CTA TCA CTT CCT GTT AGT CTA GGT GAT CAA GCC TCC
Aat II
                                        30                                       40
Ile Ser Cys Arg Ser Ser Gln Ser Leu Val His Ser Asn Gly Asn Thr Tyr Leu Arg Trp
ATC TCT TGC AGA TCT AGT CAG AGC CTT GTA CAC AGT AAT GGA AAC ACC TAT TTA CGT TGG 50                                       60
Tyr Leu Gln Lys Pro Gly Gln Ser Pro Lys Val Leu Ile Tyr Lys Val Ser Asn Arg Phe
TAC CTG CAG AAG CCA GGC CAG TCT CCA AAG GTC CTG ATC TAC AAA GTT TCC AAC CGA TTT 70                                       80
Ser Gly Val Pro Asp Arg Phe Ser Gly Ser Gly Ser Gly Thr Asp Phe Thr Leu Lys Ile
TCT GGG GTC CCA GAC AGG TTC AGT GGC AGT GGA TCA GGG ACA GAT TTC ACA CTC AAG ATC 90                                      100
Ser Arg Val Glu Ala Glu Asp Leu Gly Val Tyr Phe Cys Ser Gln Ser Thr His Val Pro
AGC AGA GTG GAG GCT GAG GAT CTG GGA GTT TAT TTC TGC TCT CAA AGT ACA CAT GTT CCG 110        217 Linker                    120
Trp Thr Phe Gly Gly Gly Thr Lys Leu Glu Ile Lys Gly Ser Thr Ser Gly Lys Pro Ser
TGG ACG TTC GGT GGA GGC ACC AAG CTT GAA ATC AAA GGT TCT ACC TCT GGT AAA CCA TCT
                                       Hind III
              CC49 V$_H$                 130                                    140
Glu Gly Lys Gly Gln Val Gln Leu Gln Gln Ser Asp Ala Glu Leu Val Lys Pro Gly Ala
GAA GGC AAA GGT CAG GTT CAG CTG CAG CAG TCT GAC GCT GAG TTG GTG AAA CCT GGG GCT
                        PvuII PstI
                                       150                                      160
Ser Val Lys Ile Ser Cys Lys Ala Ser Gly Tyr Thr Phe Thr Asp His Ala Ile His Trp
TCA GTG AAG ATT TCC TGC AAG GCT TCT GGC TAC ACC TTC ACT GAC CAT GCA ATT CAC TGG 170                                      180
Val Lys Gln Asn Pro Glu Gln Gly Leu Glu Trp Ile Gly Tyr Phe Ser Pro Gly Asn Asp
GTG AAA CAG AAC CCT GAA CAG GGC CTG GAA TGG ATT GGA TAT TTT TCT CCC GGA AAT GAT
```

FIG.19A 4-4-20 V_L/217/CC49 V_H gene

```
                                    190                                         200
Asp Phe Lys Tyr Asn Glu Arg Phe Lys Gly Lys Ala Thr Leu Thr Ala Asp Lys Ser Ser
GAT TTT AAA TAC AAT GAG AGG TTC AAG GGC AAG GCC ACA CTG ACT GCA GAC AAA TCC TCC 210                                         220
Ser Thr Ala Tyr Val Gln Leu Asn Ser Leu Thr Ser Glu Asp Ser Ala Val Tyr Phe Cys
AGC ACT GCC TAC GTG CAG CTC AAC AGC CTG ACA TCT GAG GAT TCT GCA GTG TAT TTC TGT 230                                         240
Thr Arg Ser Leu Asn Met Ala Tyr Trp Gly Gln Gly Thr Ser Val Thr Val Ser * *
ACA AGA TCC CTG AAT ATG GCC TAC TGG GGT CAA GGA ACC TCA GTC ACC GTC TCC TAA TAG
```

Asp
GAT CC
Bam H1

FIG.19A-1

CC49 V_L/217/4-4-20 V_H gene

```
CC49 VL                              10                                          20
Asp Val Val Met Ser Gln Ser Pro Ser Ser Leu Pro Val Ser Val Gly Glu Lys Val Thr
GAC GTC GTG ATG TCA CAG TCT CCA TCC TCC CTA CCT GTG TCA GTT GGC GAG AAG GTT ACT
Aat II
                                     30                                          40
Leu Ser Cys Lys Ser Ser Gln Ser Leu Leu Tyr Ser Gly Asn Gln Lys Asn Tyr Leu Ala
TTG AGC TGC AAG TCC AGT CAG AGC CTT TTA TAT AGT GGT AAT CAA AAG AAC TAC TTG GCC 50                                          60
Trp Tyr Gln Gln Lys Pro Gly Gln Ser Pro Lys Leu Leu Ile Tyr Trp Ala Ser Ala Arg
TGG TAC CAG CAG AAA CCA GGG CAG TCT CCT AAA CTG CTG ATT TAC TGG GCA TCC GCT AGG 70                                          80
Glu Ser Gly Val Pro Asp Arg Phe Thr Gly Ser Gly Ser Gly Thr Asp Phe Thr Leu Ser
GAA TCT GGG GTC CCT GAT CGC TTC ACA GGC AGT GGA TCT GGG ACA GAT TTC ACT CTC TCC 90                                          100
Ile Ser Ser Val Lys Thr Glu Asp Leu Ala Val Tyr Tyr Cys Gln Gln Tyr Tyr Ser Tyr
ATC AGC AGT GTG AAG ACT GAA GAC CTG GCA GTT TAT TAC TGT CAG CAG TAT TAT AGC TAT 110               217 Linker               120
Pro Leu Thr Phe Gly Ala Gly Thr Lys Leu Val Leu Lys Gly Ser Thr Ser Gly Lys Pro
CCC CTC ACG TTC GGT GCT GGG ACC AAG CTT GTG CTG AAA GGC TCT ACT TCC GGT AAA CCA
                                      Hind III
            4-4-20 VH                130                                         140
Ser Glu Gly Lys Gly Glu Val Lys Leu Asp Glu Thr Gly Gly Gly Leu Val Gln Pro Gly
TCT GAA GGT AAA GGT GAA GTT AAA CTG GAT GAG ACT GGA GGA GGC TTG GTG CAA CCT GGG 150                                         160
Arg Pro Met Lys Leu Ser Cys Val Ala Ser Gly Phe Thr Phe Ser Asp Tyr Trp Met Asn
AGG CCC ATG AAA CTC TCC TGT GTT GCC TCT GGA TTC ACT TTT AGT GAC TAC TGG ATG AAC 170                                         180
Trp Val Arg Gln Ser Pro Glu Lys Gly Leu Glu Trp Val Ala Gln Ile Arg Asn Lys Pro
TGG GTC CGC CAG TCT CCA GAG AAA GGA CTG GAG TGG GTA GCA CAA ATT AGA AAC AAA CCT
```

FIG.19B

CC49 V_L/217/4-4-20 V_H gene

```
                                      190                                 200
Tyr Asn Tyr Glu Thr Tyr Tyr Ser Asp Ser Val Lys Gly Arg Phe Thr Ile Ser Arg Asp
TAT AAT TAT GAA ACA TAT TAT TCA GAT TCT GTG AAA GGC AGA TTC ACC ATC TCA AGA GAT 210                                 220
Asp Ser Lys Ser Ser Val Tyr Leu Gln Met Asn Asn Leu Arg Val Glu Asp Met Gly Ile
GAT TCC AAA AGT AGT GTC TAC CTG CAA ATG AAC AAC TTA AGA GTT GAA GAC ATG GGT ATC 230                                 240
Tyr Tyr Cys Thr Gly Ser Tyr Tyr Gly Met Asp Tyr Trp Gly Gln Gly Thr Ser Val Thr
TAT TAC TGT ACG GGT TCT TAC TAT GGT ATG GAC TAC TGG GGT CAA GGA ACC TCA GTC ACC

Val Ser *** *** Gly Ser
GTC TCC TAA TAA GGA TCC
                Bam H1
```

FIG.19B-1

PROCESSING FILE: PolyCatA/Proc.CC-49Prep
METHOD: PREP POLY CAT A#2
INJECT VOL: 44
SAMPLING INT: 0.3 SECONDS

CHROMATOGRAM:

| ANALYSIS: | CHANNEL A | | | | |
|---|---|---|---|---|---|
| PEAK NO. | TIME | TYPE | HEIGHT($\mu V$) | AREA($\mu V$-SEC) | AREA% |
| 1 | 17.090 | N1 | 1651 | 348239 | 0.778 |
| 2 | 18.940 | N2 | 8014 | 669441 | 1.496 |
| 3 | 21.775 | N3 | 104401 | 8617252 | 19.263 |
| 4 | 30.100 | N4 | 74925 | 9753616 | 21.804 |
| 5 | 33.455 | N5 | 106864 | 15749605 | 35.208 |
| 6 | 38.940 | N6 | 17296 | 2833701 | 6.334 |
| 7 | 42.010 | N7 | 12645 | 1637917 | 3.661 |
| 8 | 44.640 | N8 | 9287 | 1968584 | 4.400 |
| 9 | 57.055 | N9 | 13767 | 2012338 | 4.498 |
| 10 | 57.610 | N10 | 9323 | 210914 | 0.471 |
| 11 | 58.240 | X11 | 6824 | 930855 | 2.080 |
| TOTAL AREA | | | | 44732462 | 99.993 |

PROCESSING FILE: PolyCatA/Proc.CC-49Prep
METHOD: CC-49 QC SIZE-EXCLUSION
INJECT VOL: .05
SAMPLING INT: 0.1 SECONDS

CHROMATOGRAM:

| ANALYSIS: | CHANNEL A | | | | |
|---|---|---|---|---|---|
| PEAK NO. | TIME | TYPE | HEIGHT($\mu$V) | AREA($\mu$V-SEC) | AREA% |
| 1 | 19.370 | N1 | 797 | 41706 | 5.694 |
| 2 | 20.525 | N2 | 11789 | 657280 | 89.737 |
| 3 | 22.851 | N3 | 1227 | 33466 | 4.569 |
| TOTAL AREA | | | | 732452 | 100.000 |

PROCESSING FILE: PolyCatA/Proc.CC-49Prep
METHOD: CC-49 QC SIZE-EXCLUSION
INJECT VOL: .05
SAMPLING INT: 0.1 SECONDS

CHROMATOGRAM:

| ANALYSIS: | CHANNEL A | | | | |
|---|---|---|---|---|---|
| PEAK NO. | TIME | TYPE | HEIGHT($\mu$V) | AREA($\mu$V-SEC) | AREA% |
| 1 | 19.133 | N1 | 14211 | 749671 | 88.214 |
| 2 | 20.538 | N2 | 1863 | 100154 | 11.785 |
| TOTAL AREA | | | | 849825 | 99.999 |

PROCESSING FILE: PolyCatA/Proc.CC-49Prep
METHOD: CC-49 QC SIZE-EXCLUSION
INJECT VOL: .05
SAMPLING INT: 0.1 SECONDS

CHROMATOGRAM:

| ANALYSIS: | CHANNEL A | | | | |
|---|---|---|---|---|---|
| PEAK NO. | TIME | TYPE | HEIGHT($\mu$V) | AREA($\mu$V-SEC) | AREA% |
| 1 | 19.163 | N1 | 17550 | 876502 | 83.039 |
| 2 | 20.435 | N2 | 2981 | 179029 | 16.961 |
| TOTAL AREA | | | | 1055531 | 100.000 |

```
                       SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
        (A) LENGTH: 12 amino acids
        (B) TYPE: amino acid
        (D) TOPOLOGY: both (xi) SEQUENCE DESCRIPTION: SEQ ID NO:1:

Gly Lys Ser Ser Gly Ser Gly Ser Glu Ser Lys Ser
1               5                   10

(2) INFORMATION FOR SEQ ID NO:2:

(i) SEQUENCE CHARACTERISTICS:
        (A) LENGTH: 14 amino acids
        (B) TYPE: amino acid
        (D) TOPOLOGY: both (xi) SEQUENCE DESCRIPTION: SEQ ID NO:2:

Gly Ser Thr Ser Gly Ser Gly Lys Ser Ser Glu Gly Lys Gly
1               5                   10

(2) INFORMATION FOR SEQ ID NO:3:

(i) SEQUENCE CHARACTERISTICS:
        (A) LENGTH: 18 amino acids
        (B) TYPE: amino acid
        (D) TOPOLOGY: both (xi) SEQUENCE DESCRIPTION: SEQ ID NO:3:

Gly Ser Thr Ser Gly Ser Gly Lys Ser Ser Glu Gly Ser Gly Ser Thr
1               5                   10                  15

Lys Gly
```

(2) INFORMATION FOR SEQ ID NO:4:

(i) SEQUENCE CHARACTERISTICS:
        (A) LENGTH: 12 amino acids
        (B) TYPE: amino acid
        (D) TOPOLOGY: both (xi) SEQUENCE DESCRIPTION: SEQ ID NO:4:

```
Gly Ser Thr Ser Gly Lys Pro Ser Glu Gly Lys Gly
1               5                   10
```

(2) INFORMATION FOR SEQ ID NO:5:

(i) SEQUENCE CHARACTERISTICS:
        (A) LENGTH: 15 amino acids
        (B) TYPE: amino acid
        (D) TOPOLOGY: both (xi) SEQUENCE DESCRIPTION: SEQ ID NO:5:

```
Glu Pro Arg Gly Pro Thr Ile Lys Pro Cys Pro Pro Cys Leu Cys
1               5                   10                  15
```

(2) INFORMATION FOR SEQ ID NO:6:

(i) SEQUENCE CHARACTERISTICS:
        (A) LENGTH: 15 amino acids
        (B) TYPE: amino acid
        (D) TOPOLOGY: both (xi) SEQUENCE DESCRIPTION: SEQ ID NO:6:

```
Ala Glu Pro Lys Ser Cys Asp Lys Thr His Thr Cys Pro Pro Cys
1               5                   10                  15
```

(2) INFORMATION FOR SEQ ID NO:7:

(i) SEQUENCE CHARACTERISTICS:
        (A) LENGTH: 4 amino acids
        (B) TYPE: amino acid
        (D) TOPOLOGY: both (xi) SEQUENCE DESCRIPTION: SEQ ID NO:7:

```
Val Thr Val Ser
1
```

(2) INFORMATION FOR SEQ ID NO:8:

(i) SEQUENCE CHARACTERISTICS:
        (A) LENGTH: 11 amino acids
        (B) TYPE: amino acid
        (D) TOPOLOGY: both (xi) SEQUENCE DESCRIPTION: SEQ ID NO:8:

```
Val Thr Val Ser Ser Asp Lys Thr His Thr Cys
1               5                   10
```

(2) INFORMATION FOR SEQ ID NO:9:

(i) SEQUENCE CHARACTERISTICS:
        (A) LENGTH: 14 amino acids
        (B) TYPE: amino acid
        (D) TOPOLOGY: both (xi) SEQUENCE DESCRIPTION: SEQ ID NO:9:

```
Val Thr Val Ser Ser Asp Lys Thr His Thr Cys Pro Pro Cys
1               5                   10
```

(2) INFORMATION FOR SEQ ID NO:10:

(i) SEQUENCE CHARACTERISTICS:
        (A) LENGTH: 731 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 1..720

(xi) SEQUENCE DESCRIPTION: SEQ ID NO:10:

```
GAC GTC GTT ATG ACT CAG ACA CCA CTA TCA CTT CCT GTT AGT CTA GGT        48
Asp Val Val Met Thr Gln Thr Pro Leu Ser Leu Pro Val Ser Leu Gly
 1               5                  10                  15

GAT CAA GCC TCC ATC TCT TGC AGA TCT AGT CAG AGC CTT GTA CAC AGT        96
Asp Gln Ala Ser Ile Ser Cys Arg Ser Ser Gln Ser Leu Val His Ser
                20                  25                  30

AAT GGA AAC ACC TAT TTA CGT TGG TAC CTG CAG AAG CCA GGC CAG TCT       144
Asn Gly Asn Thr Tyr Leu Arg Trp Tyr Leu Gln Lys Pro Gly Gln Ser
        35                  40                  45

CCA AAG GTC CTG ATC TAC AAA GTT TCC AAC CGA TTT TCT GGG GTC CCA       192
Pro Lys Val Leu Ile Tyr Lys Val Ser Asn Arg Phe Ser Gly Val Pro
    50                  55                  60

GAC AGG TTC AGT GGC AGT GGA TCA GGG ACA GAT TTC ACA CTC AAG ATC       240
Asp Arg Phe Ser Gly Ser Gly Ser Gly Thr Asp Phe Thr Leu Lys Ile
 65                  70                  75                  80

AGC AGA GTG GAG GCT GAG GAT CTG GGA GTT TAT TTC TGC TCT CAA AGT       288
Ser Arg Val Glu Ala Glu Asp Leu Gly Val Tyr Phe Cys Ser Gln Ser
                85                  90                  95

ACA CAT GTT CCG TGG ACG TTC GGT GGA GGC ACC AAG CTT GAA ATC AAA       336
Thr His Val Pro Trp Thr Phe Gly Gly Gly Thr Lys Leu Glu Ile Lys
               100                 105                 110

GGT TCT ACC TCT GGT TCT GGT AAA TCC TCT GAA GGC AAA GGT CAG GTT       384
Gly Ser Thr Ser Gly Ser Gly Lys Ser Ser Glu Gly Lys Gly Gln Val
           115                 120                 125

CAG CTG CAG CAG TCT GAC GCT GAG TTG GTG AAA CCT GGG GCT TCA GTG       432
Gln Leu Gln Gln Ser Asp Ala Glu Leu Val Lys Pro Gly Ala Ser Val
   130                 135                 140

AAG ATT TCC TGC AAG GCT TCT GGC TAC ACC TTC ACT GAC CAT GCA ATT       480
Lys Ile Ser Cys Lys Ala Ser Gly Tyr Thr Phe Thr Asp His Ala Ile
145                 150                 155                 160

CAC TGG GTG AAA CAG AAC CCT GAA CAG GGC CTG GAA TGG ATT GGA TAT       528
His Trp Val Lys Gln Asn Pro Glu Gln Gly Leu Glu Trp Ile Gly Tyr
               165                 170                 175

TTT TCT CCC GGA AAT GAT GAT TTT AAA TAC AAT GAG AGG TTC AAG GGC       576
Phe Ser Pro Gly Asn Asp Asp Phe Lys Tyr Asn Glu Arg Phe Lys Gly
           180                 185                 190

AAG GCC ACA CTG ACT GCA GAC AAA TCC TCC AGC ACT GCC TAC GTG CAG       624
Lys Ala Thr Leu Thr Ala Asp Lys Ser Ser Ser Thr Ala Tyr Val Gln
       195                 200                 205

CTC AAC AGC CTG ACA TCT GAG GAT TCT GCA GTG TAT TTC TGT ACA AGA       672
Leu Asn Ser Leu Thr Ser Glu Asp Ser Ala Val Tyr Phe Cys Thr Arg
   210                 215                 220

TCC CTG AAT ATG GCC TAC TGG GGT CAA GGA ACC TCA GTC ACC GTC TCC       720
Ser Leu Asn Met Ala Tyr Trp Gly Gln Gly Thr Ser Val Thr Val Ser
225                 230                 235                 240

TAATAGGATC C                                                          731
```

(2) INFORMATION FOR SEQ ID NO:11:

(i) SEQUENCE CHARACTERISTICS:
        (A) LENGTH: 240 amino acids
        (B) TYPE: amino acid
        (D) TOPOLOGY: linear (ii) MOLECULE TYPE: protein (xi) SEQUENCE DESCRIPTION: SEQ ID NO:11:

```
Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Gly Ser Thr Ser Gly Ser Gly Lys Ser Ser Glu Gly Lys Gly Gln Val
        115                 120                 125

Gln Leu Gln Gln Ser Asp Ala Glu Leu Val Lys Pro Gly Ala Ser Val
    130                 135                 140

Lys Ile Ser Cys Lys Ala Ser Gly Tyr Thr Phe Thr Asp His Ala Ile
145                 150                 155                 160

His Trp Val Lys Gln Asn Pro Glu Gln Gly Leu Glu Trp Ile Gly Tyr
                165                 170                 175

Phe Ser Pro Gly Asn Asp Asp Phe Lys Tyr Asn Glu Arg Phe Lys Gly
            180                 185                 190

Lys Ala Thr Leu Thr Ala Asp Lys Ser Ser Ser Thr Ala Tyr Val Gln
        195                 200                 205

Leu Asn Ser Leu Thr Ser Glu Asp Ser Ala Val Tyr Phe Cys Thr Arg
    210                 215                 220

Ser Leu Asn Met Ala Tyr Trp Gly Gln Gly Thr Ser Val Thr Val Ser
225                 230                 235                 240
```

(2) INFORMATION FOR SEQ ID NO:12:

(i) SEQUENCE CHARACTERISTICS:
        (A) LENGTH: 744 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 1..732

(xi) SEQUENCE DESCRIPTION: SEQ ID NO:12:

```
GAC GTC GTG ATG TCA CAG TCT CCA TCC TCC CTA CCT GTG TCA GTT GGC       48
Asp Val Val Met Ser Gln Ser Pro Ser Ser Leu Pro Val Ser Val Gly
 1               5                  10                  15

GAG AAG GTT ACT TTG AGC TGC AAG TCC AGT CAG AGC CTT TTA TAT AGT       96
Glu Lys Val Thr Leu Ser Cys Lys Ser Ser Gln Ser Leu Leu Tyr Ser
            20                  25                  30
```

```
GGT AAT CAA AAG AAC TAC TTG GCC TGG TAC CAG CAG AAA CCA GGG CAG         144
Gly Asn Gln Lys Asn Tyr Leu Ala Trp Tyr Gln Gln Lys Pro Gly Gln
        35                  40                  45

TCT CCT AAA CTG CTG ATT TAC TGG GCA TCC GCT AGG GAA TCT GGG GTC         192
Ser Pro Lys Leu Leu Ile Tyr Trp Ala Ser Ala Arg Glu Ser Gly Val
 50                  55                  60

CCT GAT CGC TTC ACA GGC AGT GGA TCT GGG ACA GAT TTC ACT CTC TCC         240
Pro Asp Arg Phe Thr Gly Ser Gly Ser Gly Thr Asp Phe Thr Leu Ser
 65                  70                  75                  80

ATC AGC AGT GTG AAG ACT GAA GAC CTG GCA GTT TAT TAC TGT CAG CAG         288
Ile Ser Ser Val Lys Thr Glu Asp Leu Ala Val Tyr Tyr Cys Gln Gln
                 85                  90                  95

TAT TAT AGC TAT CCC CTC ACG TTC GGT GCT GGG ACC AAG CTT GTG CTG         336
Tyr Tyr Ser Tyr Pro Leu Thr Phe Gly Ala Gly Thr Lys Leu Val Leu
                100                 105                 110

AAA GGC TCT ACT TCC GGT AGC GGC AAA TCT TCT GAA GGT AAA GGT GAA         384
Lys Gly Ser Thr Ser Gly Ser Gly Lys Ser Ser Glu Gly Lys Gly Glu
                115                 120                 125

GTT AAA CTG GAT GAG ACT GGA GGA GGC TTG GTG CAA CCT GGG AGG CCC         432
Val Lys Leu Asp Glu Thr Gly Gly Gly Leu Val Gln Pro Gly Arg Pro
130                 135                 140

ATG AAA CTC TCC TGT GTT GCC TCT GGA TTC ACT TTT AGT GAC TAC TGG         480
Met Lys Leu Ser Cys Val Ala Ser Gly Phe Thr Phe Ser Asp Tyr Trp
145                 150                 155                 160

ATG AAC TGG GTC CGC CAG TCT CCA GAG AAA GGA CTG GAG TGG GTA GCA         528
Met Asn Trp Val Arg Gln Ser Pro Glu Lys Gly Leu Glu Trp Val Ala
                165                 170                 175

CAA ATT AGA AAC AAA CCT TAT AAT TAT GAA ACA TAT TAT TCA GAT TCT         576
Gln Ile Arg Asn Lys Pro Tyr Asn Tyr Glu Thr Tyr Tyr Ser Asp Ser
                180                 185                 190

GTG AAA GGC AGA TTC ACC ATC TCA AGA GAT GAT TCC AAA AGT AGT GTC         624
Val Lys Gly Arg Phe Thr Ile Ser Arg Asp Asp Ser Lys Ser Ser Val
                195                 200                 205

TAC CTG CAA ATG AAC AAC TTA AGA GTT GAA GAC ATG GGT ATC TAT TAC         672
Tyr Leu Gln Met Asn Asn Leu Arg Val Glu Asp Met Gly Ile Tyr Tyr
                210                 215                 220

TGT ACG GGT TCT TAC TAT GGT ATG GAC TAC TGG GGT CAA GGA ACC TCA         720
Cys Thr Gly Ser Tyr Tyr Gly Met Asp Tyr Trp Gly Gln Gly Thr Ser
225                 230                 235                 240

GTC ACC GTC TCC TAATAAGGAT CC                                           744
Val Thr Val Ser (2) INFORMATION FOR SEQ ID NO:13:

(i) SEQUENCE CHARACTERISTICS:
        (A) LENGTH: 244 amino acids
        (B) TYPE: amino acid
        (D) TOPOLOGY: linear (ii) MOLECULE TYPE: protein (xi) SEQUENCE DESCRIPTION: SEQ ID NO:13:

Asp Val Val Met Ser Gln Ser Pro Ser Ser Leu Pro Val Ser Val Gly
 1               5                  10                  15

Glu Lys Val Thr Leu Ser Cys Lys Ser Ser Gln Ser Leu Leu Tyr Ser
                20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
 50                  55                  60
```

```
Pro Asp Arg Phe Thr Gly Ser Gly Ser Gly Thr Asp Phe Thr Leu Ser
 65                  70                  75                  80

Ile Ser Ser Val Lys Thr Glu Asp Leu Ala Val Tyr Tyr Cys Gln Gln
                 85                  90                  95

Tyr Tyr Ser Tyr Pro Leu Thr Phe Gly Ala Gly Thr Lys Leu Val Leu
            100                 105                 110

Lys Gly Ser Thr Gly Ser Gly Lys Ser Ser Glu Gly Lys Gly Glu
        115                 120                 125

Val Lys Leu Asp Glu Thr Gly Gly Leu Val Gln Pro Gly Arg Pro
130                 135                 140

Met Lys Leu Ser Cys Val Ala Ser Gly Phe Thr Phe Ser Asp Tyr Trp
145                 150                 155                 160

Met Asn Trp Val Arg Gln Ser Pro Glu Lys Gly Leu Glu Trp Val Ala
                165                 170                 175

Gln Ile Arg Asn Lys Pro Tyr Asn Tyr Glu Thr Tyr Tyr Ser Asp Ser
            180                 185                 190

Val Lys Gly Arg Phe Thr Ile Ser Arg Asp Asp Ser Lys Ser Ser Val
        195                 200                 205

Tyr Leu Gln Met Asn Asn Leu Arg Val Glu Asp Met Gly Ile Tyr Tyr
210                 215                 220

Cys Thr Gly Ser Tyr Tyr Gly Met Asp Tyr Trp Gly Gln Gly Thr Ser
225                 230                 235                 240

Val Thr Val Ser
```

(2) INFORMATION FOR SEQ ID NO:14:

(i) SEQUENCE CHARACTERISTICS:
       (A) LENGTH: 761 base pairs
       (B) TYPE: nucleic acid
       (C) STRANDEDNESS: both
       (D) TOPOLOGY: both (ix) FEATURE:
       (A) NAME/KEY: CDS
       (B) LOCATION: 1..750

(xi) SEQUENCE DESCRIPTION: SEQ ID NO:14:

```
GAC GTC GTT ATG ACT CAG ACA CCA CTA TCA CTT CCT GTT AGT CTA GGT    48
Asp Val Val Met Thr Gln Thr Pro Leu Ser Leu Pro Val Ser Leu Gly
  1               5                  10                  15

GAT CAA GCC TCC ATC TCT TGC AGA TCT AGT CAG AGC CTT GTA CAC AGT    96
Asp Gln Ala Ser Ile Ser Cys Arg Ser Ser Gln Ser Leu Val His Ser
             20                  25                  30

AAT GGA AAC ACC TAT TTA CGT TGG TAC CTG CAG AAG CCA GGC CAG TCT   144
Asn Gly Asn Thr Tyr Leu Arg Trp Tyr Leu Gln Lys Pro Gly Gln Ser
         35                  40                  45

CCA AAG GTC CTG ATC TAC AAA GTT TCC AAC CGA TTT TCT GGG GTC CCA   192
Pro Lys Val Leu Ile Tyr Lys Val Ser Asn Arg Phe Ser Gly Val Pro
     50                  55                  60

GAC AGG TTC AGT GGC AGT GGA TCA GGG ACA GAT TTC ACA CTC AAG ATC   240
Asp Arg Phe Ser Gly Ser Gly Ser Gly Thr Asp Phe Thr Leu Lys Ile
 65                  70                  75                  80

AGC AGA GTG GAG GCT GAG GAT CTG GGA GTT TAT TTC TGC TCT CAA AGT   288
Ser Arg Val Glu Ala Glu Asp Leu Gly Val Tyr Phe Cys Ser Gln Ser
                 85                  90                  95

ACA CAT GTT CCG TGG ACG TTC GGT GGA GGC ACC AAG CTT GAA ATC AAA   336
Thr His Val Pro Trp Thr Phe Gly Gly Gly Thr Lys Leu Glu Ile Lys
            100                 105                 110
```

```
GGT TCT ACC TCT GGT TCT GGT AAA TCT TCT GAA GGT AAA GGT GAA GTT        384
Gly Ser Thr Ser Gly Ser Gly Lys Ser Ser Glu Gly Lys Gly Glu Val
            115                 120                 125

AAA CTG GAT GAG ACT GGA GGA GGC TTG GTG CAA CCT GGG AGG CCC ATG        432
Lys Leu Asp Glu Thr Gly Gly Gly Leu Val Gln Pro Gly Arg Pro Met
130                 135                 140

AAA CTC TCC TGT GTT GCC TCT GGA TTC ACT TTT AGT GAC TAC TGG ATG        480
Lys Leu Ser Cys Val Ala Ser Gly Phe Thr Phe Ser Asp Tyr Trp Met
145                 150                 155                 160

AAC TGG GTC CGC CAG TCT CCA GAG AAA GGA CTG GAG TGG GTA GCA CAA        528
Asn Trp Val Arg Gln Ser Pro Glu Lys Gly Leu Glu Trp Val Ala Gln
                165                 170                 175

ATT AGA AAC AAA CCT TAT AAT TAT GAA ACA TAT TAT TCA GAT TCT GTG        576
Ile Arg Asn Lys Pro Tyr Asn Tyr Glu Thr Tyr Tyr Ser Asp Ser Val
                180                 185                 190

AAA GGC AGA TTC ACC ATC TCA AGA GAT GAT TCC AAA AGT AGT GTC TAC        624
Lys Gly Arg Phe Thr Ile Ser Arg Asp Asp Ser Lys Ser Ser Val Tyr
            195                 200                 205

CTG CAA ATG AAC AAC TTA AGA GTT GAA GAC ATG GGT ATC TAT TAC TGT        672
Leu Gln Met Asn Asn Leu Arg Val Glu Asp Met Gly Ile Tyr Tyr Cys
210                 215                 220

ACG GGT TCT TAC TAT GGT ATG GAC TAC TGG GGT CAA GGA ACC TCG GTC        720
Thr Gly Ser Tyr Tyr Gly Met Asp Tyr Trp Gly Gln Gly Thr Ser Val
225                 230                 235                 240

ACC GTC TCC AGT GAT AAG ACC CAT ACA TGC TAATAGGATC C                   761
Thr Val Ser Ser Asp Lys Thr His Thr Cys
                245                 250

(2) INFORMATION FOR SEQ ID NO:15:

(i) SEQUENCE CHARACTERISTICS:
        (A) LENGTH: 250 amino acids
        (B) TYPE: amino acid
        (D) TOPOLOGY: linear (ii) MOLECULE TYPE: protein (xi) SEQUENCE DESCRIPTION: SEQ ID NO:15:

Asp Val Val Met Thr Gln Thr Pro Leu Ser Leu Pro Val Ser Leu Gly
  1               5                  10                  15

Asp Gln Ala Ser Ile Ser Cys Arg Ser Ser Gln Ser Leu Val His Ser
                20                  25                  30

Asn Gly Asn Thr Tyr Leu Arg Trp Tyr Leu Gln Lys Pro Gly Gln Ser
            35                  40                  45

Pro Lys Val Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Gly Ser Thr Ser Gly Ser Gly Lys Ser Ser Glu Gly Lys Gly Glu Val
            115                 120                 125

Lys Leu Asp Glu Thr Gly Gly Gly Leu Val Gln Pro Gly Arg Pro Met
        130                 135                 140

Lys Leu Ser Cys Val Ala Ser Gly Phe Thr Phe Ser Asp Tyr Trp Met
145                 150                 155                 160
```

```
Asn Trp Val Arg Gln Ser Pro Glu Lys Gly Leu Glu Trp Val Ala Gln
            165                 170                 175

Ile Arg Asn Lys Pro Tyr Asn Tyr Glu Thr Tyr Tyr Ser Asp Ser Val
            180                 185                 190

Lys Gly Arg Phe Thr Ile Ser Arg Asp Asp Ser Lys Ser Ser Val Tyr
            195                 200                 205

Leu Gln Met Asn Asn Leu Arg Val Glu Asp Met Gly Ile Tyr Tyr Cys
            210                 215                 220

Thr Gly Ser Tyr Tyr Gly Met Asp Tyr Trp Gly Gln Gly Thr Ser Val
225                 230                 235                 240

Thr Val Ser Ser Asp Lys Thr His Thr Cys
                245                 250
```

(2) INFORMATION FOR SEQ ID NO:16:

(i) SEQUENCE CHARACTERISTICS:
        (A) LENGTH: 770 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 1..759

(xi) SEQUENCE DESCRIPTION: SEQ ID NO:16:

```
GAC GTC GTT ATG ACT CAG ACA CCA CTA TCA CTT CCT GTT AGT CTA GGT      48
Asp Val Val Met Thr Gln Thr Pro Leu Ser Leu Pro Val Ser Leu Gly
1               5                   10                  15

GAT CAA GCC TCC ATC TCT TGC AGA TCT AGT CAG AGC CTT GTA CAC AGT      96
Asp Gln Ala Ser Ile Ser Cys Arg Ser Ser Gln Ser Leu Val His Ser
                20                  25                  30

AAT GGA AAC ACC TAT TTA CGT TGG TAC CTG CAG AAG CCA GGC CAG TCT     144
Asn Gly Asn Thr Tyr Leu Arg Trp Tyr Leu Gln Lys Pro Gly Gln Ser
            35                  40                  45

CCA AAG GTC CTG ATC TAC AAA GTT TCC AAC CGA TTT TCT GGG GTC CCA     192
Pro Lys Val Leu Ile Tyr Lys Val Ser Asn Arg Phe Ser Gly Val Pro
        50                  55                  60

GAC AGG TTC AGT GGC AGT GGA TCA GGG ACA GAT TTC ACA CTC AAG ATC     240
Asp Arg Phe Ser Gly Ser Gly Ser Gly Thr Asp Phe Thr Leu Lys Ile
65                  70                  75                  80

AGC AGA GTG GAG GCT GAG GAT CTG GGA GTT TAT TTC TGC TCT CAA AGT     288
Ser Arg Val Glu Ala Glu Asp Leu Gly Val Tyr Phe Cys Ser Gln Ser
                85                  90                  95

ACA CAT GTT CCG TGG ACG TTC GGT GGA GGC ACC AAG CTT GAA ATC AAA     336
Thr His Val Pro Trp Thr Phe Gly Gly Gly Thr Lys Leu Glu Ile Lys
                100                 105                 110

GGT TCT ACC TCT GGT TCT GGT AAA TCT TCT GAA GGT AAA GGT GAA GTT     384
Gly Ser Thr Ser Gly Ser Gly Lys Ser Ser Glu Gly Lys Gly Glu Val
            115                 120                 125

AAA CTG GAT GAG ACT GGA GGA GGC TTG GTG CAA CCT GGG AGG CCC ATG     432
Lys Leu Asp Glu Thr Gly Gly Gly Leu Val Gln Pro Gly Arg Pro Met
        130                 135                 140

AAA CTC TCC TGT GTT GCC TCT GGA TTC ACT TTT AGT GAC TAC TGG ATG     480
Lys Leu Ser Cys Val Ala Ser Gly Phe Thr Phe Ser Asp Tyr Trp Met
145                 150                 155                 160

AAC TGG GTC CGC CAG TCT CCA GAG AAA GGA CTG GAG TGG GTA GCA CAA     528
Asn Trp Val Arg Gln Ser Pro Glu Lys Gly Leu Glu Trp Val Ala Gln
                165                 170                 175
```

```
ATT AGA AAC AAA CCT TAT AAT TAT GAA ACA TAT TAT TCA GAT TCT GTG      576
Ile Arg Asn Lys Pro Tyr Asn Tyr Glu Thr Tyr Tyr Ser Asp Ser Val
            180                 185                 190

AAA GGC AGA TTC ACC ATC TCA AGA GAT GAT TCC AAA AGT AGT GTC TAC      624
Lys Gly Arg Phe Thr Ile Ser Arg Asp Asp Ser Lys Ser Ser Val Tyr
        195                 200                 205

CTG CAA ATG AAC AAC TTA AGA GTT GAA GAC ATG GGT ATC TAT TAC TGT      672
Leu Gln Met Asn Asn Leu Arg Val Glu Asp Met Gly Ile Tyr Tyr Cys
        210                 215                 220

ACG GGT TCT TAC TAT GGT ATG GAC TAC TGG GGT CAA GGA ACC TCG GTC      720
Thr Gly Ser Tyr Tyr Gly Met Asp Tyr Trp Gly Gln Gly Thr Ser Val
225                 230                 235                 240

ACC GTC TCC AGT GAT AAG ACC CAT ACA TGC CCT CCA TGC TAATAGGATC C     770
Thr Val Ser Ser Asp Lys Thr His Thr Cys Pro Pro Cys
                245                 250
```

(2) INFORMATION FOR SEQ ID NO:17:

(i) SEQUENCE CHARACTERISTICS:
        (A) LENGTH: 253 amino acids
        (B) TYPE: amino acid
        (D) TOPOLOGY: linear (ii) MOLECULE TYPE: protein (xi) SEQUENCE DESCRIPTION: SEQ ID NO:17:

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu Arg Trp Tyr Leu Gln Lys Pro Gly Gln Ser
            35                  40                  45

Pro Lys Val Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Gly Ser Thr Ser Gly Ser Gly Lys Ser Ser Glu Gly Lys Gly Glu Val
        115                 120                 125

Lys Leu Asp Glu Thr Gly Gly Gly Leu Val Gln Pro Gly Arg Pro Met
130                 135                 140

Lys Leu Ser Cys Val Ala Ser Gly Phe Thr Phe Ser Asp Tyr Trp Met
145                 150                 155                 160

Asn Trp Val Arg Gln Ser Pro Glu Lys Gly Leu Glu Trp Val Ala Gln
                165                 170                 175

Ile Arg Asn Lys Pro Tyr Asn Tyr Glu Thr Tyr Tyr Ser Asp Ser Val
            180                 185                 190

Lys Gly Arg Phe Thr Ile Ser Arg Asp Asp Ser Lys Ser Ser Val Tyr
        195                 200                 205

Leu Gln Met Asn Asn Leu Arg Val Glu Asp Met Gly Ile Tyr Tyr Cys
        210                 215                 220

Thr Gly Ser Tyr Tyr Gly Met Asp Tyr Trp Gly Gln Gly Thr Ser Val
225                 230                 235                 240

Thr Val Ser Ser Asp Lys Thr His Thr Cys Pro Pro Cys
                245                 250
```

(2) INFORMATION FOR SEQ ID NO:18:

(i) SEQUENCE CHARACTERISTICS:
        (A) LENGTH: 1460 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 1..1449

(xi) SEQUENCE DESCRIPTION: SEQ ID NO:18:

```
GAC GTC GTG ATG TCA CAG TCT CCA TCC TCC CTA CCT GTG TCA GTT GGC      48
Asp Val Val Met Ser Gln Ser Pro Ser Ser Leu Pro Val Ser Val Gly
 1               5                  10                  15

GAG AAG GTT ACT TTG AGC TGC AAG TCC AGT CAG AGC CTT TTA TAT AGT      96
Glu Lys Val Thr Leu Ser Cys Lys Ser Ser Gln Ser Leu Leu Tyr Ser
             20                  25                  30

GGT AAT CAA AAG AAC TAC TTG GCC TGG TAC CAG CAG AAA CCA GGG CAG     144
Gly Asn Gln Lys Asn Tyr Leu Ala Trp Tyr Gln Gln Lys Pro Gly Gln
         35                  40                  45

TCT CCT AAA CTG CTG ATT TAC TGG GCA TCC GCT AGG GAA TCT GGG GTC     192
Ser Pro Lys Leu Leu Ile Tyr Trp Ala Ser Ala Arg Glu Ser Gly Val
     50                  55                  60

CCT GAT CGC TTC ACA GGC AGT GGA TCT GGG ACA GAT TTC ACT CTC TCC     240
Pro Asp Arg Phe Thr Gly Ser Gly Ser Gly Thr Asp Phe Thr Leu Ser
 65                  70                  75                  80

ATC AGC AGT GTG AAG ACT GAA GAC CTG GCA GTT TAT TAC TGT CAG CAG     288
Ile Ser Ser Val Lys Thr Glu Asp Leu Ala Val Tyr Tyr Cys Gln Gln
                 85                  90                  95

TAT TAT AGC TAT CCC CTC ACG TTC GGT GCT GGG ACC AAG CTT GTG CTG     336
Tyr Tyr Ser Tyr Pro Leu Thr Phe Gly Ala Gly Thr Lys Leu Val Leu
            100                 105                 110

AAA GGC TCT ACT TCC GGT AGC GGC AAA TCC TCT GAA GGC AAA GGT CAG     384
Lys Gly Ser Thr Ser Gly Ser Gly Lys Ser Ser Glu Gly Lys Gly Gln
        115                 120                 125

GTT CAG CTG CAG CAG TCT GAC GCT GAG TTG GTG AAA CCT GGG GCT TCA     432
Val Gln Leu Gln Gln Ser Asp Ala Glu Leu Val Lys Pro Gly Ala Ser
    130                 135                 140

GTG AAG ATT TCC TGC AAG GCT TCT GGC TAC ACC TTC ACT GAC CAT GCA     480
Val Lys Ile Ser Cys Lys Ala Ser Gly Tyr Thr Phe Thr Asp His Ala
145                 150                 155                 160

ATT CAC TGG GTG AAA CAG AAC CCT GAA CAG GGC CTG GAA TGG ATT GGA     528
Ile His Trp Val Lys Gln Asn Pro Glu Gln Gly Leu Glu Trp Ile Gly
                165                 170                 175

TAT TTT TCT CCC GGA AAT GAT GAT TTT AAA TAC AAT GAG AGG TTC AAG     576
Tyr Phe Ser Pro Gly Asn Asp Asp Phe Lys Tyr Asn Glu Arg Phe Lys
            180                 185                 190

GGC AAG GCC ACA CTG ACT GCA GAC AAA TCC TCC AGC ACT GCC TAC GTG     624
Gly Lys Ala Thr Leu Thr Ala Asp Lys Ser Ser Ser Thr Ala Tyr Val
        195                 200                 205

CAG CTC AAC AGC CTG ACA TCT GAG GAT TCT GCA GTG TAT TTC TGT ACA     672
Gln Leu Asn Ser Leu Thr Ser Glu Asp Ser Ala Val Tyr Phe Cys Thr
    210                 215                 220

AGA TCC CTG AAT ATG GCC TAC TGG GGT CAA GGA ACC TCA GTC ACC GTC     720
Arg Ser Leu Asn Met Ala Tyr Trp Gly Gln Gly Thr Ser Val Thr Val
225                 230                 235                 240

TCC TCA GAC GTC GTG ATG TCA CAG TCT CCA TCC TCC CTA CCT GTG TCA     768
Ser Ser Asp Val Val Met Ser Gln Ser Pro Ser Ser Leu Pro Val Ser
                245                 250                 255
```

```
GTT GGC GAG AAG GTT ACT TTG AGC TGC AAG TCC AGT CAG AGC CTT TTA        816
Val Gly Glu Lys Val Thr Leu Ser Cys Lys Ser Ser Gln Ser Leu Leu
        260                 265                 270

TAT AGT GGT AAT CAA AAG AAC TAC TTG GCC TGG TAC CAG CAG AAA CCA        864
Tyr Ser Gly Asn Gln Lys Asn Tyr Leu Ala Trp Tyr Gln Gln Lys Pro
        275                 280                 285

GGG CAG TCT CCT AAA CTG CTG ATT TAC TGG GCA TCC GCT AGG GAA TCT        912
Gly Gln Ser Pro Lys Leu Leu Ile Tyr Trp Ala Ser Ala Arg Glu Ser
    290                 295                 300

GGG GTC CCT GAT CGC TTC ACA GGC AGT GGA TCT GGG ACA GAT TTC ACT        960
Gly Val Pro Asp Arg Phe Thr Gly Ser Gly Ser Gly Thr Asp Phe Thr
305                 310                 315                 320

CTC TCC ATC AGC AGT GTG AAG ACT GAA GAC CTG GCA GTT TAT TAC TGT       1008
Leu Ser Ile Ser Ser Val Lys Thr Glu Asp Leu Ala Val Tyr Tyr Cys
                325                 330                 335

CAG CAG TAT TAT AGC TAT CCC CTC ACG TTC GGT GCT GGG ACC AAG CTT       1056
Gln Gln Tyr Tyr Ser Tyr Pro Leu Thr Phe Gly Ala Gly Thr Lys Leu
                340                 345                 350

GTG CTG AAA GGC TCT ACT TCC GGT AGC GGC AAA TCC TCT GAA GGC AAA       1104
Val Leu Lys Gly Ser Thr Ser Gly Ser Gly Lys Ser Ser Glu Gly Lys
            355                 360                 365

GGT CAG GTT CAG CTG CAG CAG TCT GAC GCT GAG TTG GTG AAA CCT GGG       1152
Gly Gln Val Gln Leu Gln Gln Ser Asp Ala Glu Leu Val Lys Pro Gly
370                 375                 380

GCT TCA GTG AAG ATT TCC TGC AAG GCT TCT GGC TAC ACC TTC ACT GAC       1200
Ala Ser Val Lys Ile Ser Cys Lys Ala Ser Gly Tyr Thr Phe Thr Asp
385                 390                 395                 400

CAT GCA ATT CAC TGG GTG AAA CAG AAC CCT GAA CAG GGC CTG GAA TGG       1248
His Ala Ile His Trp Val Lys Gln Asn Pro Glu Gln Gly Leu Glu Trp
                405                 410                 415

ATT GGA TAT TTT TCT CCC GGA AAT GAT GAT TTT AAA TAC AAT GAG AGG       1296
Ile Gly Tyr Phe Ser Pro Gly Asn Asp Asp Phe Lys Tyr Asn Glu Arg
                420                 425                 430

TTC AAG GGC AAG GCC ACA CTG ACT GCA GAC AAA TCC TCC AGC ACT GCC       1344
Phe Lys Gly Lys Ala Thr Leu Thr Ala Asp Lys Ser Ser Ser Thr Ala
            435                 440                 445

TAC GTG CAG CTC AAC AGC CTG ACA TCT GAG GAT TCT GCA GTG TAT TTC       1392
Tyr Val Gln Leu Asn Ser Leu Thr Ser Glu Asp Ser Ala Val Tyr Phe
        450                 455                 460

TGT ACA AGA TCC CTG AAT ATG GCC TAC TGG GGT CAA GGA ACC TCA GTC       1440
Cys Thr Arg Ser Leu Asn Met Ala Tyr Trp Gly Gln Gly Thr Ser Val
465                 470                 475                 480

ACC GTC TCC TAATAGGATC C                                              1460
Thr Val Ser (2) INFORMATION FOR SEQ ID NO:19:

(i) SEQUENCE CHARACTERISTICS:
        (A) LENGTH: 483 amino acids
        (B) TYPE: amino acid
        (D) TOPOLOGY: linear (ii) MOLECULE TYPE: protein (xi) SEQUENCE DESCRIPTION: SEQ ID NO:19:

Asp Val Val Met Ser Gln Ser Pro Ser Ser Leu Pro Val Ser Val Gly
 1               5                  10                  15

Glu Lys Val Thr Leu Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45
```

```
Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Ser
65                      70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys Gly Ser Thr Ser Gly Ser Gly Lys Ser Ser Glu Gly Lys Gly Gln
        115                 120                 125

Val Gln Leu Gln Gln Ser Asp Ala Glu Leu Val Lys Pro Gly Ala Ser
    130                 135                 140

Val Lys Ile Ser Cys Lys Ala Ser Gly Tyr Thr Phe Thr Asp His Ala
145                 150                 155                 160

Ile His Trp Val Lys Gln Asn Pro Glu Gln Gly Leu Glu Trp Ile Gly
                165                 170                 175

Tyr Phe Ser Pro Gly Asn Asp Asp Phe Lys Tyr Asn Glu Arg Phe Lys
            180                 185                 190

Gly Lys Ala Thr Leu Thr Ala Asp Lys Ser Ser Ser Thr Ala Tyr Val
        195                 200                 205

Gln Leu Asn Ser Leu Thr Ser Glu Asp Ser Ala Val Tyr Phe Cys Thr
    210                 215                 220

Arg Ser Leu Asn Met Ala Tyr Trp Gly Gln Gly Thr Ser Val Thr Val
225                 230                 235                 240

Ser Ser Asp Val Val Met Ser Gln Ser Pro Ser Ser Leu Pro Val Ser
                245                 250                 255

Val Gly Glu Lys Val Thr Leu Ser Cys Lys Ser Ser Gln Ser Leu Leu
            260                 265                 270

Tyr Ser Gly Asn Gln Lys Asn Tyr Leu Ala Trp Tyr Gln Gln Lys Pro
        275                 280                 285

Gly Gln Ser Pro Lys Leu Leu Ile Tyr Trp Ala Ser Ala Arg Glu Ser
    290                 295                 300

Gly Val Pro Asp Arg Phe Thr Gly Ser Gly Ser Gly Thr Asp Phe Thr
305                 310                 315                 320

Leu Ser Ile Ser Ser Val Lys Thr Glu Asp Leu Ala Val Tyr Tyr Cys
                325                 330                 335

Gln Gln Tyr Tyr Ser Tyr Pro Leu Thr Phe Gly Ala Gly Thr Lys Leu
            340                 345                 350

Val Leu Lys Gly Ser Thr Ser Gly Ser Gly Lys Ser Ser Glu Gly Lys
        355                 360                 365

Gly Gln Val Gln Leu Gln Gln Ser Asp Ala Glu Leu Val Lys Pro Gly
    370                 375                 380

Ala Ser Val Lys Ile Ser Cys Lys Ala Ser Gly Tyr Thr Phe Thr Asp
385                 390                 395                 400

His Ala Ile His Trp Val Lys Gln Asn Pro Glu Gln Gly Leu Glu Trp
                405                 410                 415

Ile Gly Tyr Phe Ser Pro Gly Asn Asp Asp Phe Lys Tyr Asn Glu Arg
            420                 425                 430

Phe Lys Gly Lys Ala Thr Leu Thr Ala Asp Lys Ser Ser Ser Thr Ala
        435                 440                 445
```

```
Tyr Val Gln Leu Asn Ser Leu Thr Ser Glu Asp Ser Ala Val Tyr Phe
    450                 455                 460

Cys Thr Arg Ser Leu Asn Met Ala Tyr Trp Gly Gln Gly Thr Ser Val
465                 470                 475                 480

Thr Val Ser (2) INFORMATION FOR SEQ ID NO:20:

(i) SEQUENCE CHARACTERISTICS:
        (A) LENGTH: 725 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 1..714

(xi) SEQUENCE DESCRIPTION: SEQ ID NO:20:

GAC GTC GTT ATG ACT CAG ACA CCA CTA TCA CTT CCT GTT AGT CTA GGT        48
Asp Val Val Met Thr Gln Thr Pro Leu Ser Leu Pro Val Ser Leu Gly
  1               5                  10                  15

GAT CAA GCC TCC ATC TCT TGC AGA TCT AGT CAG AGC CTT GTA CAC AGT        96
Asp Gln Ala Ser Ile Ser Cys Arg Ser Ser Gln Ser Leu Val His Ser
             20                  25                  30

AAT GGA AAC ACC TAT TTA CGT TGG TAC CTG CAG AAG CCA GGC CAG TCT       144
Asn Gly Asn Thr Tyr Leu Arg Trp Tyr Leu Gln Lys Pro Gly Gln Ser
         35                  40                  45

CCA AAG GTC CTG ATC TAC AAA GTT TCC AAC CGA TTT TCT GGG GTC CCA       192
Pro Lys Val Leu Ile Tyr Lys Val Ser Asn Arg Phe Ser Gly Val Pro
     50                  55                  60

GAC AGG TTC AGT GGC AGT GGA TCA GGG ACA GAT TTC ACA CTC AAG ATC       240
Asp Arg Phe Ser Gly Ser Gly Ser Gly Thr Asp Phe Thr Leu Lys Ile
 65                  70                  75                  80

AGC AGA GTG GAG GCT GAG GAT CTG GGA GTT TAT TTC TGC TCT CAA AGT       288
Ser Arg Val Glu Ala Glu Asp Leu Gly Val Tyr Phe Cys Ser Gln Ser
                 85                  90                  95

ACA CAT GTT CCG TGG ACG TTC GGT GGA GGC ACC AAG CTT GAA ATC AAA       336
Thr His Val Pro Trp Thr Phe Gly Gly Gly Thr Lys Leu Glu Ile Lys
            100                 105                 110

GGT TCT ACC TCT GGT AAA CCA TCT GAA GGC AAA GGT CAG GTT CAG CTG       384
Gly Ser Thr Ser Gly Lys Pro Ser Glu Gly Lys Gly Gln Val Gln Leu
        115                 120                 125

CAG CAG TCT GAC GCT GAG TTG GTG AAA CCT GGG GCT TCA GTG AAG ATT       432
Gln Gln Ser Asp Ala Glu Leu Val Lys Pro Gly Ala Ser Val Lys Ile
    130                 135                 140

TCC TGC AAG GCT TCT GGC TAC ACC TTC ACT GAC CAT GCA ATT CAC TGG       480
Ser Cys Lys Ala Ser Gly Tyr Thr Phe Thr Asp His Ala Ile His Trp
145                 150                 155                 160

GTG AAA CAG AAC CCT GAA CAG GGC CTG GAA TGG ATT GGA TAT TTT TCT       528
Val Lys Gln Asn Pro Glu Gln Gly Leu Glu Trp Ile Gly Tyr Phe Ser
                165                 170                 175

CCC GGA AAT GAT GAT TTT AAA TAC AAT GAG AGG TTC AAG GGC AAG GCC       576
Pro Gly Asn Asp Asp Phe Lys Tyr Asn Glu Arg Phe Lys Gly Lys Ala
            180                 185                 190

ACA CTG ACT GCA GAC AAA TCC TCC AGC ACT GCC TAC GTG CAG CTC AAC       624
Thr Leu Thr Ala Asp Lys Ser Ser Ser Thr Ala Tyr Val Gln Leu Asn
        195                 200                 205

AGC CTG ACA TCT GAG GAT TCT GCA GTG TAT TTC TGT ACA AGA TCC CTG       672
Ser Leu Thr Ser Glu Asp Ser Ala Val Tyr Phe Cys Thr Arg Ser Leu
    210                 215                 220
```

```
AAT ATG GCC TAC TGG GGT CAA GGA ACC TCA GTC ACC GTC TCC TAATAGGATC      724
Asn Met Ala Tyr Trp Gly Gln Gly Thr Ser Val Thr Val Ser
225                 230                 235

C                                                                       725
```

(2) INFORMATION FOR SEQ ID NO:21:

(i) SEQUENCE CHARACTERISTICS:
        (A) LENGTH: 238 amino acids
        (B) TYPE: amino acid
        (D) TOPOLOGY: linear (ii) MOLECULE TYPE: protein (xi) SEQUENCE DESCRIPTION: SEQ ID NO:21:

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu Arg Trp Tyr Leu Gln Lys Pro Gly Gln Ser
            35                  40                  45

Pro Lys Val Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Gly Ser Thr Ser Gly Lys Pro Ser Glu Gly Lys Gly Gln Val Gln Leu
        115                 120                 125

Gln Gln Ser Asp Ala Glu Leu Val Lys Pro Gly Ala Ser Val Lys Ile
130                 135                 140

Ser Cys Lys Ala Ser Gly Tyr Thr Phe Thr Asp His Ala Ile His Trp
145                 150                 155                 160

Val Lys Gln Asn Pro Glu Gln Gly Leu Glu Trp Ile Gly Tyr Phe Ser
                165                 170                 175

Pro Gly Asn Asp Asp Phe Lys Tyr Asn Glu Arg Phe Lys Gly Lys Ala
            180                 185                 190

Thr Leu Thr Ala Asp Lys Ser Ser Thr Ala Tyr Val Gln Leu Asn
        195                 200                 205

Ser Leu Thr Ser Glu Asp Ser Ala Val Tyr Phe Cys Thr Arg Ser Leu
210                 215                 220

Asn Met Ala Tyr Trp Gly Gln Gly Thr Ser Val Thr Val Ser
225                 230                 235
```

(2) INFORMATION FOR SEQ ID NO:22:

(i) SEQUENCE CHARACTERISTICS:
        (A) LENGTH: 738 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 1..726

(xi) SEQUENCE DESCRIPTION: SEQ ID NO:22:

| | | | | | | | | | | | | | | | | |
|---|---|---|---|---|---|---|---|---|---|---|---|---|---|---|---|---|
|GAC|GTC|GTG|ATG|TCA|CAG|TCT|CCA|TCC|TCC|CTA|CCT|GTG|TCA|GTT|GGC|48|
|Asp|Val|Val|Met|Ser|Gln|Ser|Pro|Ser|Ser|Leu|Pro|Val|Ser|Val|Gly| |
|1| | | |5| | | | |10| | | | |15| | |

|GAG|AAG|GTT|ACT|TTG|AGC|TGC|AAG|TCC|AGT|CAG|AGC|CTT|TTA|TAT|AGT|96|
|Glu|Lys|Val|Thr|Leu|Ser|Cys|Lys|Ser|Ser|Gln|Ser|Leu|Leu|Tyr|Ser| |
| | | | |20| | | | |25| | | | |30| | |

|GGT|AAT|CAA|AAG|AAC|TAC|TTG|GCC|TGG|TAC|CAG|CAG|AAA|CCA|GGG|CAG|144|
|Gly|Asn|Gln|Lys|Asn|Tyr|Leu|Ala|Trp|Tyr|Gln|Gln|Lys|Pro|Gly|Gln| |
| | | |35| | | | |40| | | | |45| | | |

|TCT|CCT|AAA|CTG|CTG|ATT|TAC|TGG|GCA|TCC|GCT|AGG|GAA|TCT|GGG|GTC|192|
|Ser|Pro|Lys|Leu|Leu|Ile|Tyr|Trp|Ala|Ser|Ala|Arg|Glu|Ser|Gly|Val| |
| |50| | | | |55| | | | |60| | | | | |

|CCT|GAT|CGC|TTC|ACA|GGC|AGT|GGA|TCT|GGG|ACA|GAT|TTC|ACT|CTC|TCC|240|
|Pro|Asp|Arg|Phe|Thr|Gly|Ser|Gly|Ser|Gly|Thr|Asp|Phe|Thr|Leu|Ser| |
|65| | | | |70| | | | |75| | | | |80| |

|ATC|AGC|AGT|GTG|AAG|ACT|GAA|GAC|CTG|GCA|GTT|TAT|TAC|TGT|CAG|CAG|288|
|Ile|Ser|Ser|Val|Lys|Thr|Glu|Asp|Leu|Ala|Val|Tyr|Tyr|Cys|Gln|Gln| |
| | | | |85| | | | |90| | | | |95| | |

|TAT|TAT|AGC|TAT|CCC|CTC|ACG|TTC|GGT|GCT|GGG|ACC|AAG|CTT|GTG|CTG|336|
|Tyr|Tyr|Ser|Tyr|Pro|Leu|Thr|Phe|Gly|Ala|Gly|Thr|Lys|Leu|Val|Leu| |
| | | |100| | | | |105| | | | |110| | | |

|AAA|GGC|TCT|ACT|TCC|GGT|AAA|CCA|TCT|GAA|GGT|AAA|GGT|GAA|GTT|AAA|384|
|Lys|Gly|Ser|Thr|Ser|Gly|Lys|Pro|Ser|Glu|Gly|Lys|Gly|Glu|Val|Lys| |
| | |115| | | | |120| | | | |125| | | | |

|CTG|GAT|GAG|ACT|GGA|GGA|GGC|TTG|GTG|CAA|CCT|GGG|AGG|CCC|ATG|AAA|432|
|Leu|Asp|Glu|Thr|Gly|Gly|Gly|Leu|Val|Gln|Pro|Gly|Arg|Pro|Met|Lys| |
| |130| | | | |135| | | | |140| | | | | |

|CTC|TCC|TGT|GTT|GCC|TCT|GGA|TTC|ACT|TTT|AGT|GAC|TAC|TGG|ATG|AAC|480|
|Leu|Ser|Cys|Val|Ala|Ser|Gly|Phe|Thr|Phe|Ser|Asp|Tyr|Trp|Met|Asn| |
|145| | | | |150| | | | |155| | | | |160| |

|TGG|GTC|CGC|CAG|TCT|CCA|GAG|AAA|GGA|CTG|GAG|TGG|GTA|GCA|CAA|ATT|528|
|Trp|Val|Arg|Gln|Ser|Pro|Glu|Lys|Gly|Leu|Glu|Trp|Val|Ala|Gln|Ile| |
| | | | |165| | | | |170| | | | |175| | |

|AGA|AAC|AAA|CCT|TAT|AAT|TAT|GAA|ACA|TAT|TAT|TCA|GAT|TCT|GTG|AAA|576|
|Arg|Asn|Lys|Pro|Tyr|Asn|Tyr|Glu|Thr|Tyr|Tyr|Ser|Asp|Ser|Val|Lys| |
| | | |180| | | | |185| | | | |190| | | |

|GGC|AGA|TTC|ACC|ATC|TCA|AGA|GAT|GAT|TCC|AAA|AGT|AGT|GTC|TAC|CTG|624|
|Gly|Arg|Phe|Thr|Ile|Ser|Arg|Asp|Asp|Ser|Lys|Ser|Ser|Val|Tyr|Leu| |
| | |195| | | | |200| | | | |205| | | | |

|CAA|ATG|AAC|AAC|TTA|AGA|GTT|GAA|GAC|ATG|GGT|ATC|TAT|TAC|TGT|ACG|672|
|Gln|Met|Asn|Asn|Leu|Arg|Val|Glu|Asp|Met|Gly|Ile|Tyr|Tyr|Cys|Thr| |
| |210| | | | |215| | | | |220| | | | | |

|GGT|TCT|TAC|TAT|GGT|ATG|GAC|TAC|TGG|GGT|CAA|GGA|ACC|TCA|GTC|ACC|720|
|Gly|Ser|Tyr|Tyr|Gly|Met|Asp|Tyr|Trp|Gly|Gln|Gly|Thr|Ser|Val|Thr| |
|225| | | | |230| | | | |235| | | | |240| |

|GTC|TCC|TAATAAGGAT|CC| | | | | | | | | | | | |738|
|Val|Ser| | | | | | | | | | | | | | | |

(2) INFORMATION FOR SEQ ID NO:23:

(i) SEQUENCE CHARACTERISTICS:
        (A) LENGTH: 242 amino acids
        (B) TYPE: amino acid
        (D) TOPOLOGY: linear (ii) MOLECULE TYPE: protein (xi) SEQUENCE DESCRIPTION: SEQ ID NO:23:

Asp Val Val Met Ser Gln Ser Pro Ser Ser Leu Pro Val Ser Val Gly
1               5                   10                  15

-continued

```
Glu Lys Val Thr Leu Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
            35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys Gly Ser Thr Ser Gly Lys Pro Ser Glu Gly Lys Gly Glu Val Lys
            115                 120                 125

Leu Asp Glu Thr Gly Gly Gly Leu Val Gln Pro Gly Arg Pro Met Lys
            130                 135                 140

Leu Ser Cys Val Ala Ser Gly Phe Thr Phe Ser Asp Tyr Trp Met Asn
145                 150                 155                 160

Trp Val Arg Gln Ser Pro Glu Lys Gly Leu Glu Trp Val Ala Gln Ile
            165                 170                 175

Arg Asn Lys Pro Tyr Asn Tyr Glu Thr Tyr Tyr Ser Asp Ser Val Lys
            180                 185                 190

Gly Arg Phe Thr Ile Ser Arg Asp Asp Ser Lys Ser Ser Val Tyr Leu
            195                 200                 205

Gln Met Asn Asn Leu Arg Val Glu Asp Met Gly Ile Tyr Tyr Cys Thr
            210                 215                 220

Gly Ser Tyr Tyr Gly Met Asp Tyr Trp Gly Gln Gly Thr Ser Val Thr
225                 230                 235                 240

Val Ser
```

MULTIVALENT ANTIGEN-BINDING PROTEINS

CROSS-REFERENCE TO RELATED APPLICATIONS

This application is a divisional of U.S. patent application Ser. No. 08/392,338, filed Feb. 22, 1995, issued as U.S. Pat. No. 5,869,620; which is a divisional of U.S. patent application Ser. No. 07/989,846, filed Nov. 20, 1992, now abandoned; which is a continuation-in-part of U.S. patent application Ser. No. 07/796,936, filed Nov. 25, 1991, now abandoned. The contents of each of the above mentioned applications are fully incorporated herein by reference.

This invention was made with Government Support under SBIR Grant 5R44 GM 39662-03 awarded by the National Institutes of Health, National Institute of General Medical Sciences. The Government has certain rights in the invention.

BACKGROUND OF THE INVENTION

1. Field of the Invention

The present invention relates generally to the production of antigen-binding molecules. More specifically, the invention relates to multivalent forms of antigen-binding proteins. Compositions of, genetic constructions for, methods of use, and methods for producing these multivalent antigen-binding proteins are disclosed.

2. Description of the Background Art

Antibodies are proteins generated by the immune system to provide a specific molecule capable of complexing with an invading molecule, termed an antigen. FIG. 14 shows the structure of a typical antibody molecule. Natural antibodies have two identical antigen-binding sites, both of which are specific to a particular antigen. The antibody molecule "recognizes" the antigen by complexing its antigen-binding sites with areas of the antigen termed epitopes. The epitopes fit into the conformational architecture of the antigen-binding sites of the antibody, enabling the antibody to bind to the antigen.

The antibody molecule is composed of two identical heavy and two identical light polypeptide chains, held together by interchain disulfide bonds (see FIG. 14). The remainder of this discussion will refer only to one light/heavy pair of chains, as each light/heavy pair is identical. Each individual light and heavy chain folds into regions of approximately 110 amino acids, assuming a conserved three-dimensional conformation. The light chain comprises one variable region (termed $V_L$) and one constant region ($C_L$), while the heavy chain comprises one variable region ($V_H$) and three constant regions ($C_H1$, $C_H2$ and $C_H3$). Pairs of regions associate to form discrete structures as shown in FIG. 14. In particular, the light and heavy chain variable regions, $V_L$ and $V_H$, associate to form an "$F_V$" area which contains the antigen-binding site.

The variable regions of both heavy and light chains show considerable variability in structure and amino acid composition from one antibody molecule to another, whereas the constant regions show little variability. The term "variable" as used in this specification refers to the diverse nature of the amino acid sequences of the antibody heavy and light chain variable regions. Each antibody recognizes and binds antigen through the binding site defined by the association of the heavy and light chain, variable regions into an $F_V$ area. The light-chain variable region $V_L$ and the heavy-chain variable region $V_H$ of a particular antibody molecule have specific amino acid sequences that allow the antigen-binding site to assume a conformation that binds to the antigen epitope recognized by that particular antibody.

Within the variable regions are found regions in which the amino acid sequence is extremely variable from one antibody to another. Three of these so-called "hypervariable" regions or "complementarity-determining regions" (CDR's) are found in each of the light and heavy chains. The three CDR's from a light chain and the three CDR's from a corresponding heavy chain form the antigen-binding site.

Cleavage of the naturally-occurring antibody molecule with the proteolytic enzyme papain generates fragments which retain their antigen-binding site. These fragments, commonly known as Fab's (for Fragment, antigen binding site) are composed of the $C_L$, $V_L$, $C_H1$ and $V_H$ regions of the antibody. In the Fab the light chain and the fragment of the heavy chain are covalently linked by a disulfide linkage.

Recent advances in immunobiology, recombinant DNA technology, and computer science have allowed the creation of single polypeptide chain molecules that bind antigen. These single-chain antigen-binding molecules incorporate a linker polypeptide to bridge the individual variable regions, $V_L$ and $V_H$, into a single polypeptide chain. A computer-assisted method for linker design is described more particularly in U.S. Pat. No. 4,704,692, issued to Ladner et al. in November, 1987, and incorporated herein by reference. A description of the theory and production of single-chain antigen-binding proteins is found in U.S. Pat. No. 4,946,778 (Ladner et al.), issued Aug. 7, 1990, and incorporated herein by reference. The single-chain antigen-binding proteins produced under the process recited in U.S. Pat. 4,946,778 have binding specificity and affinity substantially similar to that of the corresponding Fab fragment.

Bifunctional, or bispecific, antibodies have antigen binding sites of different specificities. Bispecific antibodies have been generated to deliver cells, cytotoxins, or drugs to specific sites. An important use has been to deliver host cytotoxic cells, such as natural killer or cytotoxic T cells, to specific cellular targets. (U. D. Staerz, O. Kanagawa, M. J. Bevan, Nature 314:628 (1985); S. Songilvilai, P. J. Lachmann, Clin. Exp. Immunol. 79: 315 (1990)). Another important use has been to deliver cytotoxic proteins to specific cellular targets. (V. Raso, T. Griffin, Cancer Res. 41:2073 (1981); S. Honda, Y. Ichimori, S. Iwasa, Cytotechnology 4:59 (1990)). Another important use has been to deliver anti-cancer non-protein drugs to specific cellular targets (J. Corvalan, W. Smith, V. Gore, Intl. J. Cancer Suppl. 2:22 (1988); M. Pimm et al., British J. of Cancer 61:508 (1990)). Such bispecific antibodies have been prepared by chemical cross-linking (M. Brennan et al., Science 229:81 (1985)), disulfide exchange, or the production of hybrid-hybridomas (quadromas). Quadromas are constructed by fusing hybridomas that secrete two different types of antibodies against two different antigens (Kurokawa, T. et al., Biotechnology 7.1163 (1989)).

SUMMARY OF THE INVENTION

This invention relates to the discovery that multivalent forms of single-chain antigen-binding proteins have significant utility beyond that of the monovalent single-chain antigen-binding proteins. A multivalent antigen-binding protein has more than one antigen-binding site. Enhanced binding activity, di- and multi-specific binding, and other novel uses of multivalent antigen-binding proteins have been demonstrated or are envisioned here. Accordingly, the invention is directed to multivalent forms of single-chain antigen-binding proteins, compositions of multivalent and single-chain antigen-binding proteins, methods of making and purifying multivalent forms of single-chain antigen-binding proteins, and uses for multivalent forms of single-chain antigen-binding proteins. The invention provides a multivalent antigen-binding protein comprising two or more single-chain protein molecules, each single-chain molecule comprising a first polypeptide comprising the binding portion of the variable region of an antibody heavy or light chain; a second polypeptide comprising the binding portion of the variable region of an antibody heavy or light chain; and a peptide linker linking the first and second polypeptides into a single-chain protein.

Also provided is a composition comprising a multivalent antigen-binding protein substantially free of single-chain molecules.

Also provided is an aqueous composition comprising an excess of multivalent antigen-binding protein over single-chain molecules.

A method of producing a multivalent antigen-binding protein is provided, comprising the steps of producing a composition comprising multivalent antigen-binding protein and single-chain molecules, each single-chain molecule comprising a first polypeptide comprising the binding portion of the variable region of an antibody heavy or light chain; a second polypeptide comprising the binding portion of the variable region of an antibody heavy or light chain; and a peptide linker linking the first and second polypeptides into a single-chain molecule; separating the multivalent protein from the single-chain molecules; and recovering the multivalent protein.

Also provided is a method of producing multivalent antigen-binding protein, comprising the steps of producing a composition comprising single-chain molecules as previously defined; dissociating the single-chain molecules; reassociating the single-chain molecules; separating the resulting multivalent antigen-binding proteins from the single-chain molecules; and recovering the multivalent proteins.

Also provided is another method of producing a multivalent antigen-binding protein, comprising the step of chemically cross-linking at least two single-chain antigen-binding molecules.

Also provided is another method of producing a multivalent antigen-binding protein, comprising the steps of producing a composition comprising single-chain molecules as previously defined; concentrating said single-chain molecules; separating said multivalent protein from said single-chain molecules; and finally recovering said multivalent protein.

Also provided is another method of producing a multivalent antigen-binding protein comprising two or more single-chain molecules, each single-chain molecule as previously defined, said method comprising: providing a genetic sequence coding for said single-chain molecule; transforming a host cell or cells with said sequence; expressing said sequence in said host or hosts; and recovering said multivalent protein.

Another aspect of the invention includes a method of detecting an antigen in or suspected of being in a sample, which comprises contacting said sample with the multivalent antigen-binding protein of claim 1 and detecting whether said multivalent antigen-binding protein has bound to said antigen.

Another aspect of the invention includes a method of imaging the internal structure of an animal, comprising administering to said animal an effective amount of a labeled form of the multivalent antigen-binding protein of claim 1 and measuring detectable radiation associated with said animal.

Another aspect of the invention includes a composition comprising an association of a multivalent antigen-binding protein with a therapeutically or diagnostically effective agent.

Another aspect of this invention is a single-chain protein comprising: a first polypeptide comprising the binding portion of the variable region of an antibody light chain; a second polypeptide comprising the binding portion of the variable region of an antibody light chain; a peptide linker linking said first and second polypeptides (a) and (b) into said single-chain protein.

Another aspect of the present invention includes the genetic constructions encoding the combinations of regions $V_L$—$V_L$ and $V_H$—$V_H$ for single-chain molecules, and encoding multivalent antigen-binding proteins.

Another part of this invention is a multivalent single-chain antigen-binding protein comprising: a first polypeptide comprising the binding portion of the variable region of an antibody heavy or light chain; a second polypeptide comprising the binding portion of the variable region of an antibody heavy or light chain; a peptide linker linking said first and second polypeptides (a) and (b) into said multivalent protein; a third polypeptide comprising the binding portion of the variable region of an antibody heavy or light chain; a fourth polypeptide comprising the binding portion of the variable region of an antibody heavy or light chain; a peptide linker linking said third and fourth polypeptides (d) and (e) into said multivalent protein; and a peptide linker linking said second and third polypeptides (b) and (d) into said multivalent protein. Also included are gentic constructions coding for this multivalent single-chain antigen-binding protein.

Also included are replicable cloning or expression vehicles including plasmids, hosts transformed with the aforementioned genetic sequences, and methods of producing multivalent proteins with the sequences, transformed hosts, and expression vehicles.

Methods of use are provided, such as a method of using the multivalent antigen-binding protein to diagnose a medical condition; a method of using the multivalent protein as a carrier to image the specific bodily organs of an animal; a therapeutic method of using the multivalent protein to treat a medical condition; and an immunotherapeutic method of conjugating a multivalent protein with a therapeutically or diagnostically effective agent. Also included are labelled multivalent proteins, improved immunoassays using them, and improved immunoaffinity purifications.

An advantage of using multivalent antigen-binding proteins instead of single-chain antigen-binding molecules or Fab fragments lies in the enhanced binding ability of the multivalent form. Enhanced binding occurs because the multivalent form has more binding sites per molecule. Another advantage of the present invention is the ability to use multivalent antigen-binding proteins as multi-specific binding molecules.

An advantage of using multivalent antigen-binding proteins instead of whole antibodies, is the enhanced clearing of the multivalent antigen-binding proteins from the serum due to their smaller size as compared to whole antibodies which may afford lower background in imaging applications. Multivalent antigen-binding proteins may penetrate solid tumors better than monoclonals, resulting in better tumor-fighting ability. Also, because they are smaller and lack the Fc component of intact antibodies, the multivalent antigen-binding proteins of the present invention may be less immunogenic than whole antibodies. The Fc component of whole antibodies also contains binding sites for liver, spleen and certain other cells and its absence should thus reduce accumulation in non-target tissues.

Another advantage of multivalent antigen-binding proteins is the ease with which they may be produced and engineered, as compared to the myeloma-fusing technique pioneered by Kohler and Milstein that is used to produce whole antibodies.

BRIEF DESCRIPTION OF THE DRAWINGS

The present invention as defined in the claims can be better understood with reference to the text and to the following drawings:

FIG. 5A depicts two single-chain protein molecules, the first having an anti-B $V_L$ and an anti-A $V_H$, and the second having an anti-A $V_L$ and an anti-B $V_H$. The figure shows the non-complementary nature of the $V_L$ and $V_H$ regions in each single-chain protein molecule.

FIG. 5B shows a hypothetical bispecific heterodivalent antigen-binding protein formed by rearrangement of the two single-chain proteins of FIG. 5A.

FIG. 5C depicts the hypothetical heterodivalent antigen-binding protein of FIG. 5B with different antigens A and B occupying their respective antigen-binding sites.

FIG. 10A is an amino acid (SEQ ID NO. 11) and nucleotide (SEQ ID NO. 10) sequence of the single-chain protein comprising the 4-4-20 $V_L$ region connected through the 212 linker polypeptide to the CC49 $V_H$ region.

FIG. 10B is an amino acid (SEQ ID NO. 13) and nucleotide (SEQ ID NO. 12) sequence of the single-chain protein comprising the CC49 $V_L$ region connected through the 212 linker polypeptide to the 4-4-20 $V_H$ region.

FIG. 15A is an amino acid (SEQ ID NO. 15) and nucleotide (SEQ ID NO. 14) sequence of the 4-4-20/212 single-chain antigen-binding protein with a single cysteine hinge.

FIG. 15B is an amino acid (SEQ ID NO. 17) and nucleotide (SEQ. ID NO. 16) sequence of the 4-4-20/212 single-chain antigen-binding protein with the two-cysteine hinge.

FIG. 16 shows the amino acid (SEQ ID NO. 19) and nucleotide (SEQ ID NO. 18) sequence of a divalent CC49/212 single-chain antigen-binding protein.

FIG. 19A is an amino acid (SEQ ID NO. 21) and nucleotide (SEQ ID NO. 20) sequence of the single-chain polypeptide comprising the 4-4-20 $V_L$ region connected through the 217 linker polypeptide to the CC49 $V_H$ region.

FIG. 19B is an amino acid (SEQ ID NO. 23) and nucleotide (SEQ ID NO. 22) sequence of the single-chain polypeptide comprising the CC49 $V_L$ region connected through the 217 linker polypeptide to the 4-4-20 $V_H$ region.

DETAILED DESCRIPTION OF THE PREFERRED EMBODIMENTS

Figure 1A:
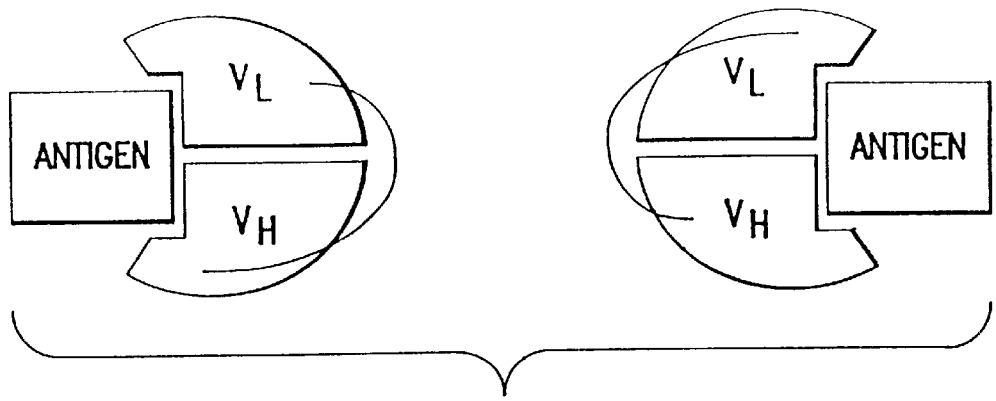
FIG. 1A is a schematic two-dimensional representation of two identical single-chain antigen-binding protein molecules, each comprising a variable light chain region ($V_L$), a variable heavy chain region ($V_H$), and a polypeptide linker joining the two regions. The single-chain antigen-binding protein molecules are shown binding antigen in their antigen-binding sites.

This invention relates to the discovery that multivalent forms of single-chain antigen-binding proteins have significant utility beyond that of the monovalent single-chain antigen-binding proteins. A multivalent antigen-binding protein has more than one antigen-binding site. For the purposes of this application, "valent" refers to the numerosity of antigen binding sites. Thus, a bivalent protein refers to a protein with two binding sites. Enhanced binding activity, bi- and multi-specific binding, and other novel uses of multivalent antigen-binding proteins have been demonstrated or are envisioned here. Accordingly, the invention is directed to multivalent forms of single-chain antigen-binding proteins, compositions of multivalent and single-chain antigen-binding proteins, methods of making and purifying multivalent forms of single-chain antigen-binding proteins, and new and improved uses for multivalent forms of single-chain antigen-binding proteins. The invention provides a multivalent antigen-binding protein comprising two or more single-chain protein molecules, each single-chain molecule comprising a first polypeptide comprising the binding portion of the variable region of an antibody heavy or light chain; a second polypeptide comprising the binding portion of the variable region of an antibody heavy or light chain; and a peptide linker linking the first and second polypeptides into a single-chain protein.

The term "multivalent" means any assemblage, covalently or non-covalently joined, of two or more single-chain proteins, the assemblage having more than one antigen-binding site. The single-chain proteins composing the assemblage may have antigen-binding activity, or they may lack antigen-binding activity individually but be capable of assembly into active multivalent antigen-binding proteins. The term "multivalent" encompasses bivalent, trivalent, tetravalent, etc. It is envisioned that multivalent forms above bivalent may be useful for certain applications.

A preferred form of the multivalent antigen-binding protein comprises bivalent proteins, including heterobivalent and homobivalent forms. The term "bivalent" means an assemblage of single-chain proteins associated with each other to form two antigen-binding sites. The term "heterobivalent" indicates multivalent antigen-binding proteins that are bispecific molecules capable of binding to two different antigenic determinants. Therefore, heterobivalent proteins have two antigen-binding sites that have different binding specificities. The term "homobivalent" indicates that the two binding sites are for the same antigenic determinant.

The terms "single-chain molecule" or "single-chain protein" are used interchangeably here. They are structurally defined as comprising the binding portion of a first polypeptide from the variable region of an antibody, associated with the binding portion of a second polypeptide from the variable region of an antibody, the two polypeptides being joined by a peptide linker linking the first and second polypeptides into a single polypeptide chain. The single polypeptide chain thus comprises a pair of variable regions connected by a polypeptide linker. The regions may associate to form a functional antigen-binding site, as in the case wherein the regions comprise a light-chain and a heavy-chain variable region pair with appropriately paired complementarity determining regions (CDRs). In this case, the single-chain protein is referred to as a "single-chain antigen-binding protein" or "single-chain antigen-binding molecule."

Alternatively, the variable regions may have unnaturally paired CDRs or may both be derived from the same kind of antibody chain, either heavy or light, in which case the resulting single-chain molecule may not display a functional antigen-binding site. The single-chain antigen-binding protein molecule is more fully described in U.S. Pat. No. 4,946,778 (Ladner et al.), and incorporated herein by reference.

Without being bound by any particular theory, the inventors speculate on several models which can equally explain the phenomenon of multivalence. The inventors' models are presented herein for the purpose of illustration only, and are not to be construed as limitations upon the scope of the invention. The invention is useful and operable regardless of the precise mechanism of multivalence.

Figure 1B:
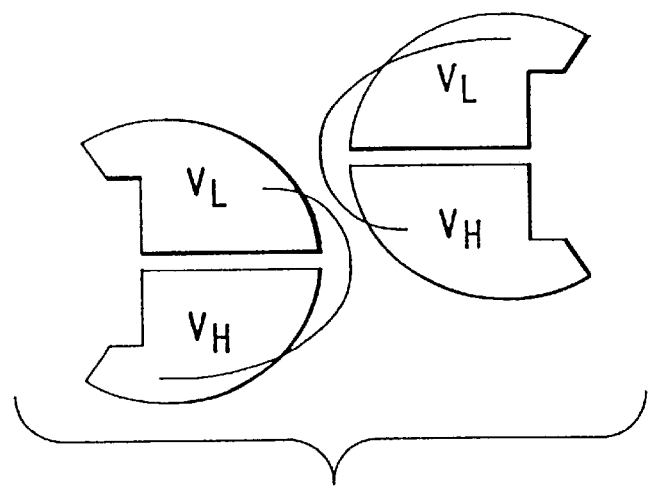
FIG. 1B depicts a hypothetical homodivalent antigen-binding protein formed by association of the polypeptide linkers of two monovalent single-chain antigen-binding proteins from FIG. 1A (the Association model). The divalent antigen-binding protein is formed by the concentration-driven association of two identical single-chain antigen-binding protein molecules.
Figure 1C:
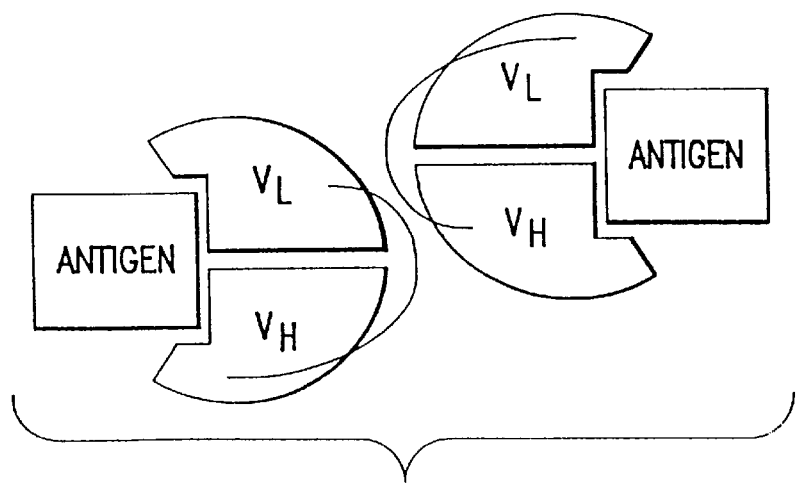
FIG. 1C depicts the hypothetical divalent protein of FIG. 1B with bound antigen molecules occupying both antigen-binding sites.

FIG. 1 depicts the first hypothetical model for the creation of a multivalent protein, the "Association" model. FIG. 1A shows two monovalent single-chain antigen-binding proteins, each composed of a $V_L$, a $V_H$, and a linker polypeptide covalently bridging the two. Each monovalent single-chain antigen-binding protein is depicted having an identical antigen-binding site containing antigen. FIG. 1B shows the simple association of the two single-chain antigen-binding proteins to create the bivalent form of the multivalent protein. It is hypothesized that simple hydrophobic forces between the monovalent proteins are responsible for their association in this manner. The origin of the multivalent proteins may be traceable to their concentration dependence. The monovalent units retain their original association between the $V_H$ and $V_L$ regions. FIG. 1C shows the newly-formed homobivalent protein binding two identical antigen molecules simultaneously. Homobivalent antigen-binding proteins are necessarily monospecific for antigen.

Figure 2A:
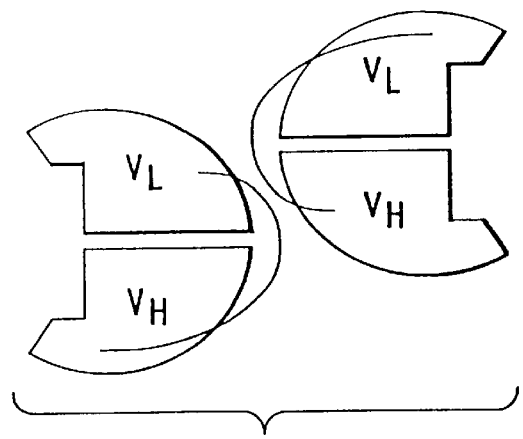
FIG. 2A depicts the hypothetical homodivalent protein of FIG. 1B.
Figure 2B:
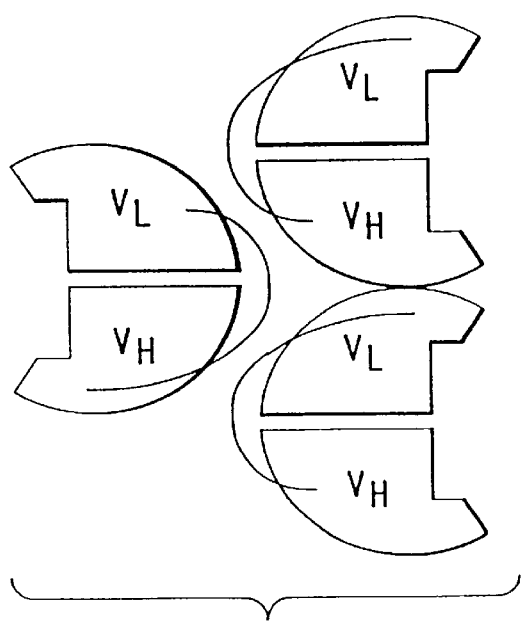
FIG. 2B depicts three single-chain antigen-binding protein molecules associated in a hypothetical trimer.
Figure 2C:
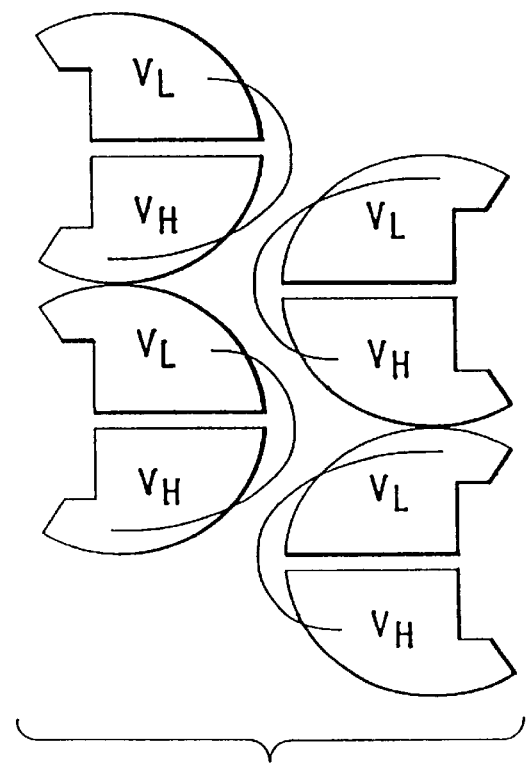
FIG. 2C depicts a hypothetical tetramer of four single-chain antigen-binding protein molecules.

Homovalent proteins are depicted in FIGS. 2A through 2C formed according to the Association model. FIG. 2A depicts a homobivalent protein, FIG. 2B a trivalent protein, and FIG. 2C a tetravalent protein. Of course, the limitations of two-dimensional images of three-dimensional objects must be taken into account. Thus, the actual spatial arrangement of multivalent proteins can be expected to vary somewhat from these figures.

Figure 3A:
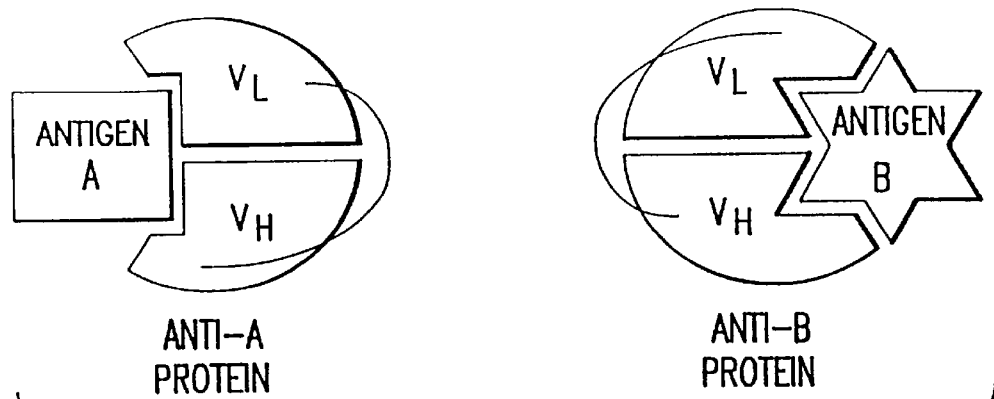
FIG. 3A depicts two separate and distinct monovalent single-chain antigen-binding proteins, Anti-A single-chain antigen-binding protein and Anti-B single-chain antigen-binding protein, with different antigen specificities, each individually binding either Antigen A or Antigen B.
Figure 3B:
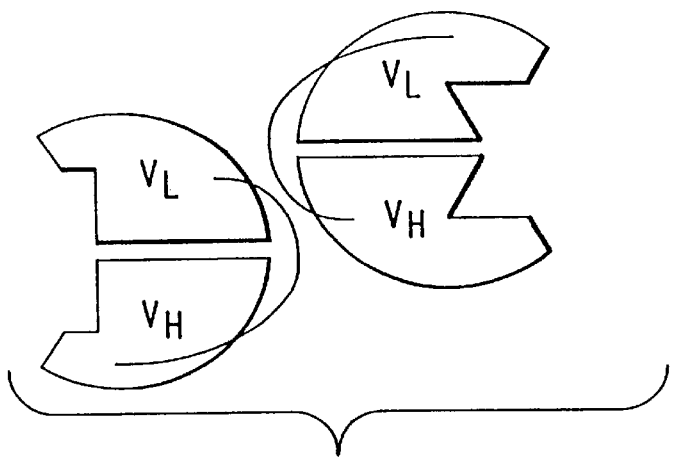
FIG. 3B depicts a hypothetical bispecific heterodivalent antigen-binding protein formed from the single-chain antigen-binding proteins of FIG. 3A according to the Association model.
Figure 3C:
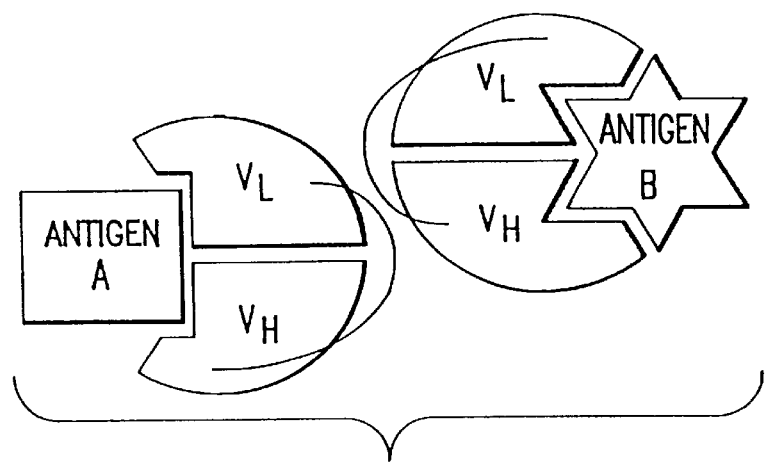
FIG. 3C depicts the hypothetical heterodivalent antigen-binding protein of FIG. 3B binding bispecifically, i.e., binding the two different antigens, A and B.

A heterobivalent antigen-binding protein has two different binding sites, the sites having different binding specificities. FIGS. 3A through C depict the Association model pathway to the creation of a heterobivalent protein. FIG. 3A shows two monovalent single-chain antigen-binding proteins, Anti-A single-chain antigen-binding protein and Anti-B single-chain antigen-binding protein, with antigen types A and B occupying the respective binding sites. FIG. 3B depicts the heterobivalent protein formed by the simple association of the original monovalent proteins. FIG. 3C shows the heterobivalent protein having bound antigens A and B into the antigen-binding sites. FIG. 3C therefore shows the heterobivalent protein binding in a bispecific manner.

Figure 4A:
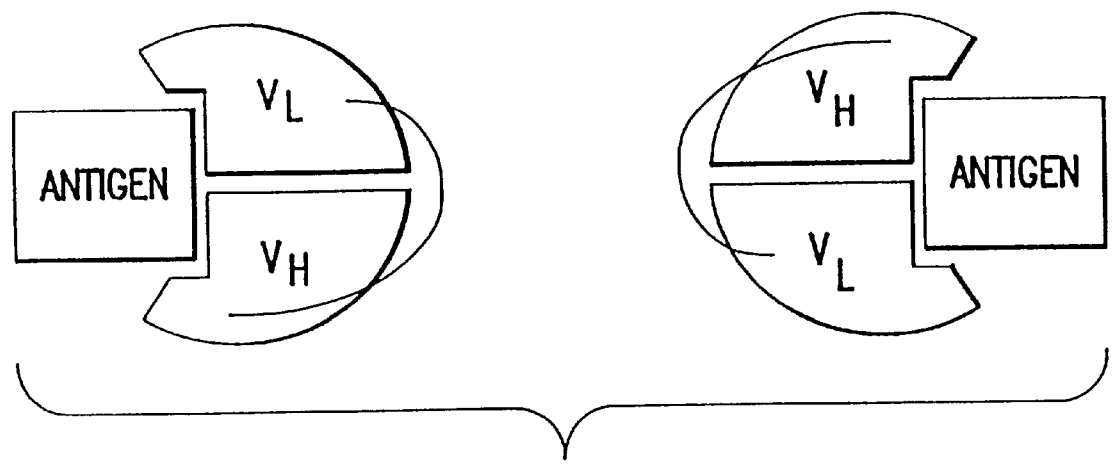
FIG. 4A depicts two identical single-chain antigen-binding protein molecules, each having a variable light chain region ($V_L$), a variable heavy chain region ($V_H$), and a polypeptide linker joining the two regions. The single-chain antigen-binding protein molecules are shown binding identical antigen molecules in their antigen-binding sites.
Figure 4B:
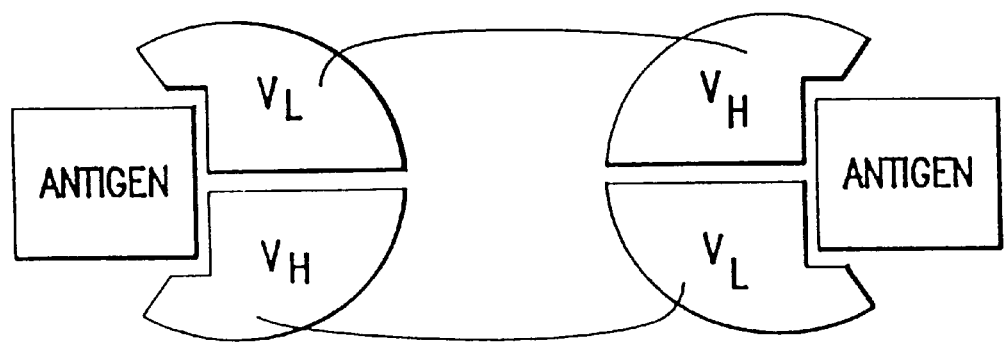
FIG. 4B depicts a hypothetical homodivalent protein formed by the rearrangement of the $V_L$ and $V_H$ regions shown in FIG. 4A (the Rearrangement model). Also shown is bound antigen.

An alternative model for the formation of multivalent antigen-binding proteins is shown in FIGS. 4 through 6. This "Rearrangement" model hypothesizes the dissociation of the variable region interface by contact with dissociating agents such as guanidine hydrochloride, urea, or alcohols such as ethanol, either alone or in combination. Combinations and relevant concentration ranges of dissociating agents are recited in the discussion concerning dissociating agents, and in Example 2. Subsequent re-association of dissociated regions allows variable region recombination differing from the starting single-chain proteins, as depicted in FIG. 4B. The homobivalent antigen-binding protein of FIG. 4B is formed from the parent single-chain antigen-binding proteins shown in FIG. 4A, the recombined bivalent protein having $V_L$ and $V_H$ from the parent monovalent single-chain proteins. The homobivalent protein of FIG. 4B is a fully functional monospecific bivalent protein, shown actively binding two antigen molecules.

Figure 6A:
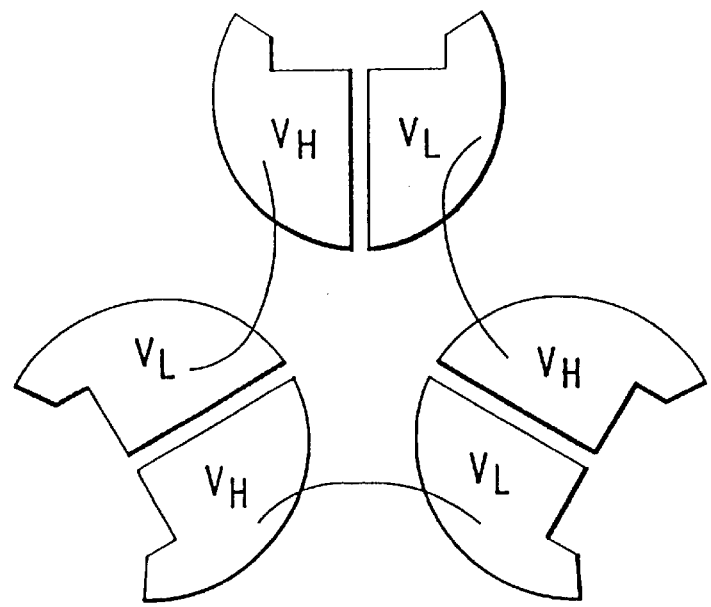
FIG. 6A is a schematic depiction of a hypothetical trivalent antigen-binding protein according to the Rearrangement model.
Figure 6B:
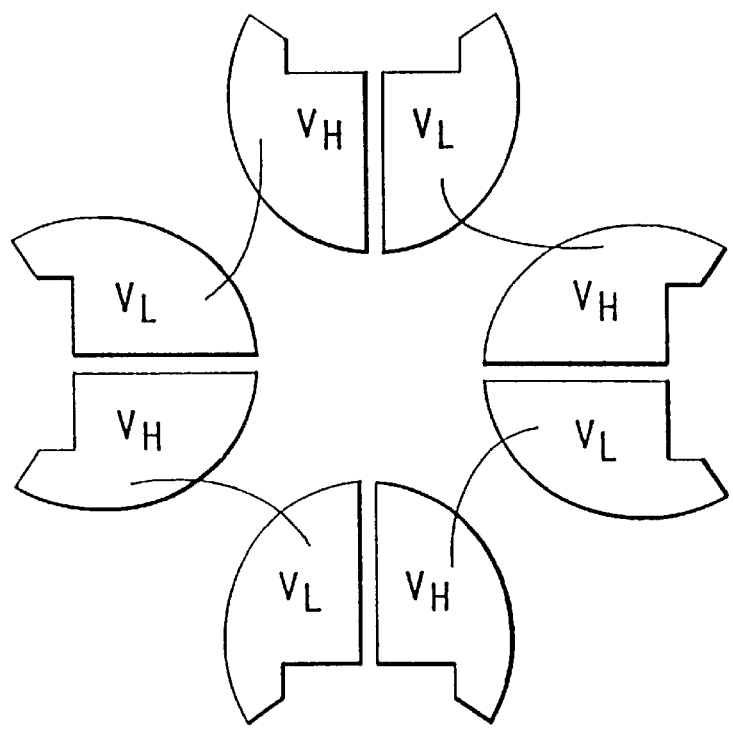
FIG. 6B is a schematic depiction of a hypothetical tetravalent antigen-binding protein according to the Rearrangement model.

FIGS. 5A–5C show the formation of heterobivalent antigen-binding proteins via the Rearrangement model. FIG. 5A shows a pair of single-chain proteins, each having a $V_L$ with complementarity determining regions (CDRs) that do not match those of the associated $V_H$. These single-chain proteins have reduced or no ability to bind antigen because of the mixed nature of their antigen-binding sites, and thus are made specifically to be assembled into multivalent proteins through this route. FIG. 5B shows the heterobivalent antigen-binding protein formed whereby the $V_H$ and $V_L$ regions of the parent proteins are shared between the separate halves of the heterobivalent protein. FIG. 5C shows the binding of two different antigen molecules to the resultant functional bispecific heterobivalent protein. The Rearrangement model also explains the generation of multivalent proteins of a higher order than bivalent, as it can be appreciated that more than a pair of single-chain proteins can be reassembled in this manner. These are depicted in FIGS. 6A and 6B.

One of the major utilities of the multivalent antigen-binding protein is in the heterobivalent form, in which one specificity is for one type of hapten or antigen, and the second specificity is for a second type of hapten or antigen. A multivalent molecule having two distinct binding specificities has many potential uses. For instance, one antigen binding site may be specific for a cell-surface epitope of a target cell, such as a tumor cell or other undesirable cell. The other antigen-binding site may be specific for a cell-surface epitope of an effector cell, such as the CD3 protein of a cytotoxic T-cell. In this way, the heterobivalent antigen-binding protein may guide a cytotoxic cell to a particular class of cells that are to be preferentially attacked.

Other uses of heterobivalent antigen-binding proteins are the specific targeting and destruction of blood clots by a bispecific molecule with specificity for tissue plasminogen activator (tPA) and fibrin; the specific targeting of pro-drug activating enzymes to tumor cells by a bispecific molecule with specificity for tumor cells and enzyme; and specific targeting of cytotoxic proteins to tumor cells by a bispecific molecule with specificity for tumor cells and a cytotoxic protein. This list is illustrative only, and any use for which a multivalent specificity is appropriate comes within the scope of this invention.

The invention also extends to uses for the multivalent antigen-binding proteins in purification and biosensors.

Affinity purification is made possible by affixing the multivalent antigen-binding protein to a support, with the antigen-binding sites exposed to and in contact with the ligand molecule to be separated, and thus purified. Biosensors generate a detectable signal upon binding of a specific antigen to an antigen-binding molecule, with subsequent processing of the signal. Multivalent antigen-binding proteins, when used as the antigen-binding molecule in biosensors, may change conformation upon binding, thus generating a signal that may be detected.

Essentially all of the uses for which monoclonal or polyclonal antibodies, or fragments thereof, have been envisioned by the prior art, can be addressed by the multivalent proteins of the present invention. These uses include detectably-labelled forms of the multivalent protein. Types of labels are well-known to those of ordinary skill in the art. They include radiolabelling, chemiluminescent labeling, fluorochromic labelling, and chromophoric labeling. Other uses include imaging the internal structure of an animal (including a human) by administering an effective amount of a labelled form of the multivalent protein and measuring detectable radiation associated with the animal. They also include improved immunoassays, including sandwich immunoassay, competitive immunoassay, and other immunoassays wherein the labelled antibody can be replaced by the multivalent antigen-binding protein of this invention.

A first preferred method of producing multivalent antigen-binding proteins involves separating the multivalent proteins from a production composition that comprises both multivalent and single-chain proteins, as represented in Example 1. The method comprises producing a composition of multivalent and single-chain proteins, separating the multivalent proteins from the single-chain proteins, and recovering the multivalent proteins.

A second preferred method of producing multivalent antigen-binding proteins comprises the steps of producing single-chain protein molecules, dissociating said single-chain molecules, reassociating the single-chain molecules such that a significant fraction of the resulting composition includes multivalent forms of the single-chain antigen-binding proteins, separating multivalent antigen-binding proteins from single-chain molecules, and recovering the multivalent proteins. This process is illustrated with more detail in Example 2. For the purposes of this method, the term "producing a composition comprising single-chain molecules" may indicate the actual production of these molecules. The term may also include procuring them from whatever commercial or institutional source makes them available. Use of the term "producing single-chain proteins" means production of single-chain proteins by any process, but preferably according to the process set forth in U.S. Pat. No. 4,946,778 (Ladner et al.). Briefly, that patent pertains to a single polypeptide chain antigen-binding molecule which has binding specificity and affinity substantially similar to the binding specificity and affinity of the aggregate light and heavy chain variable regions of an antibody, to genetic sequences coding therefore, and to recombinant DNA methods of producing such molecules, and uses for such molecules. The single-chain protein produced by the Ladner et al. methodology comprises two regions linked by a linker polypeptide. The two regions are termed the $V_H$ and $V_L$ regions, each region comprising one half of a functional antigen-binding site.

The term "dissociating said single-chain molecules" means to cause the physical separation of the two variable regions of the single-chain protein without causing denaturation of the variable regions. "Dissociating agents" are defined herein to include all agents capable of dissociating the variable regions, as defined above. In the context of this invention, the term includes the well-known agents alcohol (including ethanol), guanidine hydrochloride (GuHCl), and urea. Others will be apparent to those of ordinary skill in the art, including detergents and similar agents capable of interrupting the interactions that maintain protein conformation. In the preferred embodiment, a combination of GuHCl and ethanol (EtOH) is used as the dissociating agent. A preferred range for ethanol and GuHCl is from 0 to 50% EtOH, vol/vol, 0 to 2.0 moles per liter (M) GuHCl. A more preferred range is from 10–30% EtOH and 0.5–1.0 M GuHCl, and a most preferred range is 20% EtOH, 0.5 M GuHCl. A preferred dissociation buffer contains 0.5 M guanidine hydrochloride, 20% ethanol, 0.05 M TRIS, and 0.01 M $CaCl_2$, pH 8.0.

Use of the term "re-associating said single-chain molecules" is meant to describe the reassociation of the variable regions by contacting them with a buffer solution that allows reassociation. Such a buffer is preferably used in the present invention and is characterized as being composed of 0.04 M MOPS, 0.10 M calcium acetate, pH 7.5. Other buffers allowing the reassociation of the $V_L$ and $V_H$ regions are well within the expertise of one of ordinary skill in the art.

The separation of the multivalent protein from the single-chain molecules occurs by use of standard techniques known in the art, particularly including cation exchange or gel filtration chromatography.

Figure 7:
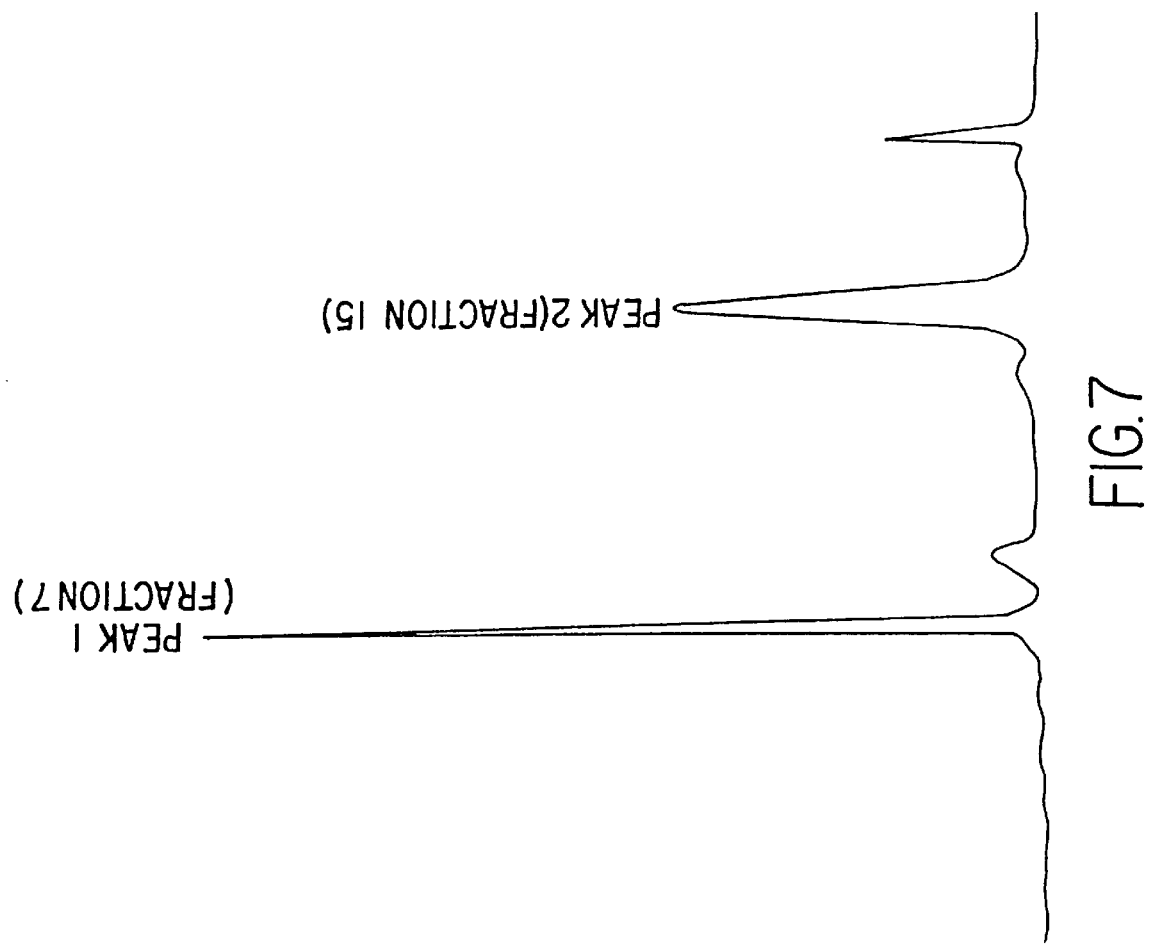
FIG. 7 is a chromatogram depicting the separation of CC49/212 antigen-binding protein monomer from dimer on a cation exchange high performance liquid chromatographic column. The column is a PolyCAT A aspartic acid column (Poly WC, Columbia, Md.). Monomer is shown as Peak 1, eluting at 27.32 min., and dimer is shown as Peak 2, eluting at 55.52 min.

Cation exchange chromatography is the general liquid chromatographic technique of ion-exchange chromatography utilizing anion columns well-known to those of ordinary skill in the art. In this invention, the cations exchanged are the single-chain and multivalent protein molecules. Since multivalent proteins will have some multiple of the net charge of the single-chain molecule, the multivalent proteins are retained more strongly and are thus separated from the single-chain molecules. The preferred cationic exchanger of the present invention is a polyaspartic acid column, as shown in FIG. 7. FIG. 7 depicts the separation of single-chain protein (Peak 1, 27.32 min.) from bivalent protein (Peak 2, 55.54 min.) Those of ordinary skill in the art will realize that the invention is not limited to any particular type of chromatography column, so long as it is capable of separating the two forms of protein molecules.

Figure 8:
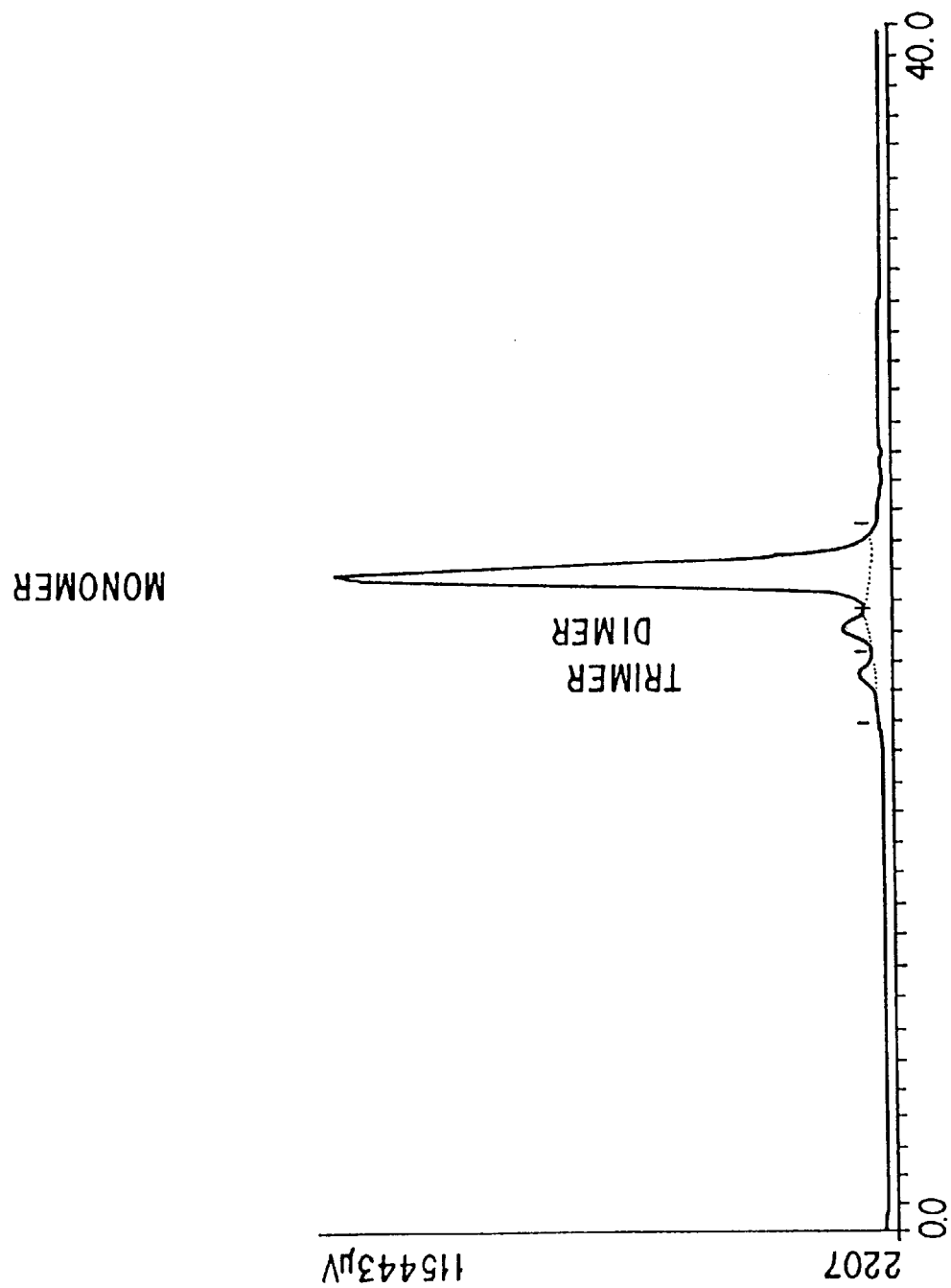
FIG. 8 is a chromatogram of the purified monomer from FIG. 7. Monomer elutes at 21.94 min., preceded by dimer (20.135 min.) and trimer (18.640 min.). Gel filtration column, Protein-Pak 300SW (Waters Associates, Milford, Mass.).

Gel filtration chromatography is the use of a gel-like material to separate proteins on the basis of their molecular weight. A "gel" is a matrix of water and a polymer, such as agarose or polymerized acrylamide. The present invention encompasses the use of gel filtration HPLC (high performance liquid chromatography), as will be appreciated by one of ordinary skill in the art. FIG. 8 is a chromatogram depicting the use of a Waters Associates' Protein-Pak 300 SW gel filtration column to separate monovalent single-chain protein from multivalent protein, including the monomer (21.940 min.), bivalent protein (20.135 min.), and trivalent protein (18.640 min.).

Recovering the multivalent antigen-binding proteins is accomplished by standard collection procedures well known in the chemical and biochemical arts. In the context of the present invention recovering the multivalent protein preferably comprises collection of eluate fractions containing the peak of interest from either the cation exchange column, or the gel filtration HPLC column. Manual and automated fraction collection are well-known to one of ordinary skill in the art. Subsequent processing may involve lyophilization of the eluate to produce a stable solid, or further purification.

A third preferred method of producing multivalent antigen-binding proteins is to start with purified single-chain proteins at a lower concentration, and then increase the concentration until some significant fraction of multivalent proteins is formed. The multivalent proteins are then separated and recovered. The concentrations conducive to formation of multivalent proteins in this manner are from about 0.5 milligram per milliliter (mg/ml) to the concentration at which precipitates begin to form.

The use of the term "substantially free" when used to describe a composition of multivalent and single-chain antigen-binding protein molecules means the lack of a significant peak corresponding to the single-chain molecule, when the composition is analyzed by cation exchange chromatography, as disclosed in Example 1 or by gel filtration chromatography as disclosed in Example 2.

By use of the term "aqueous composition" is meant any composition of single-chain molecules and multivalent proteins including a portion of water. In the same context, the phrase "an excess of multivalent antigen-binding protein over single-chain molecules" indicates that the composition comprises more than 50% of multivalent antigen-binding protein.

The use of the term "cross-linking" refers to chemical means by which one can produce multivalent antigen-binding proteins from monovalent single-chain protein molecules. For example, the incorporation of a cross-linkable sulfhydryl chemical group as a cysteine residue in the single-chain proteins allows cross-linking by mild reduction of the sulfhydryl group. Both monospecific and multispecific multivalent proteins can be produced from single-chain proteins by cross-linking the free cysteine groups from two or more single-chain proteins, causing a covalent chemical linkage to form between the individual proteins. Free cysteines have been engineered into the C-terminal portion of the 4-4-20/212 single-chain antigen-binding protein, as discussed in Example 5 and Example 8. These free cysteines may then be cross-linked to form multivalent antigen-binding proteins.

The invention also comprises single-chain proteins, comprising: (a) a first polypeptide comprising the binding portion of the variable region of an antibody light chain; (b) a second polypeptide comprising the binding portion of the variable region of an antibody light chain; and (c) a peptide linker linking said first and second polypeptides (a) and (b) into said single-chain protein. A similar single-chain protein comprising the heavy chain variable regions is also a part of this invention. Genetic sequences encoding these molecules are also included in the scope of this invention. Since these proteins are comprised of two similar variable regions, they do not necessarily have any antigen-binding capability.

The invention also includes a DNA sequence encoding a bispecific bivalent antigen-binding protein. Example 4 and Example 7 discusses in detail the sequences that appear in FIGS. 10A and 10B that allow one of ordinary skill to construct a heterobivalent antigen-binding molecule. FIG. 10A is an amino acid and nucleotide sequence listing of the single-chain protein comprising the 4-4-20 $V_L$ region connected through the 212 linker polypeptide to the CC49 $V_H$ region. FIGS. 10B is a similar listing of the single-chain protein comprising the CC49 $V_L$ region connected through the 212 linker polypeptide to the 44-20 $V_H$ region. Subjecting a composition including these single-chain molecules to dissociating and subsequent re-associating conditions results in the production of a bivalent protein with two different binding specificities.

Synthesis of DNA sequences is well known in the art, and possible through at least two routes. First, it is well-known that DNA sequences may be synthesized through the use of automated DNA synthesizers de novo, once the primary sequence information is known. Alternatively, it is possible to obtain a DNA sequence coding for a multivalent single-chain antigen-binding protein by removing the stop codons from the end of a gene encoding a single-chain antigen-binding protein, and then inserting a linker and a gene encoding a second single-chain antigen-binding protein. Example 6 demonstrates the construction of a DNA sequence coding for a bivalent single-chain antigen-binding protein. Other methods of genetically constructing multivalent single-chain antigen-binding proteins come within the spirit and scope of the present invention.

Having now generally described this invention the same will better be understood by reference to certain specific examples which are included for purposes of illustration and are not intended to limit it unless otherwise specified.

EXAMPLE 1

Production of Multivalent Antigen-Binding Proteins During Purification

In the production of multivalent antigen-binding proteins, the same recombinant *E. coli* production system that was used for prior single-chain antigen-binding protein production was used. See Bird, et al., *Science* 242:423 (1988). This production system produced between 2 and 20% of the total *E. coli* protein as antigen-binding protein. For protein recovery, the frozen cell paste from three 10-liter fermentations (600–900 g) was thawed overnight at 4° C. and gently resuspended at 4° C. in 50 mM Tris-Hcl, 1.0 mM EDTA, 100 mM KCl, 0.1 mM PMSF, pH 8.0 (lysis buffer), using 10 liters of lysis buffer for every kilogram of wet cell paste. When thoroughly resuspended, the chilled mixture was passed three times through a Manton-Gaulin cell homogenizer to totally lyse the cells. Because the cell homogenizer raised the temperature of the cell lysate to 25±5° C., the cell lysate was cooled to 5±2° C. with a Lauda/Brinkman chilling coil after each pass. Complete lysis was verified by visual inspection under a microscope.

The cell lysate was centrifuged at 24,300 g for 30 min. at 6° C. using a Sorvall RC-5B centrifuge. The pellet containing the insoluble antigen-binding protein was retained, and the supernatant was discarded. The pellet was washed by gently scraping it from the centrifuge bottles and resuspending it in 5 liters of lysis buffer/kg of wet cell paste. The resulting 3.0- to 4.5-liter suspension was again centrifuged at 24,300 g for 30 min at 6° C., and the supernatant was discarded. This washing of the pellet removes soluble *E. coli* proteins and can be repeated as many as five times. At any time during this washing procedure the material can be stored as a frozen pellet at −20° C. A substantial time saving in the washing steps can be accomplished by utilizing a Pellicon tangential flow apparatus equipped with 0.22-$\mu$m microporous filters, in place of centrifugation.

The washed pellet was solubilized at 4° C. in freshly prepared 6 M guanidine hydrochloride, 50 mM Tris-HCl, 10 mM $CaCl_2$, 50 mM KCl, pH 8.0 (dissociating buffer), using 9 ml/g of pellet. If necessary, a few quick pulses from a Heat Systems Ultrasonics tissue homogenizer can be used to complete the solubilization. The resulting suspension was centrifuged at 24,300 g for 45 min at 6° C. and the pellet was discarded. The optical density of the supernatant was determined at 280 nm and if the $OD_{280}$ was above 30, additional dissociating buffer was added to obtain an OD280 of approximately 25.

The supernatant was slowly diluted into cold (4–7° C.) refolding buffer (50 mM Tris-HCl, 10 mM $CaCl_2$, 50 mM KCl, pH 8.0) until a 1:10 dilution was reached (final volume 10–20 liters). Re-folding occurs over approximately eighteen hours under these conditions. The best results are obtained when the GuHCl extract is slowly added to the refolding buffer over a 2-h period, with gentle mixing. The solution was left undisturbed for at least a 20-h period, and 95% ethanol was added to this solution such that the final ethanol concentration was approximately 20%. This solution was left undisturbed until the flocculated material settled to the bottom, usually not less than sixty minutes. The solution was filtered through a 0.2 um Millipore Millipak 200. This filtration step may be optionally preceded by a centrifugation step. The filtrate was concentrated to 1 to 2 liters using an Amicon spiral cartridge with a 10,000 MWCO cartridge, again at 4° C.

The concentrated crude antigen-binding protein sample was dialyzed against Buffer A (60 mM MOPS, 0.5 mM Ca acetate, pH 6.0–6.4) until the conductivity was lowered to that of Buffer A. The sample was then loaded on a 21.5× 250-mm polyaspartic acid PolyCAT A column, manufactured by Poly LC of Columbia, Md. If more than 60 mg of protein is loaded on this column, the resolution begins to deteriorate; thus, the concentrated crude sample often must be divided into several PolyCAT A runs. Most antigen-binding proteins have an extinction coefficient of about 2.0 ml mg$^{-1}$ cm$^{-1}$ at 280 nm and this can be used to determine protein concentration. The antigen-binding protein sample was eluted from the PolyCAT A column with a 50-min linear gradient from Buffer A to Buffer B (see Table 1). Most of the single-chain proteins elute between 20 and 26 minutes when this gradient is used. This corresponds to an eluting solvent composition of approximately 70% Buffer A and 30% Buffer B. Most of the bivalent antigen-binding proteins elute later than 45 minutes, which correspond to over 90% Buffer B.

FIG. 7 is a chromatogram depicting the separation of single-chain protein from bivalent CC49/212 protein, using the cation-exchange method just described. Peak 1, 27.32 minutes, represents the monomeric single-chain fraction. Peak 2, 55.52 minutes, represents the bivalent protein fraction.

Figure 9:
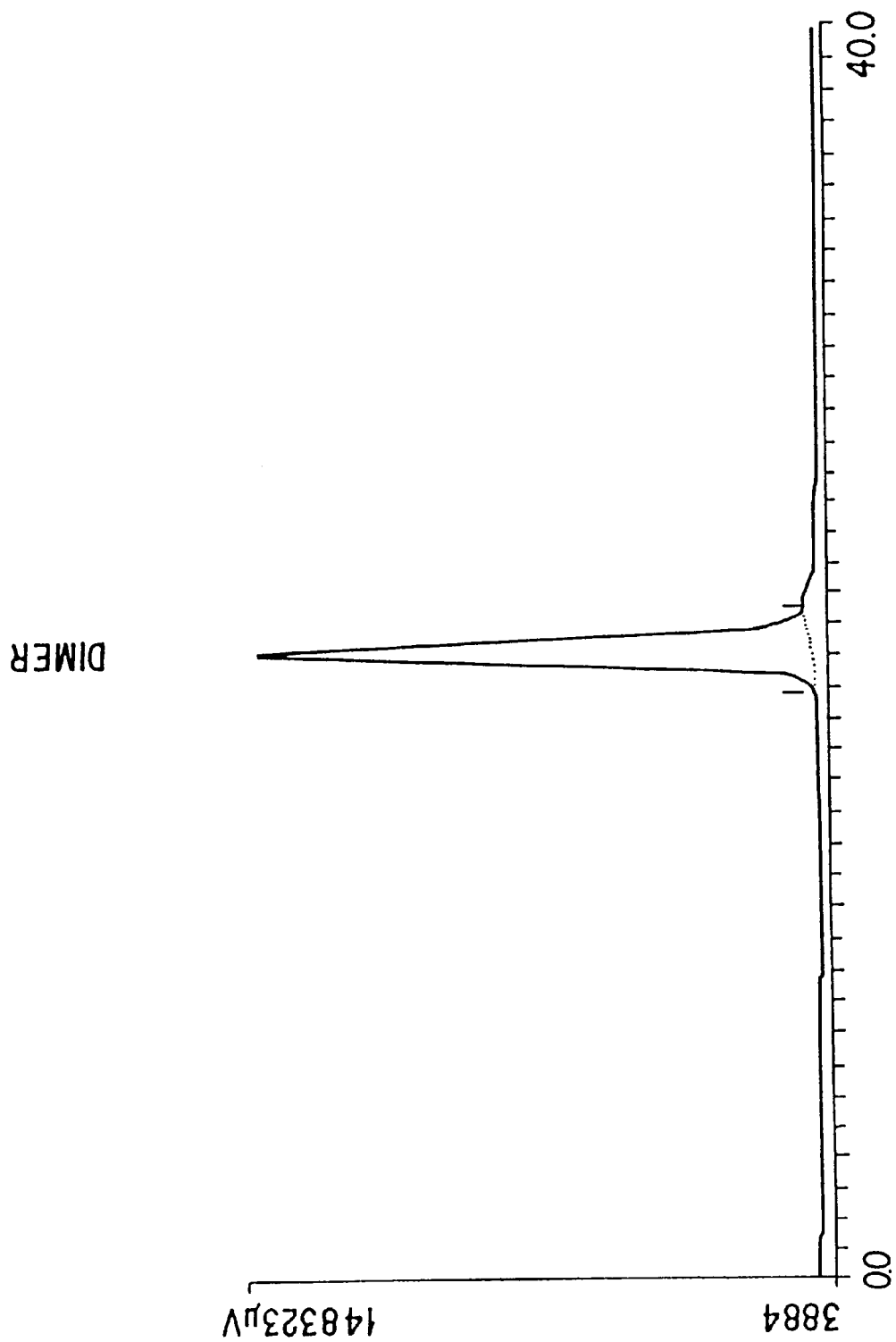
FIG. 9 is a similar chromatogram of purified dimer (20.14 min.) from FIG. 7, run on the gel filtration HPLC column of FIG. 8.

FIG. 8 is a chromatogram of the purified monomeric single-chain antigen-binding protein CC49/212 (Fraction 7 from FIG. 7) run on a Waters Protein-Pak 300SW gel filtration column. Monomer, with minor contaminates of dimer and trimer, is shown. FIG. 9 is a chromatogram of the purified bivalent antigen-binding protein CC49/212 (Fraction 15 from FIG. 7) run on the same Waters Protein-Pak 300SW gel filtration column as used in FIG. 8.

TABLE 1

PolyCAT A Cation-Exchange HPLC Gradients

| Time (min)[a] | Flow (ml/min) | Buffers[b] | | |
|---|---|---|---|---|
| | | A | B | C |
| Initial | 15.0 | 100 | 0 | 0 |
| 50.0 | 15.0 | 0 | 100 | 0 |
| 55.0 | 15.0 | 0 | 100 | 0 |
| 60.0 | 15.0 | 0 | 0 | 100 |
| 63.0 | 15.0 | 0 | 0 | 100 |
| 64.0 | 15.0 | 100 | 0 | 0 |
| 67.0 | 15.0 | 100 | 0 | 0 |

[a]Linear gradients are run between each time point.
[b]Buffer A, 60 mM MOPS, 0.5 mM Ca acetate, pH 6.0–6.4;
Buffer B, 60 mM MOPS, 20 mM Ca acetate, pH 7.5–8.0;
Buffer C, 40 mM MOPS, 100 mM CaCl$_2$, pH 7.5.

This purification procedure yielded multivalent antigen-binding proteins that are more than 95% pure as examined by SDS-PAGE and size exclusion HPLC. Modifications of the above procedure may be dictated by the isoelectric point of the particular multivalent antigen-binding protein being purified. Of the monomeric single-chain proteins that have been purified to date, all have had an isoelectric point (pI) between 8.0 and 9.5. However, it is possible that a multivalent antigen-binding protein may be produced with a pI of less than 7.0. In that case, an anion exchange column may be required for purification.

The CC49 monoclonal antibody was developed by Dr. Jeffrey Schlom's group, Laboratory of Tumor Immunology and Biology, National Cancer Institute. It binds specifically to the pan-carcinoma tumor antigen TAG-72. See Muraro, R. et al., *Cancer Research* 48:4588–4596 (1988). A hybridoma which produces the CC49 monoclonal antibody has been deposited with the American Type Culture Collection (ATCC), 12301 Parklawn Drive, Rockville, Md. and assigned ATCC Accession No. HB-9459.

Figure 18:
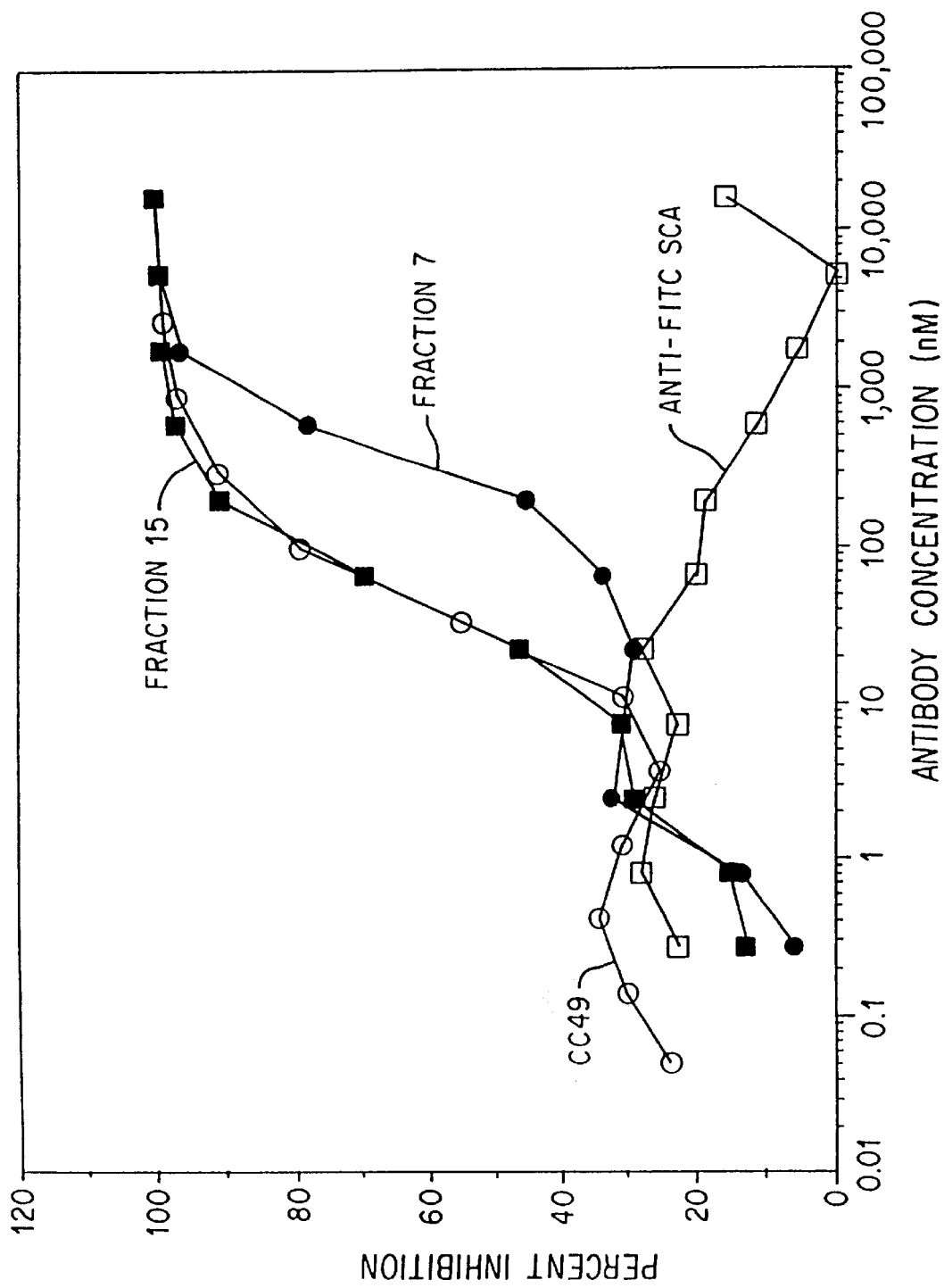
FIG. 18 is a graphical representation of four competition radioimmunoassays (RIA) in which unlabeled CC49 IgG (open circles) CC49/212 single-chain antigen-binding protein (closed circles) and CC49/212 divalent antigen-binding protein (closed squares) and anti-fluorescein 4-4-20/212 single-chain antigen-binding protein (open squares) competed against a CC49 IgG radiolabeled with $^{125}$I for binding to the TAG-72 antigen on a human breast carcinoma extract.

To determine the binding properties of the bivalent and monomeric CC49/212 antigen-binding proteins, a competition radioimmunoassay (RIA) was set up in which a CC49 IgG (with two antigen binding sites) radiolabeled with $^{125}$I was competed against unlabeled CC49 IgG, or monovalent (fraction 7 in FIG. 7) or bivalent (fraction 15 in FIG. 7) CC49/212 antigen-binding protein for binding to the TAG-72 antigen on a human breast carcinoma extract. (See FIG. 18). This competition RIA showed that the bivalent antigen-binding protein competed equally well for the antigen as did IgG, whereas the monovalent single-chain antigen-binding protein needed a ten-fold higher protein concentration to displace the IgG. Thus, the monovalent antigen-binding protein competes with about a ten-fold lower affinity for the antigen than does the bivalent IgG or bivalent antigen-binding protein. FIG. 18 also shows the result of the competition RIA of a non-TAG-72 specific single-chain antigen-binding protein, the antifluorescein 4-4-20/212, which does not compete for binding.

EXAMPLE 2

Process of Making Multivalent Antigen-Binding Proteins Using Dissociating Agents A. Process Using Guanidine HCl and Ethanol Multivalent antigen-binding proteins were produced from purified single-chain proteins in the following way. First the purified single-chain protein at a concentration of 0.25–4 mg/ml was dialyzed against 0.5 moles/liter (M) guanidine hydrochloride (GuHCl), 20% ethanol (EtOH), in 0.05 M TRIS, 0.05 M KCl, 0.01 M CaCl$_2$ buffer pH 8.0. This combination of dissociating agents is thought to disrupt the $V_L/V_H$ interface, allowing the $V_H$ of a first single-chain molecule to come into contact with a $V_L$ from a second single-chain molecule. Other dissociating agents such as urea, and alcohols such as isopropanol or methanol should be substitutable for GuHCl and EtOH. Following the initial dialysis, the protein was dialyzed against the load buffer for the final HPLC purification step. Two separate purification protocols, cation exchange and gel filtration chromatography, can be used to separate the single-chain protein monomer from the multivalent antigen-binding proteins. In the first method, monomeric and multivalent antigen-binding proteins were separated by using cation exchange HPLC chromography, using a polyaspartate column (PolyCAT A). This was a similar procedure to that used in the final purification of the antigen-binding proteins as described in Example 1. The load buffer was 0.06 M MOPS, 0.001 M Calcium Acetate pH 6.4. In the second method, the monomeric and multivalent antigen-binding proteins were separated by gel filtration HPLC chromatography using as a load buffer 0.04 M MOPS, 0.10 M Calcium Acetate pH 7.5. Gel filtration chromatography separates proteins based on their molecular size.

Figure 11:
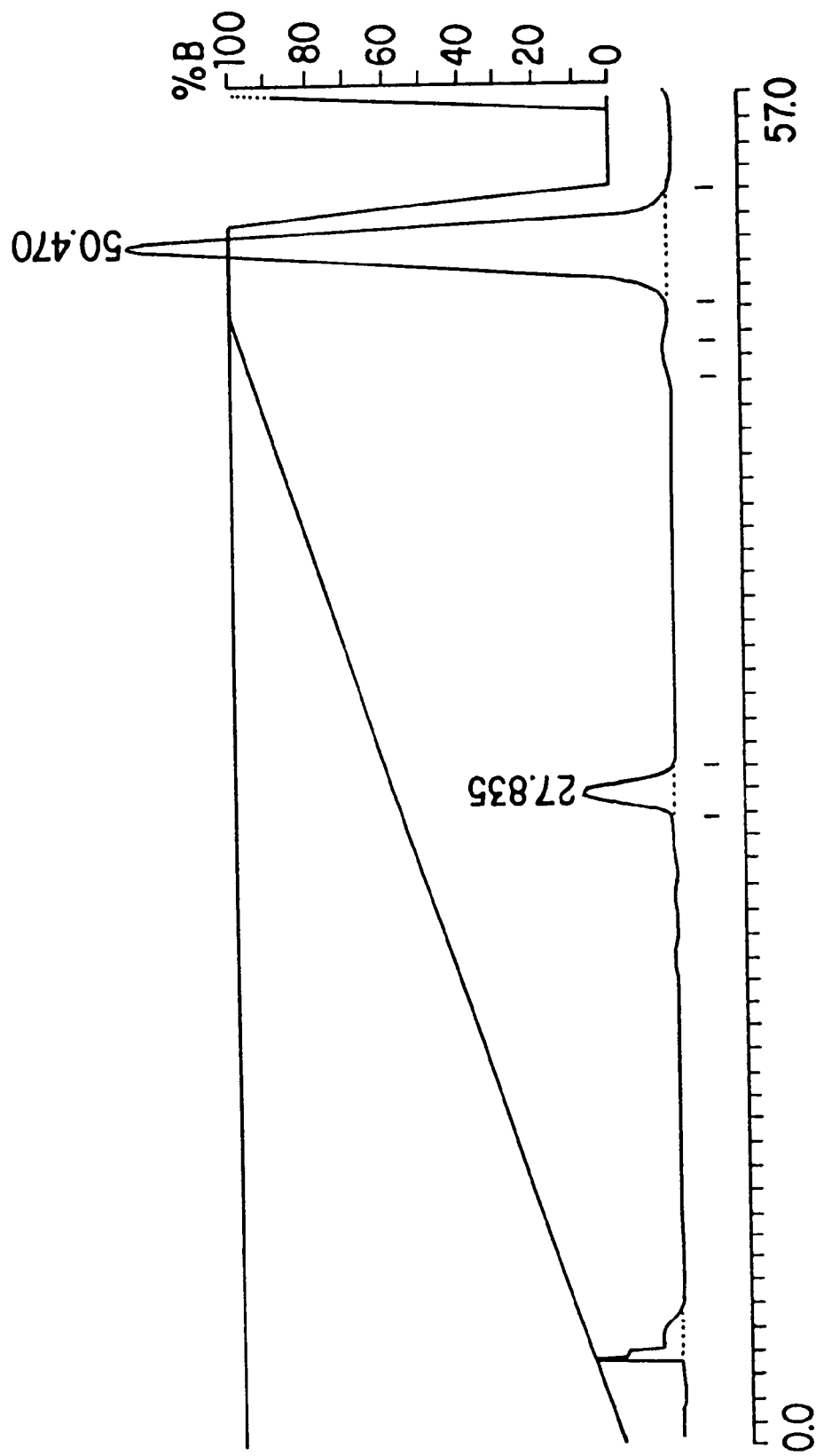
FIG. 11 is a chromatogram depicting the separation of the monomer (27.83 min.) and dimer (50.47 min.) forms of the CC49/212 antigen-binding protein by cation exchange, on a PolyCAT A cation exchange column (Poly LC, Columbia, Md.).

Once the antigen-binding protein sample was loaded on the cation exchange HPLC column, a linear gradient was run between the load buffer (0.04 to 0.06 M MOPS, 0.000 to 0.001 M calcium acetate, 0 to 10% glycerol pH 6.0–6.4) and a second buffer (0.04 to 0.06 M MOPS, 0.01 to 0.02 M calcium acetate, 0 to 10% glycerol pH 7.5). It was important to have extensively dialyze the antigen-binding protein sample before loading it on the column. Normally, the conductivity of the sample is monitored against the dialysis buffer. Dialysis is continued until the conductivity drops below 600 $\mu$S. FIG. 11 shows the separation of the monomeric (27.83 min.) and bivalent (50.47 min.) forms of the CC49/212 antigen-binding protein by cation exchange. The chromatographic conditions for this separation were as follows: PolyCAT A column, 200×4.6mm, operated at 0.62 ml/min.; load buffer and second buffer as in Example 1; gradient program from 100 percent load buffer A to 0 percent load buffer A over 48 mins; sample was CC49/212, 1.66 mg/ml; injection volume 0.2 ml. Fractions were collected from the two peaks from a similar chromatogram and identified as monomeric and bivalent proteins using gel filtration HPLC chromatography as described below.

Figure 12:
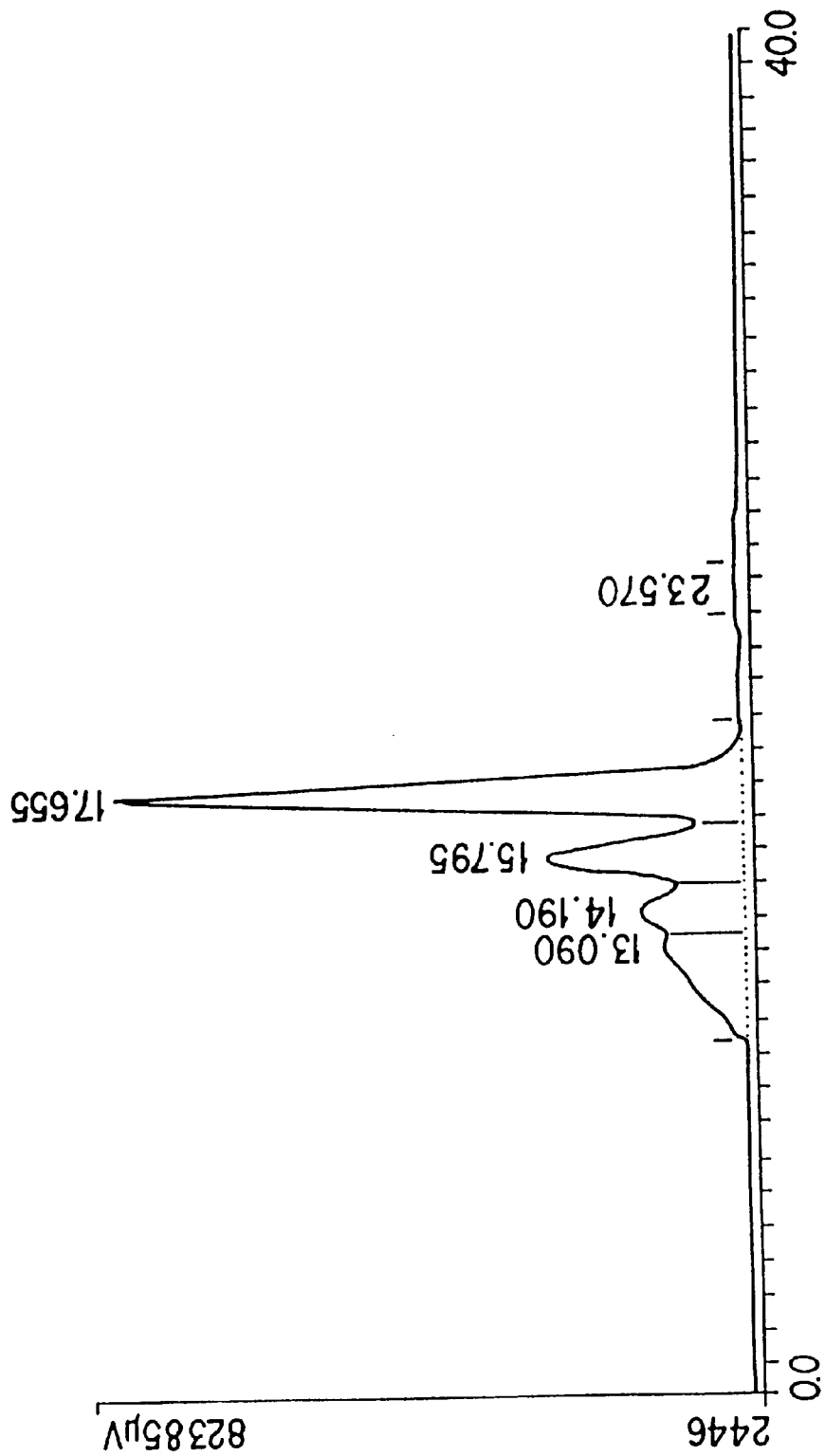
FIG. 12 shows the separation of monomer (17.65 min.), dimer (15.79 min.), trimer (14.19 min.), and higher oligomers (shoulder at about 13.09 min.) of the B6.2/212 antigen-binding protein. This separation depicts the results of a 24-hour treatment of a 1.0 mg/ml B6.2/212 single-chain antigen-binding protein sample. A TSK G2000SW gel filtration HPLC column was used, Toyo Soda, Tokyo, Japan.

Gel filtration HPLC chromatography (TSK G2000SW column from Toyo Soda, Tokyo, Japan) was used to identify and separate monomeric single-chain and multivalent antigen-binding proteins. This procedure has been described by Fukano, et al., *J. Chromatography* 166:47 (1978). Multimerization (creation of multivalent protein from monomeric single-chain protein) was by treatment with 0.5 M GuHCl and 20% EtOH for the times indicated in Table 2A followed by dialysis into the chromatography buffer. FIG. 12 shows the separation of monomeric (17.65 min.), bivalent (15.79 min.), trivalent (14.19 min.), and higher oligomers (shoulder at about 13.09 min.) of the B6.2/212 antigen-binding protein. The B6.2/212 single-chain antigen-binding protein is described in Colcher, D., et al., *J. Nat. Cancer Inst.* 82:1191–1197 (1990)). This separation depicts the results of a 24-hour multimerization treatment of a 1.0 mg/ml B6.2/212 antigen-binding protein sample. The HPLC buffer used was 0.04 M MOPS, 0.10 M calcium acetate, 0.04% sodium azide, pH 7.5.

Figure 13:
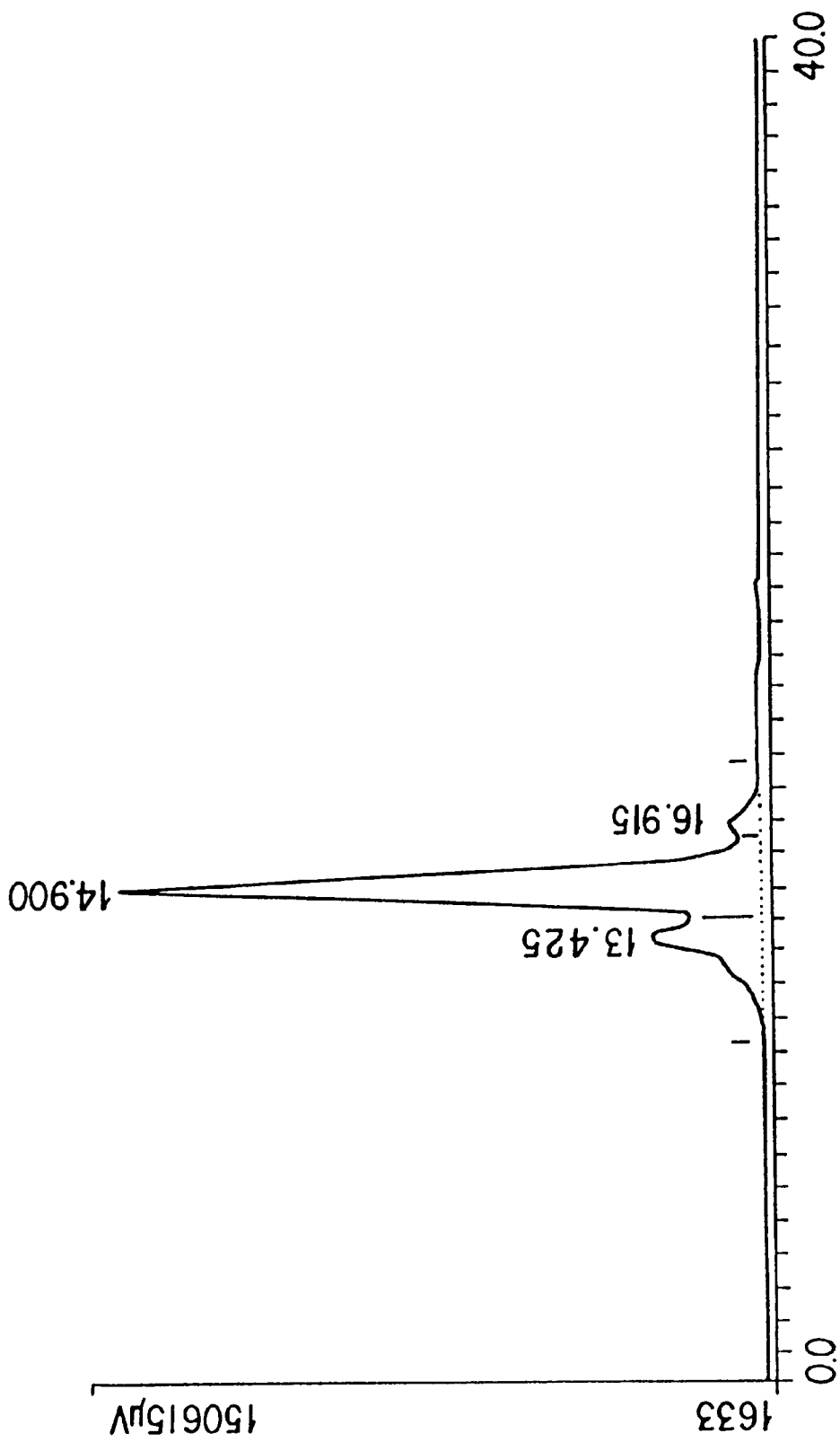
FIG. 13 shows the results of a 24-hour treatment of a 4.0 mg/ml CC49/212 antigen-binding protein sample, generating monomer, dimer, and trimer at 16.91, 14.9, and 13.42 min., respectively. The same TSK gel filtration column was used as in FIG. 12.

FIG. 13 shows the results of a 24-hour treatment of a 4.0 mg/ml CC49/212 antigen-binding protein sample, generating monomeric, bivalent and trivalent proteins at 16.91, 14.9, and 13.42 min., respectively. The HPLC buffer was 40 mM MOPS, 100 mM calcium acetate, pH 7.35. Multimerization treatment was for the times indicated in Table 2.

The results of Example 2A are shown in Table 2A. Table 2A shows the percentage of bivalent and other multivalent forms before and after treatment with 20% ethanol and 0.5M GuHCl. Unless otherwise indicated, percentages were determined using a automatic data integration software package.

TABLE 2A

Summary of the generation of bivalent and higher multivalent forms of B6.2/212 and CC49/212 proteins using guanidine hydrochloride and ethanol

| protein | Time (hours) | Concentration (mg/ml) | % monomer | dimer | trimer | multimers |
|---|---|---|---|---|---|---|
| CC49/212 | 0 | 0.25 | 86.7 | 11.6 | 1.7 | 0.0 |
|  | 0 | 1.0[2] | 84.0 | 10.6 | 5.5 | 0.0 |
|  | 0 | 4.0 | 70.0 | 17.1 | 12.9[1] | 0.0 |
|  | 2 | 0.25[2] | 62.9 | 33.2 | 4.2 | 0.0 |
|  | 2 | 1.0 | 24.2 | 70.6 | 5.1 | 0.0 |
|  | 2 | 4.0 | 9.3 | 81.3 | 9.5 | 0.0 |
|  | 26 | 0.25 | 16.0 | 77.6 | 6.4 | 0.0 |
|  | 26 | 1.0 | 9.2 | 82.8 | 7.9 | 0.0 |
|  | 26 | 4.0 | 3.7 | 78.2 | 18.1 | 0.0 |
| B6.2/212 | 0 | 0.25 | 100.0 | 0.0 | 0.0 | 0.0 |
|  | 0 | 1.0 | 100.0 | 0.0 | 0.0 | 0.0 |
|  | 0 | 4.0 | 100.0 | 0.0 | 0.0 | 0.0 |
|  | 2 | 0.25[2] | 98.1 | 1.9 | 0.0 | 0.0 |
|  | 2 | 1.0 | 100.0 | 0.0 | 0.0 | 0.0 |
|  | 2 | 4.0 | 90.0 | 5.5 | 1.0 | 0.0 |
|  | 24 | 0.25 | 45.6 | 37.5 | 10.2 | 6.7 |
|  | 24 | 1.0 | 50.8 | 21.4 | 12.3 | 15.0 |
|  | 24 | 4.0 | 5.9 | 37.2 | 25.7 | 29.9 |

[1]Based on cut out peaks that were weighed.
[2]Average of two experiments.

B. Process Using Urea and Ethanol

Multivalent antigen-binding proteins were produced from purified single-chain proteins in the following way. First the purified single-chain protein at a concentration of 0.25–1 mg/ml was dialyzed against 2M urea, 20% ethanol (EtOH), and 50 mM Tris buffer pH 8.0, for the times indicated in Table 2B. This combination of dissociating agents is thought to disrupt the $V_L/V_H$ interface, allowing the $V_H$ of a first single-chain molecule to come into contact with a $V_L$ from a second single-chain molecule. Other dissociating agents such as isopropanol or methanol should be substitutable for EtOH. Following the initial dialysis, the protein was dialyzed against the load buffer for the final HPLC purification step.

Gel filtration HPLC chromatography (TSK G2000SW column from Toyo Soda, Tokyo, Japan) was used to identify and separate monomeric single-chain and multivalent antigen-binding proteins. This procedure has been described by Fukano, et al., *J. Chromatography* 166:47 (1978).

The results of Example 2B are shown in Table 2B. Table 2B shows the percentage of bivalent and other multivalent forms before and after treatment with 20% ethanol and urea. Percentages were determined using an automatic data integration software package.

TABLE 2B

Summary of the generation of bivalent and higher multivalent forms of B6.2/212 and CC49/212 proteins using urea and ethanol

| protein | Time (hours) | Concentration (mg/ml) | % monomer | dimer | trimer | multimers |
|---|---|---|---|---|---|---|
| B6.2 | 0 | 0.25 | 44.1 | 37.6 | 15.9 | 2.4 |
|  | 0 | 1.0 | 37.7 | 33.7 | 19.4 | 9.4 |
|  | 3 | 0.25 | 22.2 | 66.5 | 11.3 | 0.0 |
|  | 3 | 1.0 | 13.7 | 69.9 | 16.4 | 0.0 |

EXAMPLE 3

Determination of Binding Constants

Three anti-fluorescein single-chain antigen-binding proteins have been constructed based on the anti-fluorescein monoclonal antibody 4-4-20. The three 4-4-20 single-chain antigen-binding proteins differ in the polypeptide linker connecting the $V_H$ and $V_L$ regions of the protein. The three linkers used were 202', 212 and 216 (see Table 3). Bivalent and higher forms of the 4-4-20 antigen-binding protein were produced by concentrating the purified monomeric single-chain antigen-binding protein in the cation exchange load buffer (0.06 M MOPS, 0.001 M calcium acetate pH 6.4) to 5 mg/ml. The bivalent and monomeric forms of the 4-4-20 antigen-binding proteins were separated by cation exchange HPLC (polyaspartate column) using a 50 min. linear gradient between the load buffer (0.06 M MOPS, 0.001 M calcium acetate pH 6.4) and a second buffer (0.06 M MOPS, 0.02 M calcium acetate pH 7.5). Two 0.02 ml samples were separated, and fractions of the bivalent and monomeric protein peaks were collected on each run. The amount of protein contained in each fraction was determined from the absorbance at 278 nm from the first separation. Before collecting the fractions from the second separation run, each fraction tube had a sufficient quantity of $1.03 \times 10^5$ M fluorescein added to it, such that after the fractions were collected a 1-to-1 molar ratio of protein-to-fluorescein existed. Addition of fluorescein stabilized the bivalent form of the 4-4-20 antigen-binding proteins. These samples were kept at 2° C. (on ice).

The fluorescein dissociation rates were determined for each of these samples following the procedures described by Herron, J. N., in *Fluorescence Hapten: An Immunological Probe*, E. W. Voss, Ed., CRC Press, Boca Raton, Fla. (1984). A sample was first diluted with 20 mM HEPES buffer pH 8.0 to $5.0 \times 10^{-8}$ M 4-4-20 antigen-binding protein. 560 µl of the $5.0 \times 10^{-8}$ M 4-4-20 antigen-binding protein sample was added to a cuvette in a fluorescence spectrophotometer equilibrated at 2° C. and the fluorescence was read. 140 µl of $1.02 \times 10^{-5}$ M fluoresceinamine was added to the cuvette, and the fluorescence was read every 1 minute for up to 25 minutes (see Table 4).

The binding constants ($K_a$) for the 4-4-20 single-chain antigen-binding protein monomers diluted in 20 mM HEPES buffer pH 8.0 in the absence of fluorescein were also determined (see Table 4).

The three polypeptide linkers in these experiments differ in length. The 202', 212 and 216 linkers are 12, 14 and 18 residues long, respectively. These experiments show that there are two effects of linker length on the 4-4-20 antigen-binding proteins: first, the shorter the linker length the higher the fraction of bivalent protein formed; second, the fluorescein dissociation rates of the monomeric single-chain antigen-binding proteins are effected more by the linker length than are the dissociation rates of the bivalent antigen-binding proteins. With the shorter linkers 202' and 212, the bivalent antigen-binding proteins have slower dissociation rates than the monomers. Thus, the linkers providing optimum production and binding affinities for monomeric and bivalent antigen-binding proteins may be different. Longer linkers may be more suitable for monomeric single-chain antigen-binding proteins, and shorter linkers may be more suitable for multivalent antigen-binding proteins.

TABLE 3

Linker Designs

| $V_L$ | Linker | $V_H$ | Linker Name | Reference |
|---|---|---|---|---|
| -KLEIE | GKSSGSGSESKS[1] | TQKLD- | 202' | Bird et al. |
| -KLEIK | GSTSGSGKSSEGKG[2] | EVKLD- | 212 | Bedzyk et al. |
| -KLEIK | GSTSGSGKSSEGSGSTKG[3] | EVKLD- | 216 | This application |
| -KLVLK | GSTSGKPSEGKG[4] | EVKLD- | 217 | This application |

([1]) SEQ ID NO. 1
([2]) SEQ ID NO. 2
([3]) SEQ ID NO. 3
([4]) SEQ ID NO. 4

TABLE 4

Effects of Linkers on the SCA Protein Monomers and Dimers

| | Linker | | |
|---|---|---|---|
| | 202' | 212 | 216 |
| Monomer | | | |
| Fraction | 0.47 | 0.66 | 0.90 |
| Ka | $0.5 \times 10^9 M^{-1}$ | $1.0 \times 10^9 M^{-1}$ | $1.3 \times 10^9 M^{-1}$ |
| Dissociation rate | $8.2 \times 10^{-3} s^{-1}$ | $4.9 \times 10^{-3} s^{-1}$ | $3.3 \times 10^{-3} s^{-1}$ |
| Dimer | | | |
| Fraction | 0.53 | 0.34 | 0.10 |
| Dissociation rate | $4.6 \times 10^{-3} s^{-1}$ | $3.5 \times 10^{-3} s^{-1}$ | $3.5 \times 10^{-3} s^{-1}$ |
| Monomer/Dimer | | | |
| Dissociation rate ratio | 1.8 | 1.4 | 0.9 |

Genetic Construction of a Mixed-Fragment Bivalent Antigen-Binding Protein

The genetic constructions for one particular heterobivalent antigen-binding protein according to the Rearrangement model are shown in FIGS. 10A and 10B. FIG. 10A is an amino acid and nucleotide sequence listing of the 4-4-20 $V_L/212/CC49$ $V_H$ construct, coding for a single-chain protein with a 4-4-20 $V_L$, linked via a 212 polypeptide linker to a CC49 $V_H$. FIG. 10B is a similar listing showing the CC49 $V_L/212/4$-4-20 $V_H$ construct, coding for a single-chain protein with a CC49 $V_L$, linked via a 212 linker to a 4-4-20 $V_H$. These single-chain proteins may recombine according to the Rearrangement model to generate a heterobivalent protein comprising a CC49 antigen-binding site linked to a 4-4-20 antigen-binding site, as shown in FIG. 5B.

"4-4-20 VL" means the variable region of the light chain of the 4-4-20 mouse monoclonal antibody (Bird, R. E. et al., Science 242:423 (1988)). The number "212" refers to a specific 14-residue polypeptide linker that links the 4-4-20 $V_L$ and the CC49 $V_H$. See Bedzyk, W. D. et al., J. Biol. Chem. 265:18615–18620 (1990). "CC49 $V_H$" is the variable region of the heavy chain of the CC49 antibody, which binds to the TAG-72 antigen. The CC49 antibody was developed at The National Institutes of Health by Schlom, et al.

region is indicated generally. Thus the hinge from human IgG1 would start with LysH218 or SerH219. (See Table 5).

The C-terminal residue in most of the single-chain antigen-binding proteins described to date is the amino acid serine. In the design for the hinge region, the C-terminal serine in the 4-4-20/212 single-chain antigen-binding protein was made the first serine of the hinge and the second residue of the hinge was changed from a cysteine to a serine. This hinge cysteine normally forms a disulfide bridge to the C-terminal cysteine in the light chain.

TABLE 5

|  |  |  |  | 218 |  |  |  |  |  |  |  |  |  |  |  |  |
|---|---|---|---|---|---|---|---|---|---|---|---|---|---|---|---|---|
| IgG2A mouse[1] |  |  | E | P | R | G | P | T | I | K | P |  | C | P | P | C | L | C | — |
| IgG1 human[2] | A | E | P | K |  | S | C | D | K | T | H | T | C | P | P | C | — |
| SCA*[3] | — | — | V | T | V | S |  |  |  |  |  |  |  |  |  |  |  |
| SCA* Hinge design 1[4] | — | — | V | T | V | S | S | D | K | T | H | T | C |  |  |  |  |
| SCA* Hinge design 2[5] | — | — | V | T | V | S | S | D | K | T | H | T | C | P | P | C |  |

*-single-chain antigen-binding protein
([1]) SEQ ID NO. 5
([2]) SEQ ID NO. 6
([3]) SEQ ID NO. 7
([4]) SEQ ID NO. 8
([5]) SEQ ID NO. 9

Generation and Characterization of B72.3 Second Generation Monoclonal Antibodies Reactive With The Tumor-associated Glycoprotein 72 Antigen, Cancer Research 48:4588–4596 (1988).

Insertion of the sequences shown in FIGS. 10A and 10B, by standard recombinant DNA methodology, into a suitable plasmid vector will enable one of ordinary skill in the art to transform a suitable host for subsequent expression of the single-chain proteins. See Maniatis et al., Molecular Cloning, A Laboratory Manual, p. 104, Cold Spring Harbor Laboratory (1982), for general recombinant techniques for accomplishing the aforesaid goals; see also U.S. Pat. No. 4,946,778 (Ladner et al.) for a complete description of methods of producing single-chain protein molecules by recombinant DNA technology.

To produce multivalent antigen-binding proteins from the two single-chain proteins, 4-4-20$V_L$-212/CC49$V_H$ and CC49$V_L$/212/4-4-20$V_H$, the two single-chain proteins are dialyzed into 0.5 M GuHCl/20% EtOH being combined in a single solution either before or after dialysis. The multivalent proteins are then produced and separated as described in Example 2.

EXAMPLE 5

Preparation of Multivalent Antigen-Binding Proteins by Chemical Cross-Linking

Figure 14:
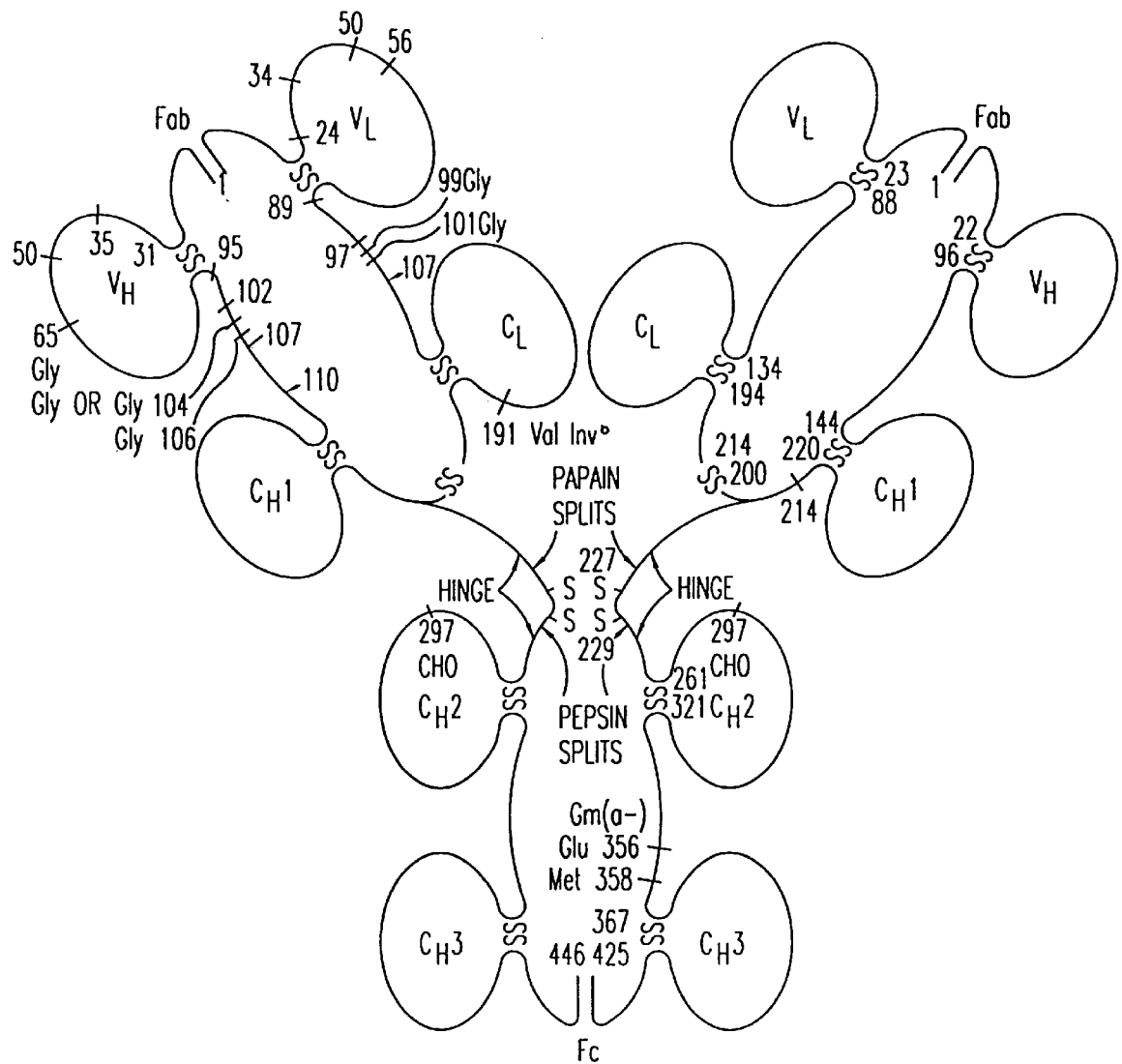
FIG. 14 shows a schematic view of the four-chain structure of a human IgG molecule.

Free cysteines were engineered into the C-terminal of the 4-4-20/212 single-chain antigen-binding protein, in order to chemically crosslink the protein. The design was based on the hinge region found in antibodies between the $C_H1$ and $C_H2$ regions. In order to try to reduce antigenicity in humans, the hinge sequence of the most common IgG class, IgG1, was chosen. The 4-4-20 Fab structure was examined and it was determined that the C-terminal sequence GluH216-ProH217-ArgH218, was part of the $C_H1$ region and that the hinge between $C_H1$ and $C_H2$ starts with ArgH218 or GlyH219 in the mouse 4-4-20 IgG2A antibody. FIG. 14 shows the structure of a human IgG. The hinge There are possible advantages to having two C-terminal cysteines, for they might form an intramolecular disulfide bond, making the protein recovery easier by protecting the sulfurs from oxidation. The hinge regions were added by introduction of a BstE II restriction site in the 3'-terminus of the gene encoding the 4-4-20/212 single-chain antigen-binding protein (see FIGS. 15A–15B).

The monomeric single-chain antigen-binding protein containing the C-terminal cysteine can be purified using the normal methods of purifying a single-chain antigen-binding proteins, with minor modifications to protect the free sulfhydryls. The cross-linking could be accomplished in one of two ways. First, the purified single-chain antigen-binding protein could be treated with a mild reducing agent, such as dithiothreitol, then allowed to air oxidize to form a disulfide-bond between the individual single-chain antigen-binding proteins. This type of chemistry has been successful in producing heterodimers from whole antibodies (Nisonoff et al., Quantitative Estimation of the Hybridization of Rabbit Antibodies, Nature 4826:355–359 (1962); Brennan et al., Preparation of Bispecific Antibodies by Chemical Recombination of Monoclonal Immunoglobulin $G_1$ Fragments, Science 229:81–83 (1985)). Second, chemical crosslinking agents such as bismaleimidehexane could be used to crosslink two single-chain antigen-binding proteins by their C-terminal cysteines. See Partis et al., J. Prot. Chem. 2:263–277 (1983).

EXAMPLE 6

Genetic Construction of Bivalent Antigen-Binding Proteins

Figure 17:
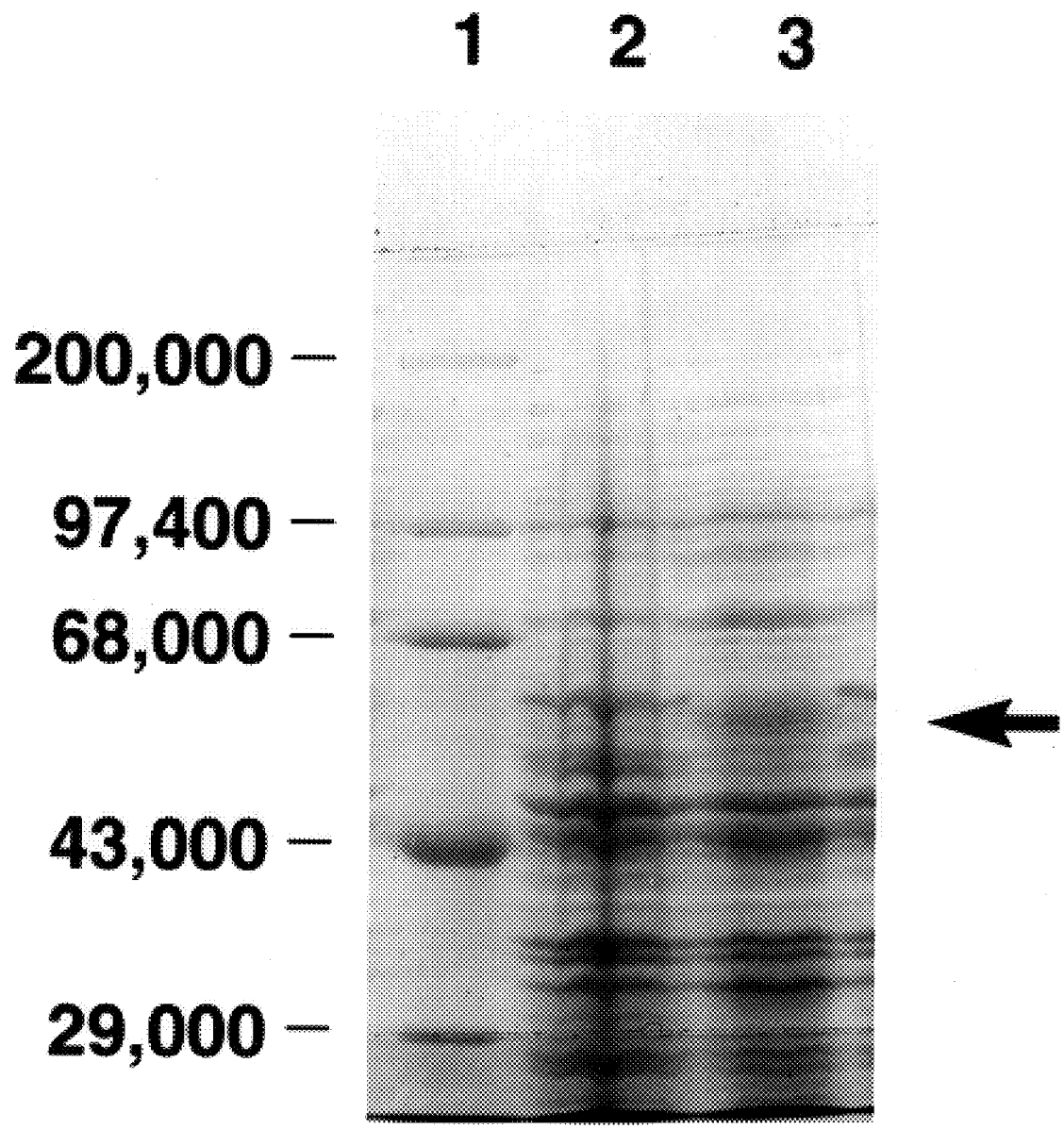
FIG. 17 shows the expression of the divalent CC49/212 single-chain antigen-binding protein of FIG. 16 at 42° C., on an SDS-PAGE gel containing total E. coli protein. Lane 1 contains the molecular weight standards. Lane 2 is the uninduced E. coli production strain grown at 30° C. Lane 3 is divalent CC49/212 single-chain antigen-binding protein induced by growth at 42° C. The arrow shows the band of expressed divalent CC49/212 single-chain antigen-binding protein.

Bivalent antigen-binding proteins can be constructed genetically and subsequently expressed in E. coli or other known expression systems. This can be accomplished by genetically removing the stop codons at the end of a gene encoding a monomeric single-chain antigen-binding protein and inserting a linker and a gene encoding a second single-chain antigen-binding protein. We have constructed a gene for a bivalent CC49/212 antigen-binding protein in this manner (see FIG. 16). The CC49/212 gene in the starting expression plasmid is in an Aat II to Bam H1 restriction fragment (see Bird et al., Single-Chain Antigen-Binding Proteins, Science 242:423–426 (1988); and Whitlow et al., Single-Chain $F_V$ Proteins and Their Fusion Proteins, Methods 2:97–105 (1991)). The two stop codons and the Bam H1 site at the C-terminal end of the CC49/212 antigen-binding protein gene were replaced by a single residue linker (Ser) and an Aat II restriction site. The resulting plasmid was cut with Aat II and the purified Aat II to Aat II restriction fragment was ligated into Aat II cut CC49/212 single-chain antigen-binding protein expression plasmid. The resulting bivalent CC49/212 single-chain antigen-binding protein expression plasmid was transfected into an E. coli expression host that contained the gene for the cI857 temperature-sensitive repressor. Expression of single-chain antigen-binding protein in this system is induced by raising the temperature from 30° C. to 42° C. FIG. 17 shows the expression of the divalent CC49/212 single-chain antigen-binding protein of FIG. 16 at 42° C., on an SDS-PAGE gel containing total E. coli protein. Lane 1 contains the molecular weight standards. Lane 2 is the uninduced E. coli production strain grown at 30° C. Lane 3 is divalent CC49/212 single-chain antigen-binding protein induced by growth at 42° C. The arrow shows the band of expressed divalent CC49/212 single-chain antigen-binding protein.

EXAMPLE 7

Construction, Purification, and Testing of 4-4-20/CC49 Heterodimer $F_V$ With 217 Linkers.

The goals of this experiment were to produce, purify and analyze for activity a new heterodimer $F_V$ that would bind to both fluorescein and the pan-carcinoma antigen TAG-72. The design consisted of two polypeptide chains, which associated to form the active heterodimer Fv. Each polypeptide chain can be described as a mixed single-chain Fv (mixed sFv). The first mixed sFv (GX 8952) comprised a 4-4-20 variable light chain ($V_L$) and a CC49 variable heavy chain ($V_H$) connected by a 217 polypeptide linker (FIG. 19A). The second mixed sFv (GX 8953) comprised a CC49 $V_L$ and a 4-4-20 $V_H$ connected by a 217 polypeptide linker (FIG. 19B). The sequence of the 217 polypeptide linker is shown in Table 3. Construction of analogous CC49/4-4-20 heterodimers connected by a 212 polypeptide linker as described in Example 4.

RESULTS

A. Purification

One 10-liter fermentation of each mixed sFv was grown on casein digest-glucose-salts medium at 32° C. to an optical density at 600 nm of 15 to 20. The mixed sFv expression was induced by raising the temperature of the fermentation to 42° C. for one hour. 277 gm (wet cell weight) of E. coli strain GX 8952 and 233 gm (wet cell weight) of E. coli strain GX 8953 were harvested in a centrifuge at 7000 g for 10 minutes. The cell pellets were kept and the supernatant discarded. The cell pellets were frozen at −20° C. for storage.

2.55 liters of "lysis/wash buffer" (50 mM Tris/ 200 mM NaCl/1 mM EDTA, pH 8.0) was added to both of the mixed sFv's cell pellets, which were previously thawed and combined to give 510 gm of total wet cell weight. After complete suspension of the cells they were then passed through a Gaulin homogenizer at 9000 psi and 4° C. After this first pass the temperature increased to 23° C. The temperature was immediately brought down to 0° C. using dry ice and methanol. The cell suspension was passed through the Gaulin homogenizer a second time and centrifuged at 8000 rpm with a Dupont GS-3 rotor for 60 minutes. The supernatant was discarded after centrifugation and the pellets resuspended in 2.5 liters of "lysis/wash buffer" at 4° C. This suspension was centrifuged for 45 minutes at 8000 rpm with the Dupont GS-3 rotor. The supernatant was again discarded and the pellet weighed. The pellet weight was 136.1 gm.

1300ml of 6M Guanidine Hydrochloride/50 mM Tris/50 mM KCl/10 mM $CaCl_2$ pH 8.0 at 4° C. was added to the washed pellet. An overhead mixer was used to speed solubilization. After one hour of mixing, the heterodimer GuHCl extract was centrifuged for 45 minutes at 8000 rpm and the pellet was discarded. The 1425 ml of heterodimer Fv 6M GuHCl extract was slowly added (16 ml/min) to 14.1 liters of "Refold Buffer" (50 mM Tris/50 mM KCl/10 mM $CaCl_2$, pH 8.0) under constant mixing at 4° C. to give an approximate dilution of 1:10. Refolding took place overnight at 4° C.

After 17 hours of refolding the anti-fluorescein activity was checked by a 40% quenching assay, and the amount of active protein calculated. 150mg total active heterodimer Fv was found by the 40% quench assay, assuming a 54,000 molecular weight.

4 liters of prechilled (4° C.) 190 proof ethanol was added to the 15 liters of refolded heterodimer with mixing for 3 hours. The mixture sat overnight at 4° C. A flocculent precipitate had settled to the bottom after this overnight treatment. The nearly clear solution was filtered through a Millipak-200 (0.22 μ) filter so as to not disturb the precipitate. A 40% quench assay showed that 10% of the anti-fluorescein activity was recovered in the filtrate.

The filtered sample of heterodimer was dialyzed, using a Pellicon system containing 10,000 dalton MWCO membranes, with "dialysis buffer" 40 mM MOPS/0.5mM Calcium Acetate (CaAc), pH 6.4 at 4° C. 20 liters of dialysis buffer was required before the conductivity of the retentate was equal to that of the dialysis buffer (~500 μS). After dialysis the heterodimer sample was filtered through a Millipak-20 filter, 0.22 μ. After this step a 40% quench assay showed there was 8.8 mg of active protein.

The crude heterodimer sample was loaded on a Poly CAT A cation exchange column at 20 ml/min. The column was previously equilibrated with 60 mM MOPS, 1 mM CaAc pH 6.4, at 4° C., (Buffer A). After loading, the column was washed with 150 ml of "Buffer A" at 15 ml/min. A 50 min linear gradient was performed at 15 ml/min using "Buffer A" and "Buffer B" (60 mM MOPS, 20 mM CaAc pH 7.5 at 4° C.). The gradient conditions are presented in Table 6. "Buffer C" comprises 60 mM MOPS, 100 mM $CaCl_2$, pH 7.5.

TABLE 6

| Time | % A | % B | % C | Flow |
| --- | --- | --- | --- | --- |
| 0:00 | 100.0 | 0.0 | 0.0 | 15 ml/min |
| 50:00 | 0.0 | 100.0 | 0.0 | 15 ml/min |
| 52:00 | 0.0 | 100.0 | 0.0 | 15 ml/min |
| 54:00 | 0.0 | 0.0 | 100.0 | 15 ml/min |
| 58:00 | 0.0 | 0.0 | 100.0 | 15 ml/min |
| 60:00 | 100.0 | 0.0 | 0.0 | 15 ml/min |

Figure 20:
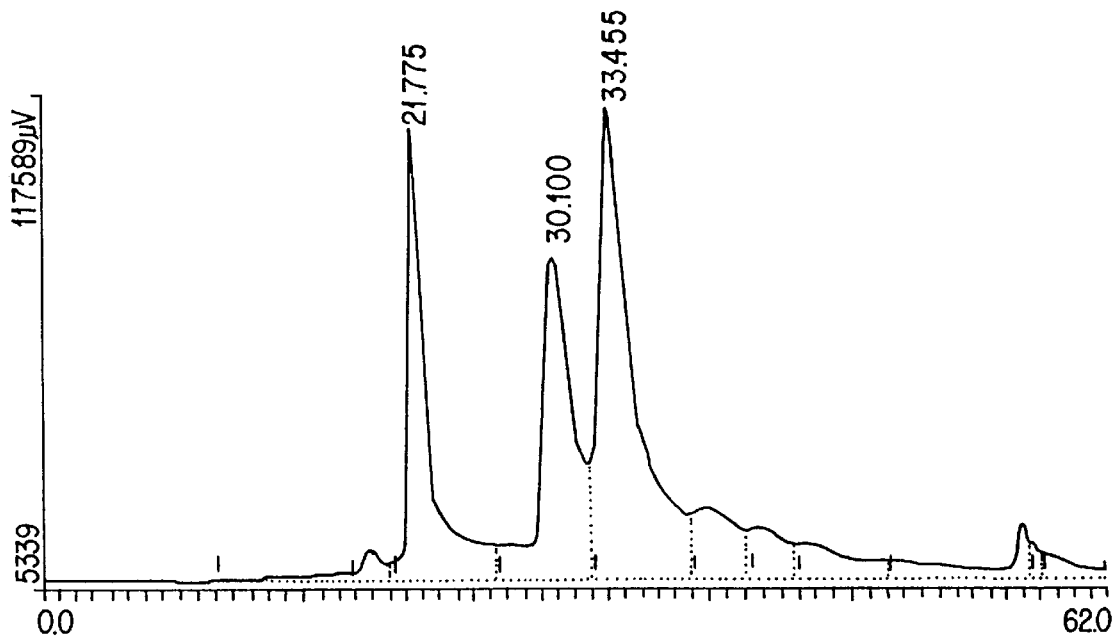
FIG. 20 is a chromatogram depicting the purification of CC49/4-4-20 heterodimer Fv on a cation exchange high performance liquid chromatographic column. The column is a PolyCAT A aspartic acid column (Poly LC, Columbia, Md.). The heterodimer Fv is shown as peak 5, eluting at 30.10 min.

Approximately 50 ml fractions were collected and analyzed for activity, purity, and molecular weight by size-exclusion chromatography. The fractions were not collected by peaks, so contamination between peaks is likely. Fractions 3 through 7 were pooled (total volume–218 ml), concentrated to 50 ml and dialyzed against 4 liters of 60 mM MOPS, 0.5 mM CaAc pH 6.4 at 4° C. overnight. The dialyzed pool was filtered through a 0.22 μ filter and checked for absorbance at 280 nm. The filtrate was loaded onto the PolyCAT A column, equilibrated with 60 mM MOPS, 1 mM CaAc pH 6.4 at 4° C., at a flow rate of 10 ml/min. Buffer B was changed to 60 mM MOPS, 10 mM CaAc pH 7.5 at 4° C. The gradient was run as in Table 6. The fractions were collected by peak and analyzed for activity, purity, and molecular weight. The chromatogram is shown in FIG. 20. Fraction identification and analysis is presented in Table 7.

TABLE 7

Fraction Analysis of the Heterodimer Fv protein

| Fraction No. | $A_{280}$ reading | Total Volume (ml) | HPLC-SE Elution Time (min) |
|---|---|---|---|
| 2 | 0.161 | 36 | 20.525 |
| 3 | 0.607 | 40 | |
| 4 | 0.033 | 40 | |
| 5 | 0.178 | 45 | 19.133 |
| 6 | 0.234 | 50 | 19.163 |
| 7 | 0.069 | 50 | |
| 8 | 0.055 | 40 | |

Figure 21:
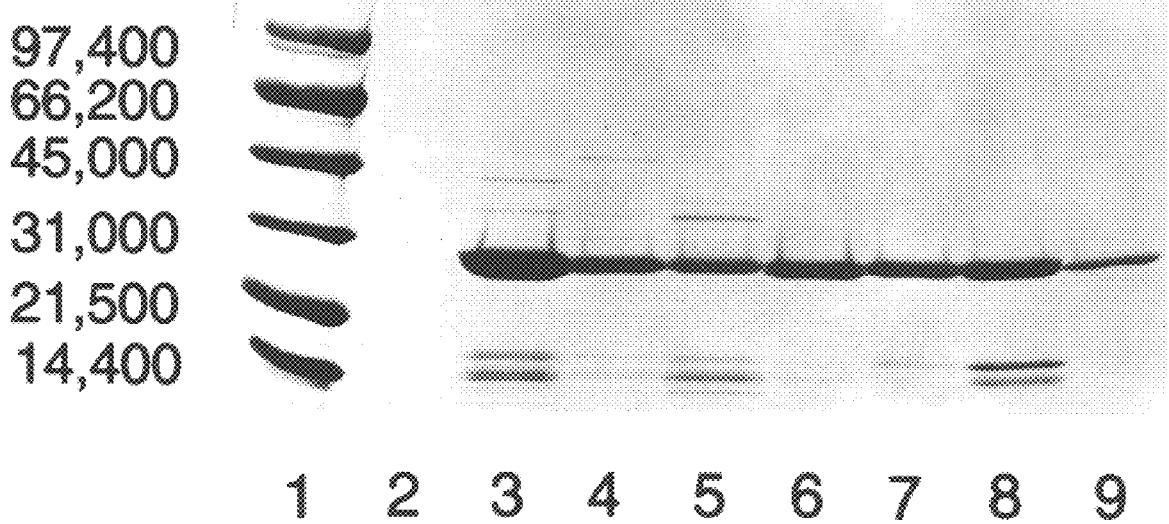
FIG. 21 is a Coomassie-blue stained 4–20% SDS-PAGE gel showing the proteins separated in FIG. 20. Lane 1 contains the molecular weight standards. Lane 3 contains the starting material before separation. Lanes 4–8 contain fractions 2, 3, 5, 6 and 7 respectively. Lane 9 contains purified CC49/212.

Fractions 2 to 7 and the starting material were analyzed by SDS gel electrophoresis, 4–20%. A picture and description of the gel is presented in FIG. 21.

B. HPLC Size Exclusion Results

Figure 22A:
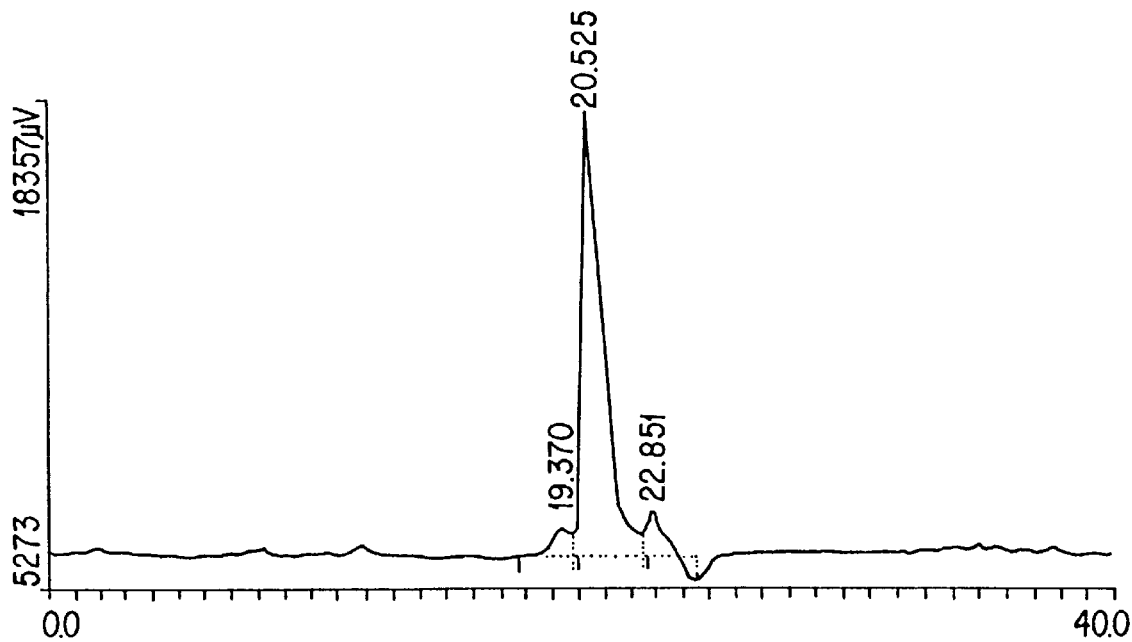
FIG. 22A is a chromatogram used to determine the molecular size of fraction 2 from FIG. 20. A TSK G3000SW gel filtration HPLC column was used (Toyo Soda, Tokyo, Japan).
Figure 22B:
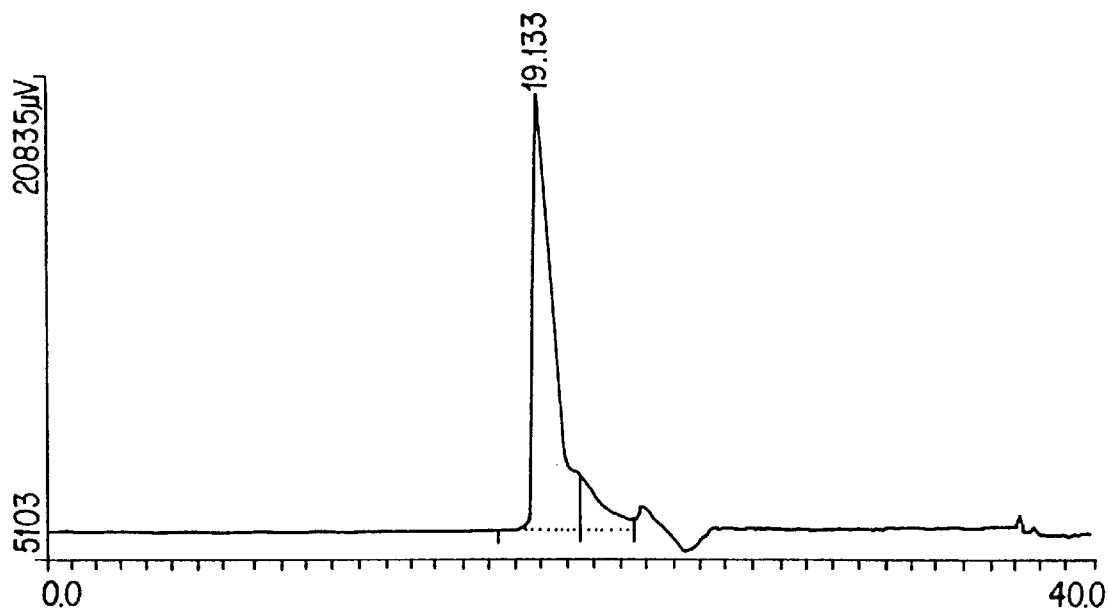
FIG. 22B is a chromatogram used to determine the molecular size of fraction 5 from FIG. 20. A TSK G3000SW gel filtration HPLC column was used (Toyo Soda, Tokyo, Japan).
Figure 22C:
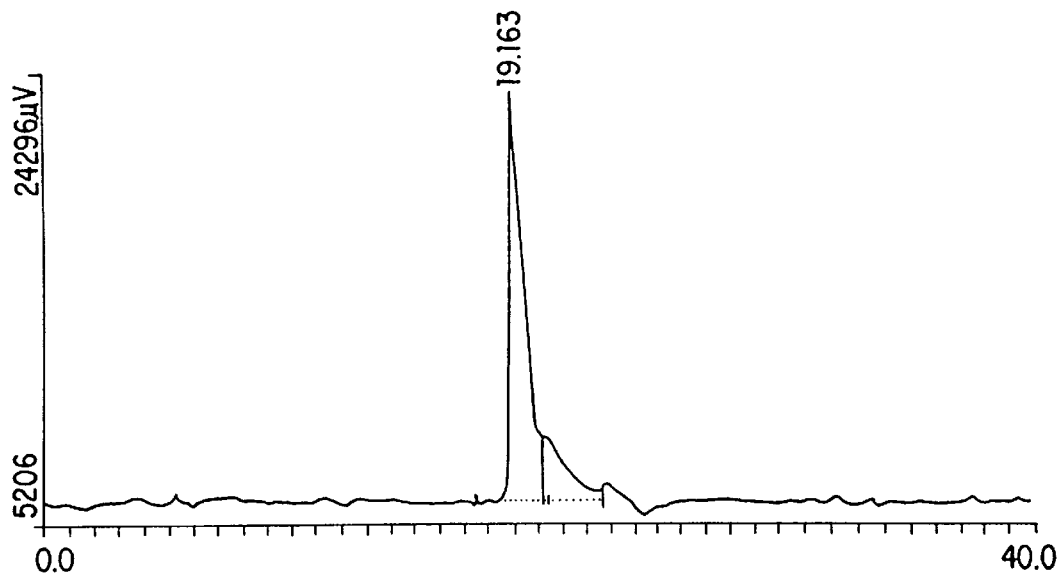
FIG. 22C is a chromatogram used to determine the molecular size of fraction 6 from FIG. 20. A TSK G3000SW gel filtration HPLC column was used (Toyo Soda, Tokyo, Japan).

Fractions 2, 5, and 6 correspond to the three main peaks in FIG. 20 and therefore were chosen to be analyzed by HPLC size exclusion. Fraction 2 corresponds to the peak that runs at 21.775 minutes in the preparative purification (FIG. 20), and runs on the HPLC sizing column at 20.525 minutes, which is in the monomeric position (FIG. 22A). Fractions 5 and 6 (30.1 and 33.455 minutes, respectively, in FIG. 20) run on the HPLC sizing column (FIGS. 22B and 22C) at 19.133 and 19.163 minutes, respectively (see Table 7). Therefore, both of these peaks could be considered dimers. 40% Quenching assays were performed on all fractions of this purification. Only fraction 5 gave significant activity. 2.4 mg of active CC49 4-4-20 heterodimer Fv was recovered in fraction 5, based on the Scatchard analysis described below.

C. N-terminal sequencing of the fractions

The active heterodimer Fv fraction should contain both polypeptide chains. N-terminal sequence analysis showed that fractions 5 and 6 displayed N-terminal sequences consistent with the prescence of both CC49 and 4-4-20 polypeptides and fraction 2 displayed a single sequence corresponding to the CC49/212/4-4-20 polypeptide only. We believe that fraction 6 was contaminated by fraction 5 (see FIG. 20), since only fraction 5 had significant activity.

D. Anti-fluorescein activity by Scatchard analysis

Figure 23:
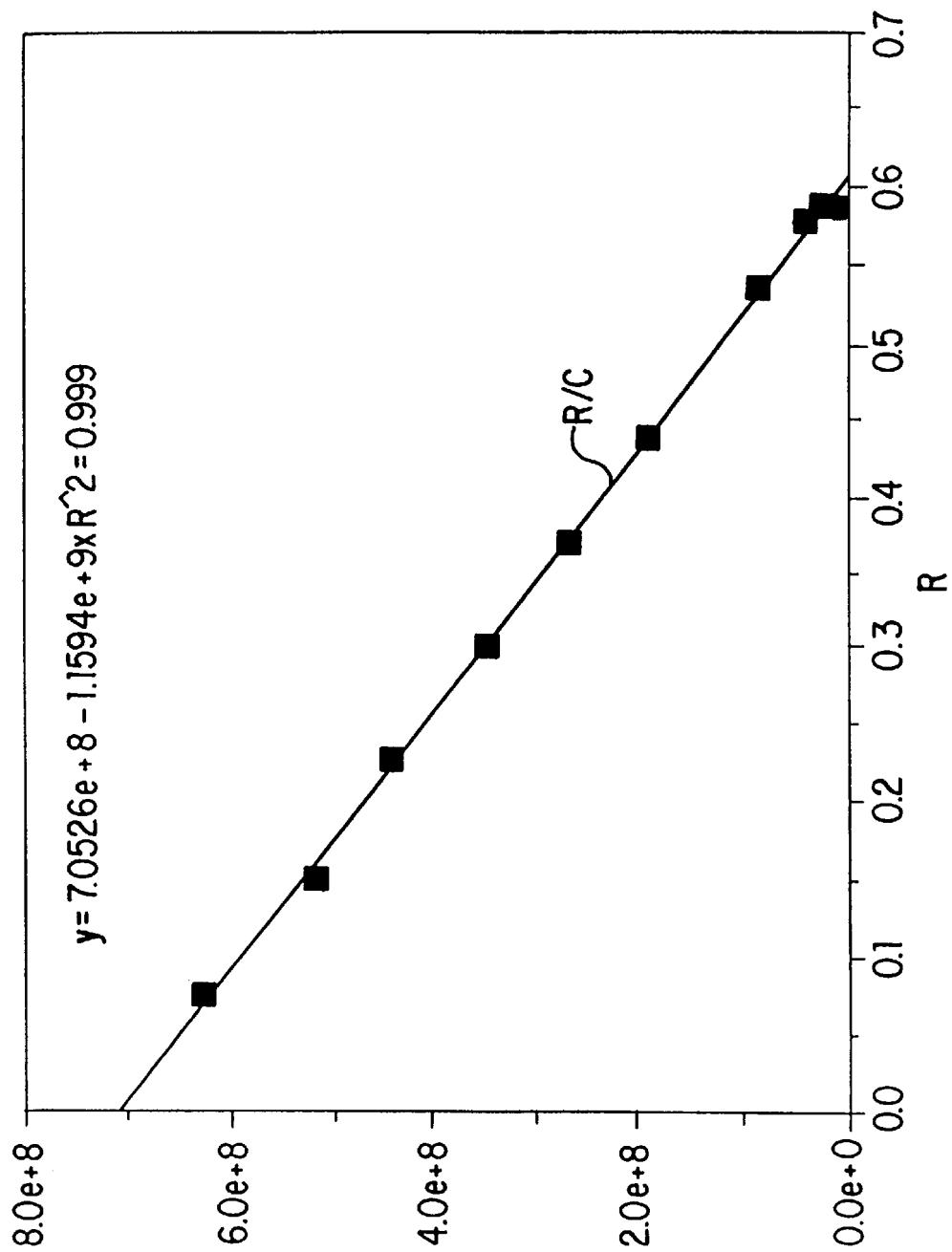
FIG. 23 shows a Scatchard analysis of the fluorescein binding affinity of the CC49 4-4-20 heterodimer Fv (fraction 5 in FIG. 20).

The fluorescein association constants (Ka) were determined for fractions 5 and 6 using the fluorescence quenching assay described by Herron, J. N., in *Fluorescence Hapten: An Immunological Probe*, E. W. Voss, ed., CRC Press, Boca Raton, Fla. (1984). Each sample was diluted to approximately $5.0 \times 10^{-8}$ M with 20 mM HEPES buffer pH 8.0. 590 μl of the $5.0 \times 10^{-8}$ M sample was added to a cuvette in a fluorescence spectrophotometer equilibrated at room temperature. In a second cuvette 590 μl of 20 mM HEPES buffer pH 8.0 was added. To each cuvette was added 10 μl of $3.0 \times 10^{-7}$ M fluorescein in 20 mM HEPES buffer pH 8.0, and the fluorescence recorded. This is repeated until 140 μl of fluorescein had been added. The resulting Scatchard analysis for fraction 5 shows a binding constant of $1.16 \times 10^{-9}$ $M^{-1}$ for fraction #5 (see FIG. 23). This is very close to the 4-4-20/212 sFv constant of $1.1 \times 10^9$ $M^{-1}$ (see Pantoliano et al., *Biochemistry* 30:10117–10125 (1991)). The R intercept on the Scatchard analysis represents the fraction of active material. For fraction 5, 61% of the material was active. The graph of the Scatchard analysis on fraction 6 shows a binding constant of $3.3 \times 10^8$ $M^{-1}$ and 14% active. The activity that is present in fraction 6 is most likely contaminants from fraction 5.

E. Anti-TAG-72 activity by competition ELISA

The CC49 monoclonal antibody was developed by Dr. Jeffrey Schlom's group, Laboratory of Tumor Immunology and Biology, National Cancer Institute. It binds specifically to the pan-carcinoma tumor antigen TAG-72. See Muraro, R., et al., *Cancer Research* 48:4588–4596 (1988).

Figure 24:
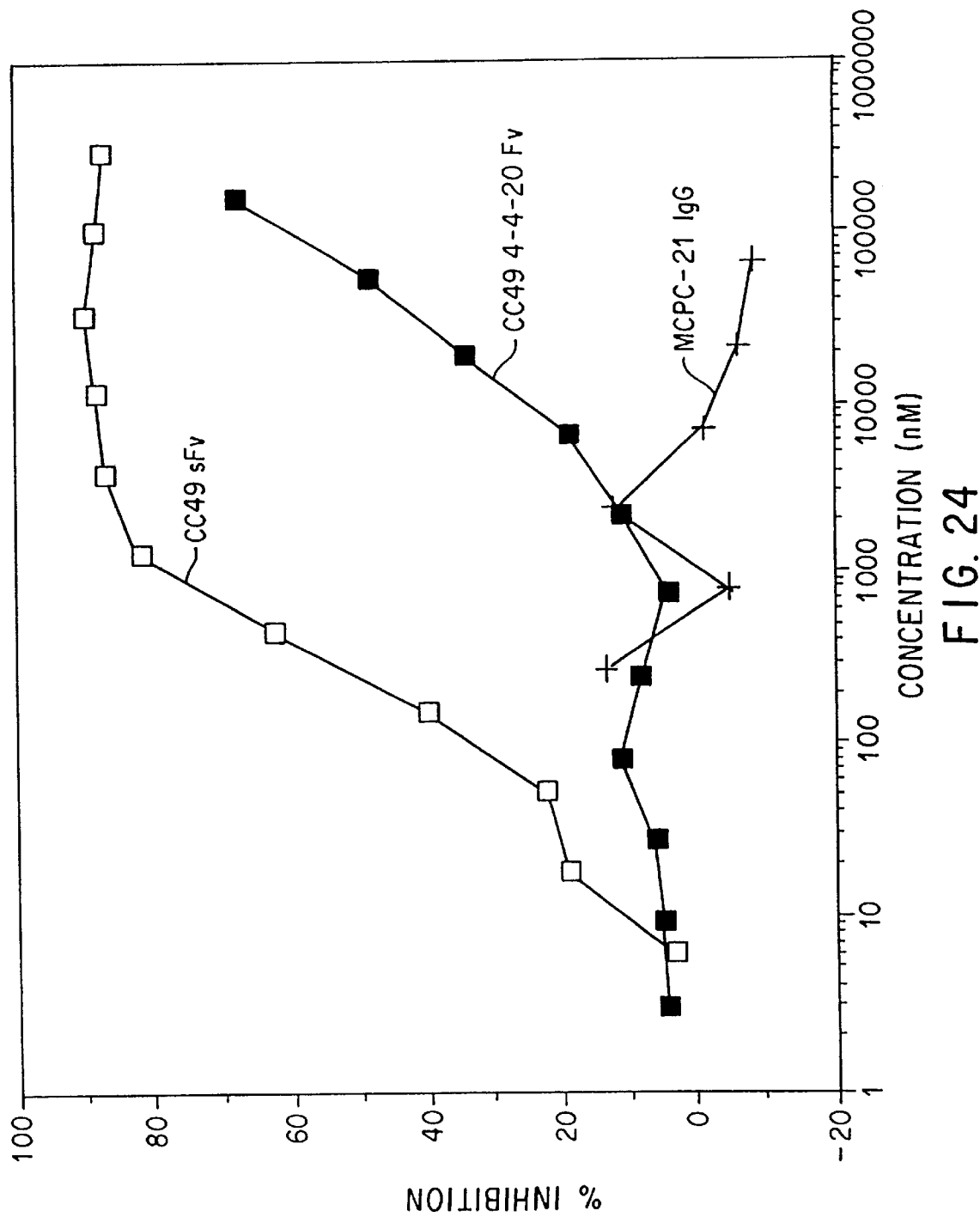
FIG. 24 is a graphical representation of three competition enzyme-linked immunosorbent assays (ELISA) in which unlabeled CC49 4-4-20 Fv (closed squares) CC49/212 single-chain Fv (open squares) and MOPC-21 IgG (+) competed against a biotin-labeled CC49 IgG for binding to the TAG-72 antigen on a human breast carcinoma extract. MOPC-21 is a control antibody that does not bind to TAG-72 antigen.

To determine the binding properties of the bivalent CC49/4-4-20 Fv (fraction 5) and the CC49/212 sFv, a competition enzyme-linked immunosorbent assay (ELISA) was set up in which a CC49 IgG labeled with biotin was competed against unlabeled CC49/4-4-20 Fv and the CC49/212 sFv for binding to TAG-72 on a human breast carcinoma extract (see FIG. 24). The amount of biotin-labeled CC49 IgG was determined using a preformed complex with avidin and biotin coupled to horse radish peroxidase and O-phenylenediamine dihydrochloride (OPD). The reaction was stopped with $4N H_2SO_4$ (sulfuric acid), after 10 min. and the optical density read at 490 nm. This competition ELISA showed that the bivalent CC49/4-4-20 Fv binds to the TAG-72 antigen. The CC49/4-4-20 Fv needed a two hundred-fold higher protein concentration to displace the IgG than the single-chain Fv.

EXAMPLE 8

Cross-Linking Antigen-Binding Dimers

We have chemically crosslinked dimers of 4-4-20/212 antigen-binding protein with the two cysteine C-terminal extension (4-4-20/212 CPPC single-chain antigen-binding protein) in two ways. In Example 5 we describe the design and genetic construction of the 4-4-20/212 CPPC single-chain antigen-binding protein (hinge design 2 in Table 5). FIG. 15B shows the nucleic acid and protein sequences of this protein. After purifying the 4-4-20/212 CPPC single-chain antigen-binding protein, using the methods described in Whitlow and Filpula, *Meth. Enzymol.* 2:97 (1991), dimers were formed by two methods. First, the free cysteines were mildly reduced with dithiothreitol (DTT) and then the disulfide-bonds between the two molecules were allowed to form by air oxidation. Second, the chemical crosslinker bismaleimidehexane was used to produce dimers by crosslinking the free cysteines from two 4-4-20/212 CPPC single-chain antigen-binding proteins.

Figure 25:
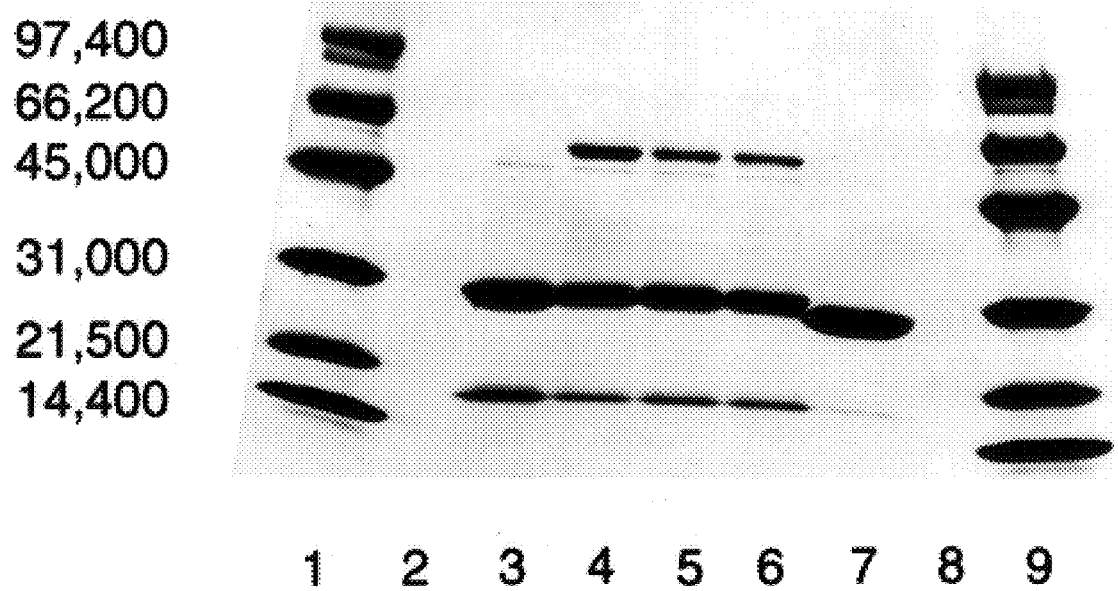
FIG. 25 shows a Coomassie-blue stained non-reducing 4-20% SDS-PAGE gel. Lanes 1 and 9 contain the molecular weight standards. Lane 3 contains the 4-4-20/212 CPPC single-chain antigen-binding protein after purification. Lane 4, 5 and 6 contain the 4-4-20/212 CPPC single-chain antigen-binding protein after treatment with DTT and air oxidation. Lane 7 contains 4-4-20/212 single-chain antigen-binding protein.

A 0.1 mg/ml solution of the 4-4-20/212 CPPC single-chain antigen-binding protein was mildly reduced using 1 mM DTT, 50 mM HEPES, 50 mM NaCl, 1 mM EDTA buffer pH 8.0 at 4° C. The samples were dialyzed against 50 mM HEPES, 50 mM NaCl, 1 mM EDTA buffer pH 8.0 at 4° C. overnight, to allow the oxidation of free sulfhydrals to intermolecular disulfide-bonds. FIG. 25 shows a non-reducing SDS-PAGE gel after the air oxidation; it shows that approximately 10% of the 4-4-20/212 CPPC protein formed dimers with molecular weights around 55,000 Daltons.

Figure 26:
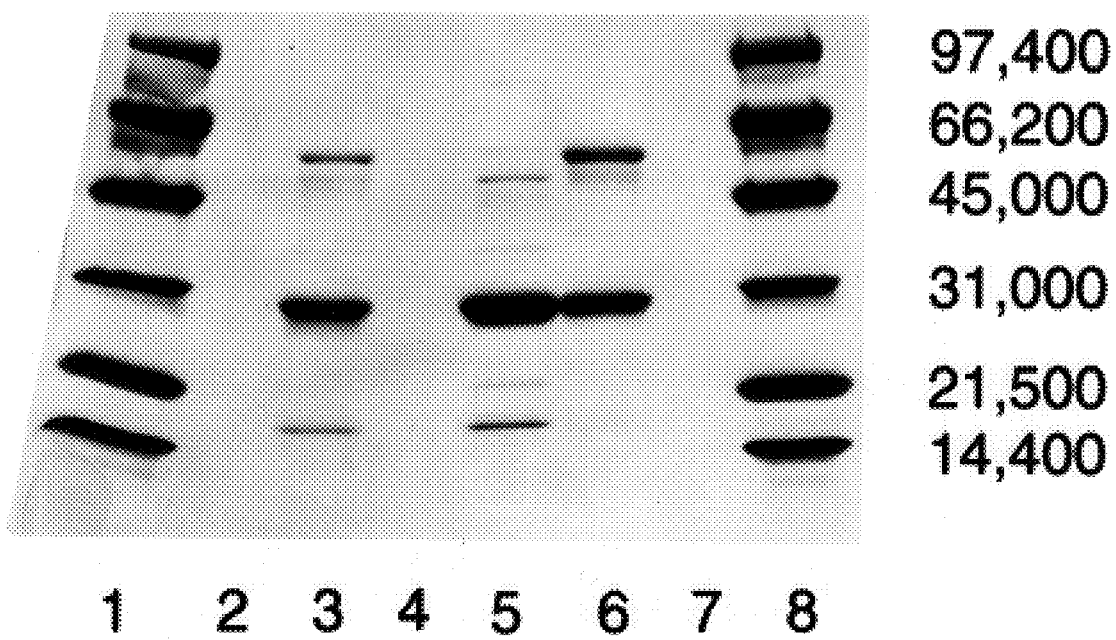
FIG. 26 shows a Coomassie-blue stained reducing 4–20% SDS-PAGE gel (samples were treated with β-mercaptoethanol prior to being loaded on the gel). Lanes 1 and 8 contain the molecular weight standards. Lane 3 contains the 4-4-20/212 CPPC single-chain antigen-binding protein after treatment with bis-maleimidehexane. Lane 5 contains peak 1 of bis-maleimidehexane treated 4-4-20/212 CPPC single-chain antigen-binding protein. Lane 6 contains peak 3 of bis-maleimidehexane treated 4-4-20/212 CPPC single-chain antigen-binding protein.

A 0.1 mg/ml solution of the 4-4-20/212 CPPC single-chain antigen-binding protein was treated with 2 mM bis-maleimidehexane. Unlike forming a disulfide-bond between two free cysteines in the previous example, the bismaleimidehexane crosslinker material should be stable to reducing agents such as β-mercaptoethanol. FIG. 26 shows that approximately 5% of the treated material produced dimer with a molecular weight of 55,000 Daltons on a reducing SDS-PAGE gel (samples were treated with β-mercaptalethanol prior to being loaded on the gel). We further purified the bis-maleimidehexane treated 4-4-20/212 CPPC protein on PolyCAT A cation exchange column after the protein had been extensively dialyzed against buffer A. FIG. 26 shows that we were able to enhance the fraction containing the dimer to approximately 15%.

CONCLUSIONS

We have produced a heterodimer Fv from two complementary mixed sFv's which has been shown to have the size of a dimer of the sFv's. The N-terminal analysis has shown that the active heterodimer Fv contains two polypeptide chains. The heterodimer Fv has been shown to be active for both fluorescein and TAG-72 binding.

All publications cited herein are incorporated fully into this disclosure by reference.

From the foregoing it will be appreciated that, although specific embodiments of the invention have been described herein for purposes of illustration, various modifications may be made without deviating from the spirit and scope of the invention and the following claims. As examples, the steps of the preferred embodiment constitute only one form of carrying out the process in which the invention may be embodied.

What is claimed is:

1. A composition comprising an antigen-binding protein having more than 50% of said protein in multivalent form, said protein in multivalent form comprising two or more single-chain molecules, each single-chain molecule comprising:
   (a) a first polypeptide comprising the binding portion of the variable region of an antibody light chain;
   (b) a second polypeptide comprising the binding portion of the variable region of an antibody heavy chain; and
   (c) a peptide linker linking said first and second polypeptides (a) and (b); or
   (d) a first polypeptide comprising the binding portion of the variable region of an antibody heavy chain;
   (e) a second polypeptide comprising the binding portion of the variable region of an antibody light chain; and
   (f) a peptide linker linking said first and second polypeptides (d) and (e); wherein said protein in multivalent form is either conjugated to a therapeutically or diagnostically effective agent or has binding specificity for at least two different antigen wherein one of said antigens comprises a therapeutically or diagnostically effective agent.

2. The composition according to claim 1, said composition having more than 84% of said protein in multivalent form.

3. The composition according to claim 1, said composition having more than 95% of said protein in multivalent form.

4. The composition of claim 1 wherein said therapeutically or diagnostically effective agent is a therapeutically effective agent.

5. The composition of claim 1 wherein said therapeutically or diagnostically effective agent is a diagnostically effective agent.

6. The composition of claim 4 wherein said therapeutically effective agent is a host cytotoxic cell.

7. The composition of claim 6 wherein said host cytotoxic cell is a natural killer or cytotoxic T cell.

8. The composition of claim 4 wherein said therapeutically effective agent is a cytotoxic compound.

9. The composition of claim 8 wherein said cytotoxic compound is a protein.

10. The composition of claim 4 wherein said therapeutically effective agent is an anti-cancer, non-protein drug.

11. The composition of claim 5 wherein said diagnostically effective agent comprises a detectable label.

12. The composition of claim 11 wherein said detectable label is a chemiluminescent label.

13. The composition of claim 11 wherein said detectable label is a chromophoric label.

14. The composition of claim 11 wherein said detectable label is a radioactive label.

15. The composition according to claim 1 wherein said single-chain molecules are non-covalently linked to each other.

16. The composition according to claim 1 wherein said single-chain molecules are chemically cross-linked to each other.

17. A composition comprising an antigen-binding protein having more than 50% of said protein in multivalent form, said protein in multivalent form comprising
  (a) two or more different single chain molecules, each single chain molecule comprising:
    (i) a first polypeptide comprising the binding portion of the variable region of a heavy or light chain of a CC49 monoclonal antibody having ATCC Accession No. HB-9459;
    (ii) a second polypeptide comprising the binding portion of the variable region of a heavy or light chain of a CC49 monoclonal antibody having ATCC Accession No. HB-9459; and
    (iii) a peptide linker linking said first and second polypeptides; or
  (b) two or more single chain molecules, each single chain molecule comprising:
    (i) a first polypeptide comprising the binding portion of the variable region of a heavy chain of a CC49 monoclonal antibody having ATCC Accession No. HB-9459
    (ii) a second polypeptide comprising the binding portion of the variable region of a light chain of a CC49 monoclonal antibody having ATCC Accession No. HB-9459; and
    (iii) a peptide linker linking said first and second polypeptides;
  wherein the light chain variable region of one single chain molecule of (a) associates with the heavy chain variable region of another single chain molecule of (a) to form an antigen-binding site; or
  wherein the light chain variable region of one single chain molecule of (b) associates with the heavy chain variable region of another single chain molecule of (b) to form an antigen-binding site; and
  wherein said protein in multivalent form is either conjugated to a therapeutically or diagnostically effective agent or has binding specificity for at least two different antigens, wherein one of said antigens comprises a therapeutically or diagnostically effective agent.

18. The composition of claim 17 wherein said peptide linker is selected from the group consisting of linkers 202'(SEQ ID NO:1), 212 (SEQ ID NO:2), 216 (SEQ ID NO:3), and 217 (SEQ ID NO:4).

19. The composition of claim 17 wherein said therapeutically or diagnostically effective agent is a therapeutically effective agent.

20. The composition of claim 17 wherein said therapeutically or diagnostically effective agent is a diagnostically effective agent.

21. The composition according to claim 17 wherein said single-chain molecules are non-covalently linked to each other.

22. The composition according to claim 17 wherein said single-chain molecules are chemically cross-linked to each other.

23. The composition according to claim 22, said composition having more than 84% of said protein in multivalent form.

24. The composition according to claim 22, said composition having more than 95% of said protein in multivalent form.

25. The composition according to claim 1, wherein said protein in multivalent form is conjugated to a therapeutically or diagnostically effective agent.

26. The composition according to claim 1, wherein said protein in multivalent form has binding specificity for at least two different antigens, wherein one of said antigens comprises a therapeutically or diagnostically effective agent.

27. The composition according to claim 17, wherein said protein in multivalent form is conjugated to a therapeutically or diagnostically effective agent.

28. The composition according to claim 17, wherein said protein in multivalent form has binding specificity for at least two different antigens, wherein one of said antigens comprises a therapeutically or diagnostically effective agent.

* * * * *

UNITED STATES PATENT AND TRADEMARK OFFICE
CERTIFICATE OF CORRECTION

PATENT NO. : 6,121,424
DATED : September 19, 2000
INVENTOR(S) : Whitlow et al.

It is certified that error appears in the above-identified patent and that said Letters Patent is hereby corrected as shown below:

<u>Title page,</u>
Item [75], after "Whitlow," delete "Gaithersburg" and insert therein -- El Sobrante, Ca. --.
After "Filpula,", delete "Gaithersburg, Md." and insert therein -- Piscataway, NJ. --.

<u>Column 4,</u>
Line 33, delete "gentic" and insert therein -- genetic --.

<u>Column 7,</u>
Line 34, delete "peak" and insert therein -- fraction --.

<u>Column 14,</u>
Line 31, delete "Tris-Hcl" and insert therein -- Tris-HCl --.

<u>Column 19,</u>
Line 43, delete "$10^5$ M" and insert therein -- $10^{-5}$ M --.

<u>Column 21,</u>
Line 45, delete "4-4-20$V_L$-212/CC49$V_H$" and insert therein -- 4-4-20$V_L$/212/CC49$V_H$ --.
Line 56, after "C-terminal", insert -- end --.

<u>Column 23,</u>
Lines 46-47, delete "as described" and insert therein -- were described --.

Signed and Sealed this

Twenty-fourth Day of September, 2002

*Attest:*

JAMES E. ROGAN
*Attesting Officer*     *Director of the United States Patent and Trademark Office*